US010759824B2

(12) United States Patent
O'Halloran et al.

(10) Patent No.: US 10,759,824 B2
(45) Date of Patent: *Sep. 1, 2020

(54) DESIGN, SYNTHESIS AND USE OF SYNTHETIC NUCLEOTIDES COMPRISING CHARGE MASS TAGS

(71) Applicant: QuantuMDx Group Limited, Newcastle (GB)

(72) Inventors: Jonathan O'Halloran, Uckfield (GB); Joseph H. Hedley, Tyne and Wear (GB)

(73) Assignee: QUANTUMDX GROUP LIMITED, Newcastle Upon Tyne (GB)

( * ) Notice: Subject to any disclaimer, the term of this patent is extended or adjusted under 35 U.S.C. 154(b) by 862 days.

This patent is subject to a terminal disclaimer.

(21) Appl. No.: 14/987,687

(22) Filed: Jan. 4, 2016

(65) Prior Publication Data

US 2016/0139133 A1 May 19, 2016

Related U.S. Application Data

(63) Continuation-in-part of application No. 14/522,185, filed on Oct. 23, 2014, now abandoned, which is a continuation of application No. 13/062,206, filed as application No. PCT/IB2009/007025 on Sep. 3, 2009, now Pat. No. 8,871,921.

(60) Provisional application No. 61/094,025, filed on Sep. 3, 2008.

(51) Int. Cl.
| | | |
|---|---|---|
| *C07H 19/10* | (2006.01) |
| *G01N 33/58* | (2006.01) |
| *C07H 19/048* | (2006.01) |
| *C07H 19/14* | (2006.01) |
| *C12Q 1/6816* | (2018.01) |

(52) U.S. Cl.
CPC ........... *C07H 19/10* (2013.01); *C07H 19/048* (2013.01); *C07H 19/14* (2013.01); *C12Q 1/6816* (2013.01); *G01N 33/58* (2013.01); *C12Q 2563/113* (2013.01); *C12Q 2563/167* (2013.01); *C12Q 2565/607* (2013.01); *C12Q 2565/629* (2013.01); *G01N 2560/00* (2013.01)

(58) Field of Classification Search
CPC .................................................... C07H 19/10
USPC ...................... 536/23.1, 24.3, 26.6
See application file for complete search history.

(56) References Cited

U.S. PATENT DOCUMENTS

| | | | |
|---|---|---|---|
| 6,310,189 B1 | 10/2001 | Fodor et al. |
| 8,871,921 B2 | 10/2014 | O'Halloran |
| 10,273,261 B2* | 4/2019 | O'Halloran ............ C07H 19/10 |
| 2001/0036672 A1 | 11/2001 | Anderson et al. |
| 2003/0104437 A1 | 6/2003 | Barnes et al. |
| 2003/0215816 A1 | 11/2003 | Sundararajan et al. |
| 2005/0123958 A1 | 6/2005 | Tsuchiya |
| 2005/0164205 A1 | 7/2005 | Puskas |
| 2007/0190546 A1 | 8/2007 | Siddiqi et al. |
| 2007/0219367 A1* | 9/2007 | Shchepinov ......... C12Q 1/6869 536/25.32 |
| 2007/0238186 A1 | 10/2007 | Sun et al. |
| 2010/0035260 A1 | 2/2010 | Olasagasti et al. |
| 2010/0093992 A1 | 4/2010 | Cherkasov et al. |
| 2011/0165572 A1 | 7/2011 | O'Halloran |
| 2012/0074925 A1 | 3/2012 | Oliver |
| 2015/0276709 A1 | 2/2015 | O'Halloran et al. |
| 2015/0259731 A1 | 9/2015 | O'Halloran |
| 2019/0004055 A1 | 1/2019 | O'Halloran et al. |

FOREIGN PATENT DOCUMENTS

| | | |
|---|---|---|
| CN | 1617937 | 5/2005 |
| CN | 10184853 | 5/2008 |
| CN | 202284206 U | 6/2012 |
| CN | 101076537 B | 7/2012 |
| CN | 102242062 A | 12/2012 |
| JP | 2005-503114 | 2/2005 |
| JP | 2005-511058 | 4/2005 |
| JP | 2005-526512 | 9/2005 |
| JP | 2007-195548 | 8/2007 |
| JP | 2008-534018 | 8/2008 |
| WO | 97/28282 A1 | 8/1997 |
| WO | 02/063030 A2 | 8/2002 |
| WO | 03/052139 A1 | 6/2003 |
| WO | 03048387 | 6/2003 |
| WO | 03/091406 A2 | 11/2003 |
| WO | 03/100096 A1 | 12/2003 |
| WO | 2006001944 A1 | 1/2006 |
| WO | 2006/095981 A1 | 9/2006 |
| WO | 2006/097320 A2 | 9/2006 |

(Continued)

OTHER PUBLICATIONS

International Search Report and Written Opinion dated Apr. 28, 2017 in International Application No. PCT/US2017/012065, filed Jan. 3, 2017 in 14 pages.
International Search Report and Written Opinion in International Application No. PCT/IB2013/002168 dated Dec. 12, 2013 in 3 pages.
Office Action dated Jul. 15, 2016 in Japanese Patent Application No. 2015-133481, in 15 pages.
Reexamination Notification dated May 26, 2017 in Chinese Application No. 200980142508.2, filed Sep. 3, 2009.
Notice of Allowance dated May 8, 2017 in Japanese Application No. 2015-132532, filed Jul. 21, 2015.
Office Action dated Jun. 23, 2017 in Indian Application No. 1752/DELNP/2011, filed Sep. 3, 2009.

(Continued)

*Primary Examiner* — Jezia Riley
(74) *Attorney, Agent, or Firm* — Knobbe, Martens, Olson & Bear, LLP

(57) ABSTRACT

Embodiments of the present disclosure relate generally to reporter compositions which are synthetic nucleotides that comprise nucleotides with a high charge mass moiety attached thereto via a linker molecule. The linker molecules can vary in length in part to enable the high charge mass moiety to extend out from a DNA polymerase complex so that polymerization may not be influenced.

20 Claims, 5 Drawing Sheets

(4 of 5 Drawing Sheet(s) Filed in Color)

(56) References Cited

FOREIGN PATENT DOCUMENTS

| WO | 2006/105360 | A1 | 10/2006 |
|---|---|---|---|
| WO | 2007062160 | | 5/2007 |
| WO | 2007/077952 | A1 | 7/2007 |
| WO | 2008/070749 | A1 | 6/2008 |
| WO | 2008079169 | A2 | 7/2008 |
| WO | 2009/006445 | A2 | 1/2009 |
| WO | 2010002939 | A2 | 1/2010 |
| WO | 2010/026488 | A2 | 3/2010 |
| WO | 2010/026490 | A1 | 3/2010 |
| WO | 2010/028140 | A2 | 3/2010 |
| WO | 2014/024041 | A1 | 2/2014 |

OTHER PUBLICATIONS

Barrato, C., et al. "SnO2 nanowire bio-transistor for electrical DNA sensing", IEEE Sensors 2007 Conference, pp. 1132-1135.
Cui, Y., et al., "Nanowire Nanosensors for Highly Sensitive and Selective Detection of Biological and Chemical Species", Science, vol. 293, Aug. 17, 2001, pp. 1289-1292.
Rejection Decision in Chinese Patent Application 200980142508.2, dated Jul. 4, 2016 in 17 pages.
Office Action dated Jul. 19, 2017 in European Patent Application No. 15188427.7.
Summons to Attend Oral Proceedings Pursuant to Rule 115(1) EPC 2017 in European Patent Application No. 15188427.7.
Notice of Allowance dated Dec. 13, 2018 in U.S. Appl. No. 16/067,776.
Kumar et al. "Terminal Phosphate Labeled Nucleotides: Synthesis, Applications, and Linker Effect on Incorporation by DNA Polymerases", Nucleosides, Nucleotides and Nucleic Acids, 24 pp. 401-408, 2005.
Stratagene Catalog, 1988, p. 39.
Costa et al., Characterization in vitro and in vivo of the putative multigene 4-coumarate: CoA ligase network in *Arabidopsis*: syringyl lignin and sinapate/sinapyl alcohol derivative formation, Phytochemistry, Sep. 1, 2005, vol. 36, No. 17, pp. 2072-2091.
International Search Report dated Mar. 3, 2010, for International Application No. PCT/IB2009/006976.
International Search Report dated Feb. 19, 2010, for International Application No. PCT/IB2009/005008.
International Search Report dated Feb. 17, 2010, for International Application No. PCT/IB2009/007025.
Maki, W.C. et al., Universal bio-molecular signal transduction-based nano-electronic bio-detection system, Sensors and Actuators B, Aug. 12, 2008, vol. 133, No. 2, pp. 547-554.
Star, A. et al., Label-free detection of DNA hybridization using carbon nanotube network field-effect transistors, Proceedings of the National Academy of Sciences of USA, Jan. 24, 2006, vol. 103, No. 4, pp. 921-926.
Wu, F. Y.-H., et al., "Synthesis and properties of adenosine-5'-triphosphoro-gamma-1-(5-sulfonic acid)naphthyl ethylamidate: A fluorescent nucleotide substrate for DNA-dependent RNA polymerase from *Escherichia coli*," Archives of Biochemistry and Biophysics, May 1, 1986, vol. 246, No. 2, pp. 564-571.
Zhu, Z. et al., "Molecular mechanism controlling the incorporation of fluorescent nucleotides into DNA by PCR," Cytometry, Jan. 1, 1997, vol. 28, pp. 206-211.

* cited by examiner

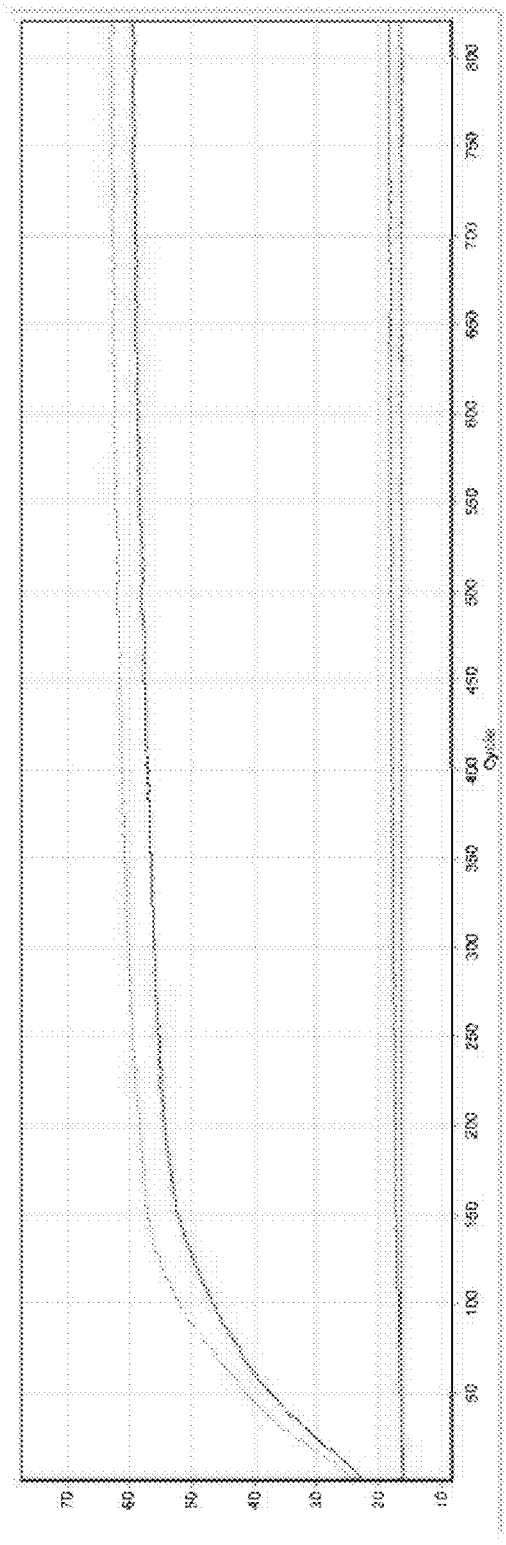
Figure 3A. Extension of the primers in the presence of standard dNTPs (yellow), SC-TTP (blue) and lacking dTTP or DNA polymerase (red and purple respectively).

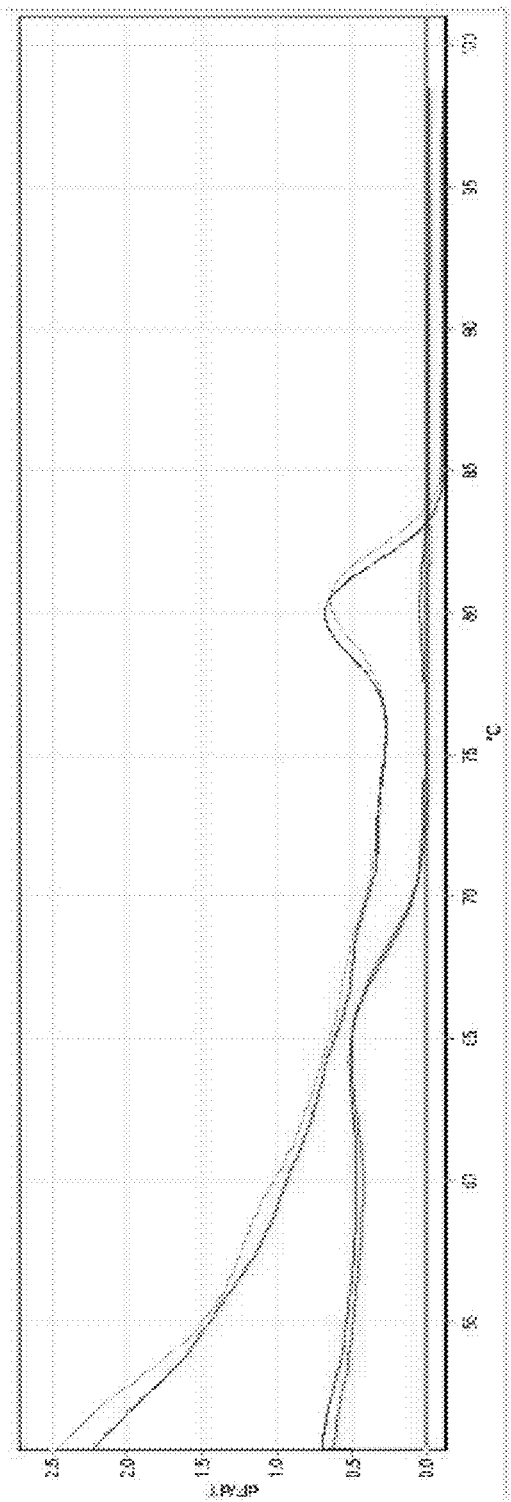
Figure 3B. Melt analysis of end products between the negative (no polymerase, red and purple) and positive (standard dNTPs, yellow) control reactions with melt peaks at 64.3°C and 80.5°C respectively.

DESIGN, SYNTHESIS AND USE OF SYNTHETIC NUCLEOTIDES COMPRISING CHARGE MASS TAGS

CROSS-REFERENCE TO RELATED APPLICATIONS

This application is a Continuation-in-Part application of U.S. application Ser. No. 14/522,185, filed Oct. 23, 2014, which is a Continuation application of U.S. application Ser. No. 13/062,206, filed Mar. 3, 2011 that has been issued to U.S. Pat. No. 8,871,921 on Oct. 28, 2014, which is the national phase under 35 U.S.C. § 371 of prior PCT International Application No. PCT/IB2009/007025 which has an International filing date of Sep. 3, 2009, designating the United States of America, which claims the benefit of U.S. Provisional Patent Application No. 61/094,025 filed on Sep. 3, 2008, the disclosures of which are hereby expressly incorporated by reference in their entirety and are hereby expressly made a portion of this application.

BACKGROUND

Field

Some embodiments of the present disclosure relate generally to synthetic nucleotides that comprise nucleotides with a charge mass reporter molecule via a long linker molecule. The linker molecules can vary in length in part to enable the reporter moiety to extend out from the DNA Polymerase complex so that some aspects of polymerization may not be influenced entirely or partially.

Description of the Related Art

A nucleotide can be defined as a phosphate ester of a nucleoside, comprising a purine or pyrimidine base linked to ribose, or deoxyribose phosphates. The purine nucleotides having chiefly Adenine (A) or Guanine (G) as the base, the pyrimidine nucleotides Cystine (C), Thymoine (T) or Uracil (U), and which are the basic repeating units in DNA and RNA (Henderson's dictionary of biological terms, 1989).

DNA is a long polymer comprising units of deoxyribose nucleotides and RNA is a polymer of ribose nucleotides. This sequence of nucleotide bases can determine individual hereditary characteristics.

The central dogma of molecular biology generally describes the normal flow of biological information: DNA can be replicated to DNA, the genetic information in DNA can be 'transcribed' into mRNA, and proteins can be translated from the information in mRNA, in a process called translation, in which protein subunits (amino acids) are brought close enough to bond, in order (as dictated by the sequence of the mRNA & therefore the DNA) by the binding of tRNA (each tRNA carries a specific amino acid dependant on it's sequence) to the mRNA.

SUMMARY

A reporter composition is disclosed in accordance with embodiments of the present invention. The reporter composition comprises a nucleotide or its derivative, a linker molecule, which may be attached to the nucleotide or its derivative, and a high charge mass moiety, which comprises a charge mass that is sufficient to change a property of a sensitive detection nanostructure or nano- or mico-sensor operably coupled to the reporter composition. In some embodiments, the nucleotide or its derivative present in the reporter composition may be selected from the group consisting of a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof.

In some other embodiments, the linker molecule comprises a molecule of the following general formula, $H_2N$-L-$NH_2$, wherein L may comprise a linear or branched chain comprising one or more selected from the group consisting of an alkyl group, an oxy alkyl group, an alcohol group, a carboxyl group, an aromatic group, a naphthalene group, an amine group, an amide group, any derivatives thereof, and any combination thereof. L in the linker may comprise a linear or branched chain comprising one or more selected from the group consisting of an alkyl group, an oxy alkyl group, an alcohol group, a carboxyl group, an aromatic group, a naphthalene group, an amine group, an amide group, any derivatives thereof, and any combination thereof and a number of the functional group in the linear chain is 1 to 100, 1 to 75, 1 to 50, 1 to 25 or 1 to 1000 in various examples. In some examples, the number of the functional group in the linear or branched chain can be more than 1000. The linker molecule and/or the high charge mass moiety is configured not to affect nucleotide polymerization by a polymerase and also be removable. The linker molecule can be linked to a phosphate group, sugar group or base of the nucleotide or its derivative.

In some embodiments, the high charge mass moiety present in the reporter composition can be positive or negative, and further the charge mass of moiety can be variable depending on pH. In some examples, the high charge mass moiety may comprise an aromatic and/or aliphatic skeleton, wherein the skeleton comprises one or more of a tertiary amino group, an alcohol hydroxyl group, a phenolic hydroxy group, and any combinations thereof. In some examples, the high charge mass moiety comprises one or more of the following groups, any derivatives thereof, and any combinations thereof:

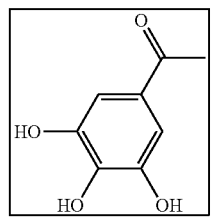

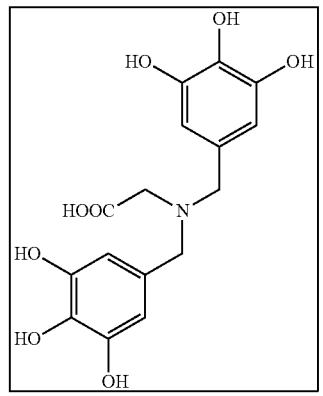

-continued

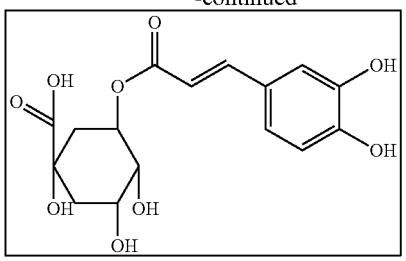

In addition, the number of the foregoing groups, any derivatives thereof, and any combinations thereof present in the high charge mass moiety can be 1 to 10, 11 to 50, 51 to 100, or more than 100 in various embodiments.

In one aspect of the invention, a reporter composition may comprise the following molecule:

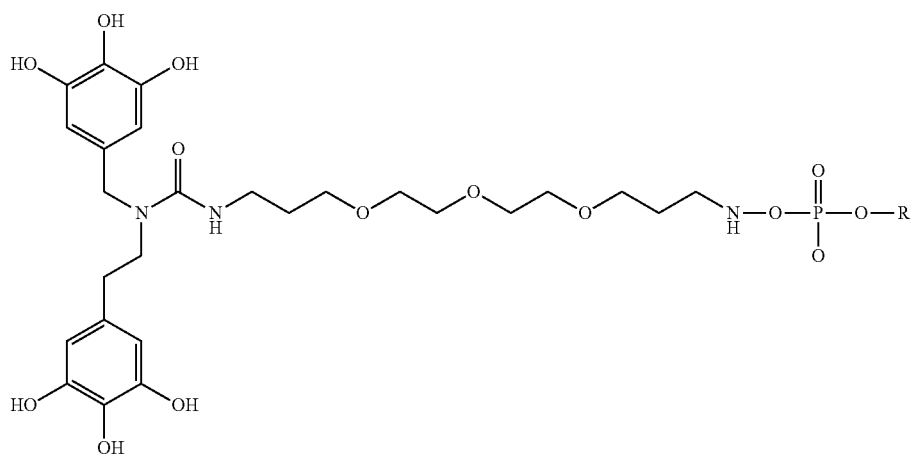

wherein, R is selected from the group consisting of a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof.

In another aspect of the invention, a reporter composition may comprise the following molecule:

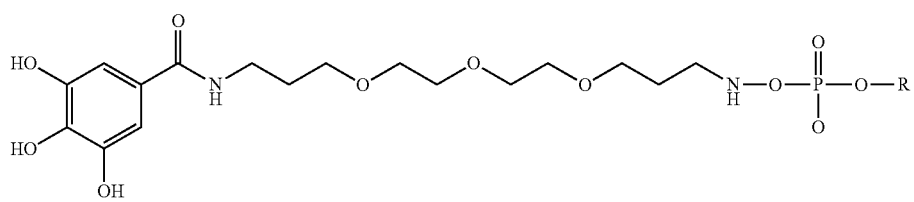

wherein, R is selected from the group consisting of a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof.

In still another aspect of the invention, a reporter composition may comprise the following molecule:

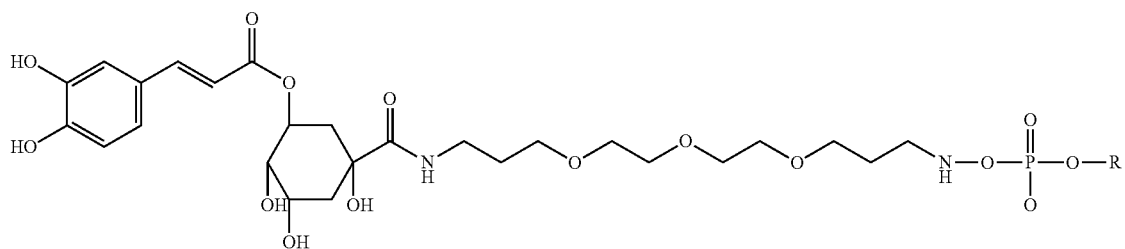

wherein, R is selected from the group consisting of a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof.

A kit for determining a nucleotide sequence, comprising the reporter composition comprising a nucleotide or its derivative, a linker molecule, and a high charge mass moiety is also disclosed in accordance with embodiments of the present invention.

A method of synthesizing the reporter composition is also disclosed. The method comprises: generating a first covalent linkage between the nucleotide or its derivative and a first amine group of the linker, wherein a phosphate group, a sugar or a base of the nucleotide or its derivative is linked to the first amine group of the linker; and generating a second covalent linkage between a second amine group of the linker and any functional group present in the high charge mass moiety; wherein the linker comprises at least two amine groups is also disclosed in connection with the present application. In some embodiments, the nucleotide or its derivate used in the method may comprises a monophosphate group. In some other embodiments, the nucleotide or its derivate used in the method may be selected from the group consisting of adenosine monophosphate (AMP), guanosine monophosphate (GMP), cytidine monophosphate (CMP), thymidine monophosphate (TMP), and uridine monophosphate (UMP).

In still another aspect, a reporter composition comprising a nucleotide or its derivative, a high charge mass moiety comprising an aromatic or aliphatic skeleton, comprising one or more charged groups selected from the group consisting of a tertiary amino group, a carboxyl group, a hydroxyl group, a phosphate group, a phenolic hydroxy group, any derivatives thereof, and any combinations thereof, wherein the one or more charged groups comprise a charge mass that is sufficient to generate a detectable change in a property of a sensitive detection nanostructure or nano-/micro-sensor operably coupled to the reporter composition, and a linker molecule attached to the nucleotide or its derivative and the high charge mass moiety, wherein the linker molecule comprises a linear or branched chain comprising one or more selected from the group consisting of an alkyl group, an oxy alkyl group, an alcohol group, a carboxyl group, an amine group, an amide group, an aromatic group, and a naphthalene group, any derivatives thereof, and any combinations thereof is provided.

In some embodiments, the nucleotide in the reporter composition is selected from the group consisting of a deoxyribonucleotide, a ribonucleotide, a peptide nucleotide, a morpholino, a locked nucleotide, a glycol nucleotide, a threose nucleotide, and a synthetic nucleotide, and any isoforms thereof.

In some other embodiments, the high charge mass moiety in the reporter composition comprises one or more selected from the group consisting of the following compounds 1-5, any derivatives thereof, and any combinations thereof:

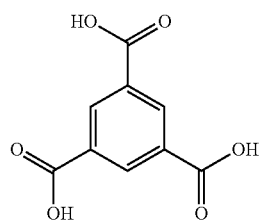

1

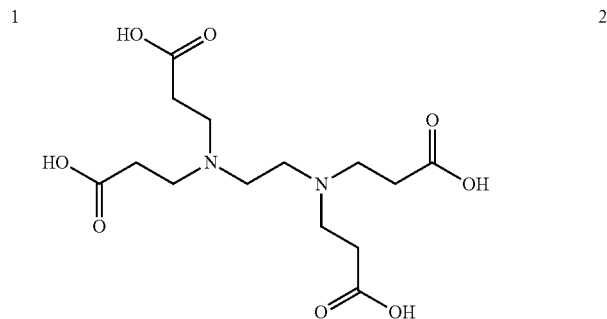

2

3
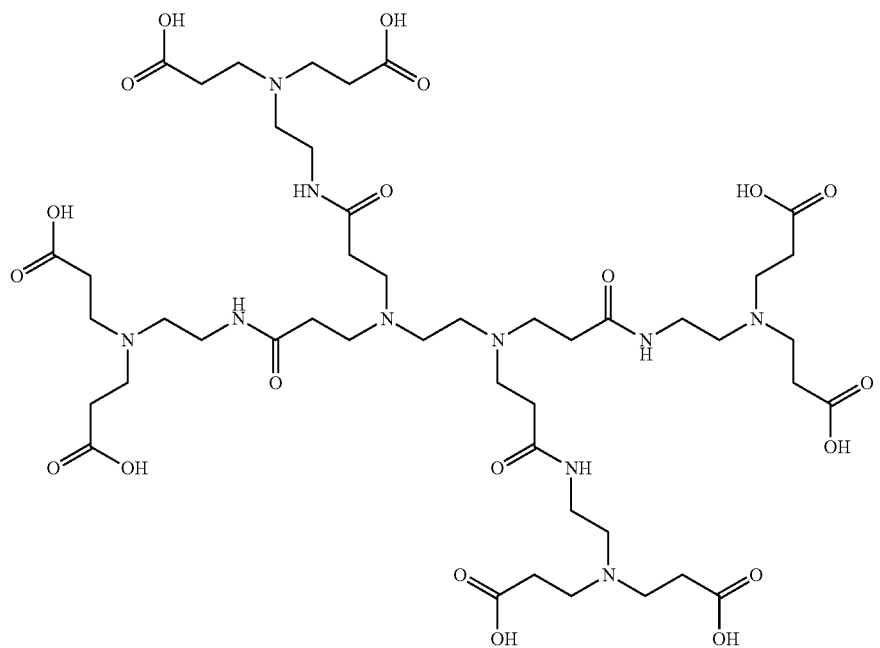
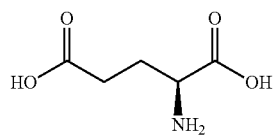
4
5
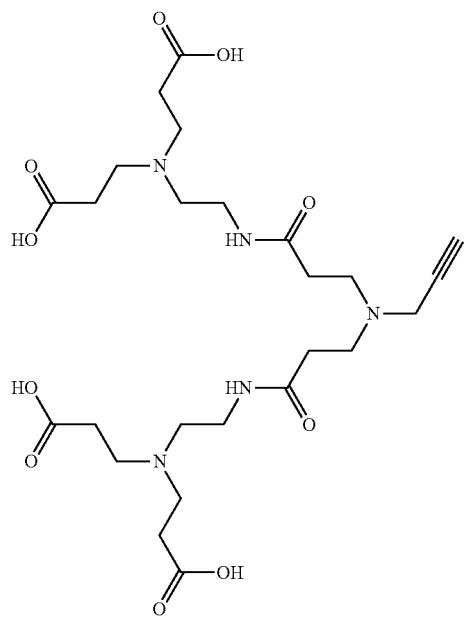

In certain embodiments, the linker molecule in the reporter composition is photocleavable or chemically cleavable. In some of certain embodiments, the chemically cleavable linker molecule comprises one or more selected from the group consisting of: 4-Nitrophenyl 2-(azidomethyl)benzoate, 7-Hydroxy-4-methylcoumarinyl 2-(azidomethyl)benzoate, any derivatives thereof, and any combinations thereof.

In alternative embodiments, the photocleavable cleavable linker molecule comprises one or more selected from the group consisting of the following compounds 6-10, any derivatives thereof, and any combinations thereof:

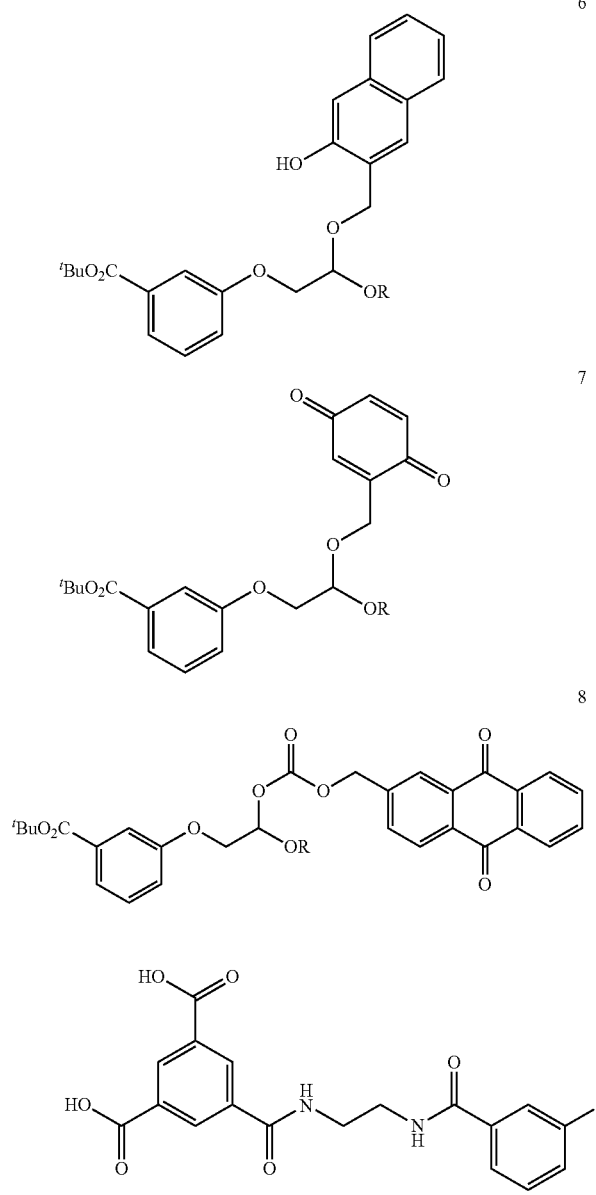

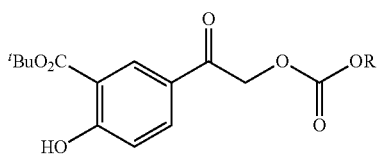

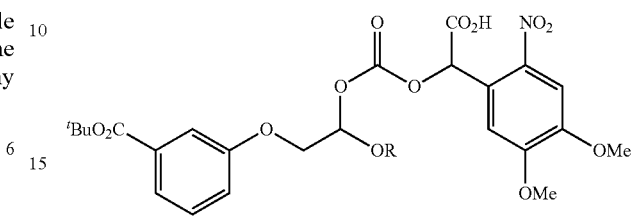

In some other embodiments, a number of an alkyl group, an oxy alkyl group, an alcohol group, a carboxyl group, an amine group, am amide group, an aromatic group, and a naphthalene group, any derivatives thereof, and any combinations thereof in the linear or branched chain of the linker is 1 to 1000.

In still some other embodiments, the linker molecule or the high charge mass moiety in the reporter composition is configured not to affect nucleotide polymerization by a polymerase.

In still some other embodiments, the high charge mass moiety in the reporter composition is configured to extend out from a nucleotide polymerase complex.

In still some other embodiments, the linker molecule or the high charge mass moiety in the reporter composition is configured to protrude out from a nascent chain so as to reach-down toward the sensitive detection nanostructure or sensor.

In still some other embodiments, a net charge mass of the high charge mass moiety in the reporter composition is positive or negative, or is variable depending on pH.

In still some other embodiments, a net charge mass of the high charge mass moiety in the reporter composition is positive in turn in an acidic pH.

In still some other embodiments, a net charge mass of the high charge mass moiety in the reporter composition is negative in turn in an alkaline pH.

In still some other embodiments, the linker molecule and/or the high charge mass moiety in the reporter composition is configured to be removable.

In still some other embodiments, the reporter composition comprises one or more selected from the group consisting of the following compounds, any derivatives thereof, and any combinations thereof:

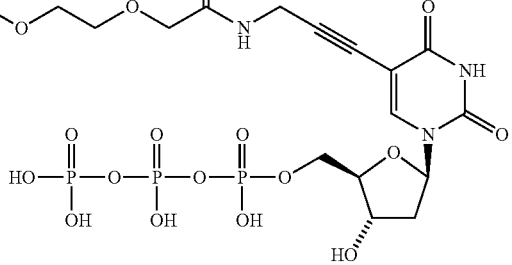

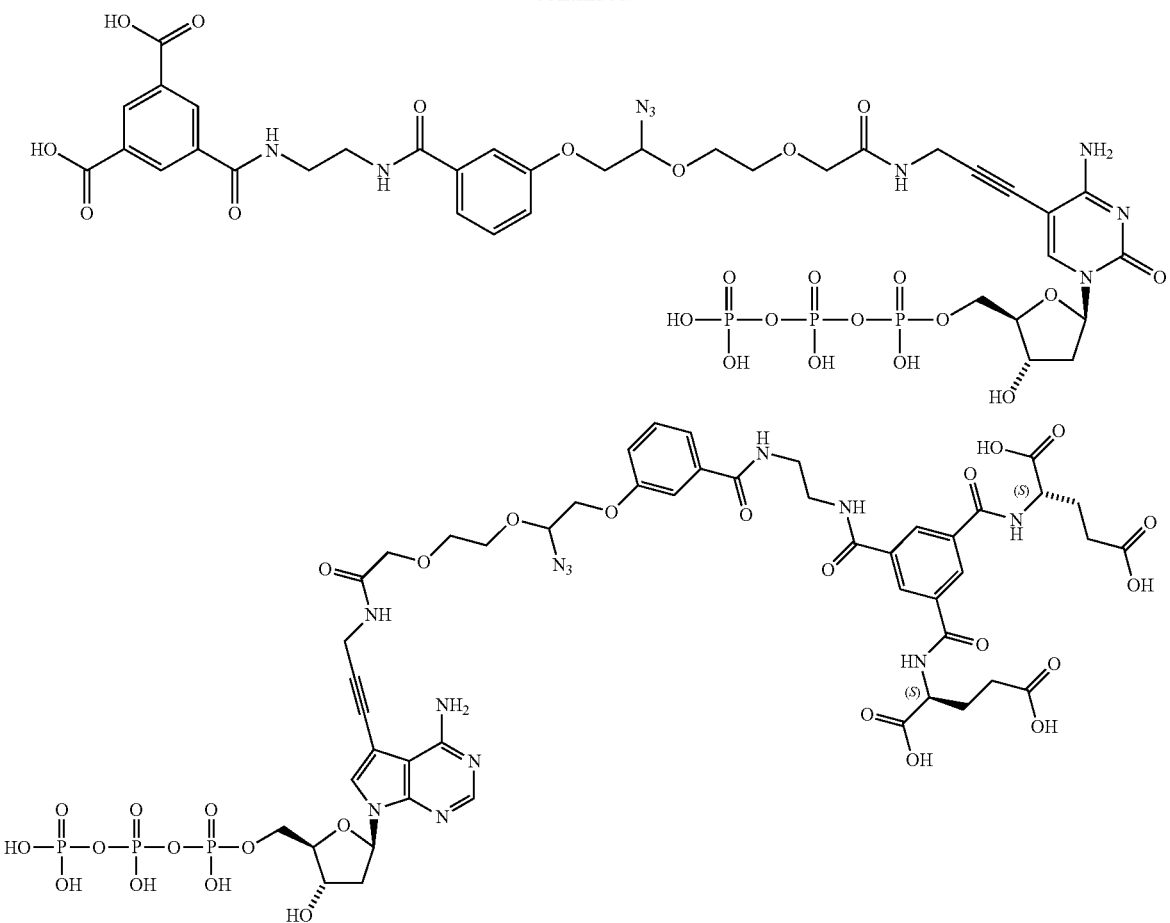
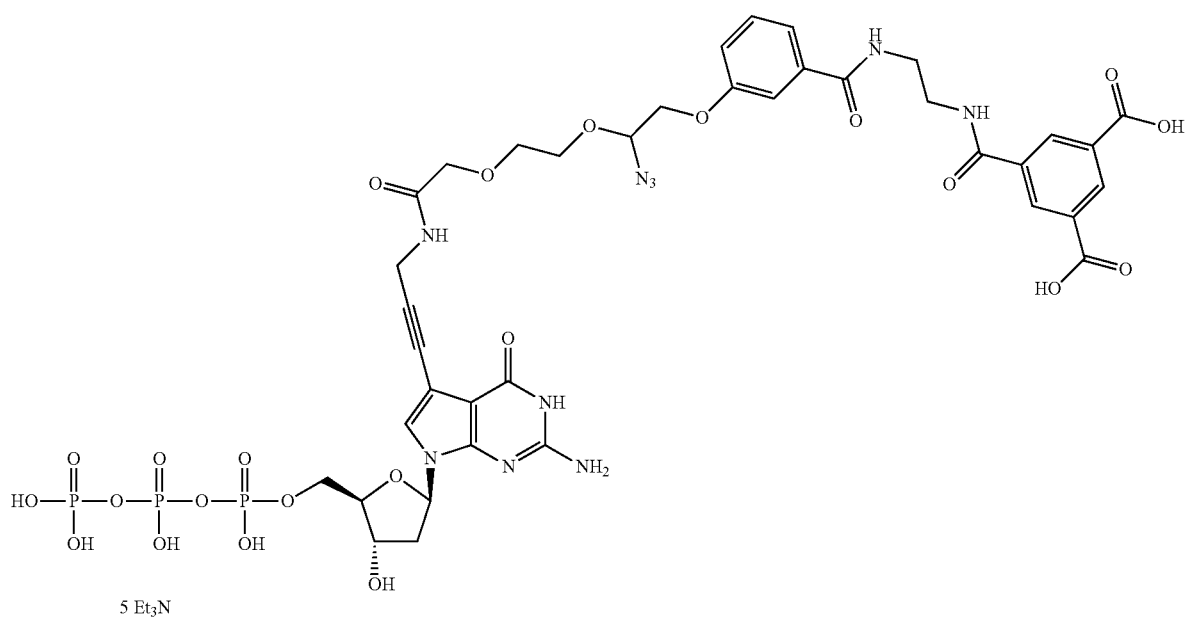

-continued

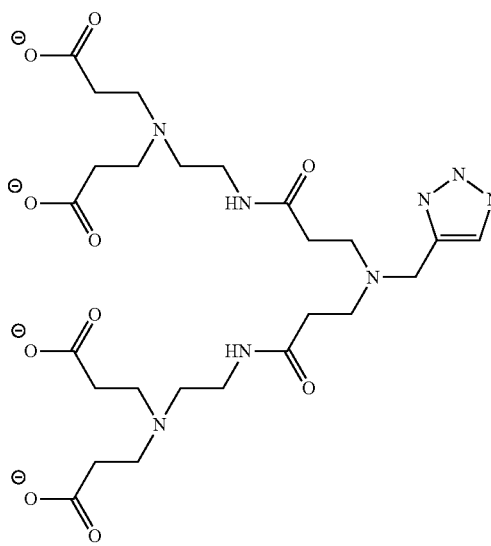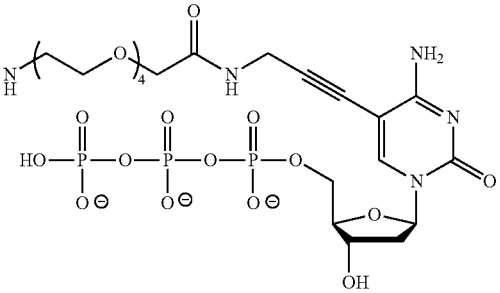

In addition, a kit for determining a nucleotide sequence, comprising the reporter composition in any of the embodiments discussed above is also disclosed in accordance with embodiments of the present invention.

Also, a method of synthesizing the reporter composition in any of the embodiments discussed above is also disclosed. The method may comprise generating a first covalent linkage between the nucleotide and a first functional group of the linker, wherein a phosphate group, a sugar or a base of the nucleotide is linked to the first functional group of the linker, and generating a second covalent linkage between a second functional group of the linker and any functional group present in the high charge mass moiety.

In some embodiments of the method of synthesizing the reporter composition, the nucleotide comprises a triphosphate group, selected from the group consisting of adenosine triphosphate (ATP), guanosine triphosphate (GTP), cytidine triphosphate (CTP), thymidine triphosphate (TTP), and uridine triphosphate (UTP). In some other embodiments, the phosphate group of the nucleotide comprises thiophosphate or phosphoramidate.

BRIEF DESCRIPTION OF DRAWINGS

The patent or application filed contains at least one drawing executed in color. Copies of this patent or patent application publication with color drawings will be provided by the Office upon request and payment of the necessary fee.

FIG. 3A shows results from a primer extension assay and FIG. 3B shows results from a melt analysis.

DETAILED DESCRIPTION OF CERTAIN EMBODIMENTS

Figure 1:
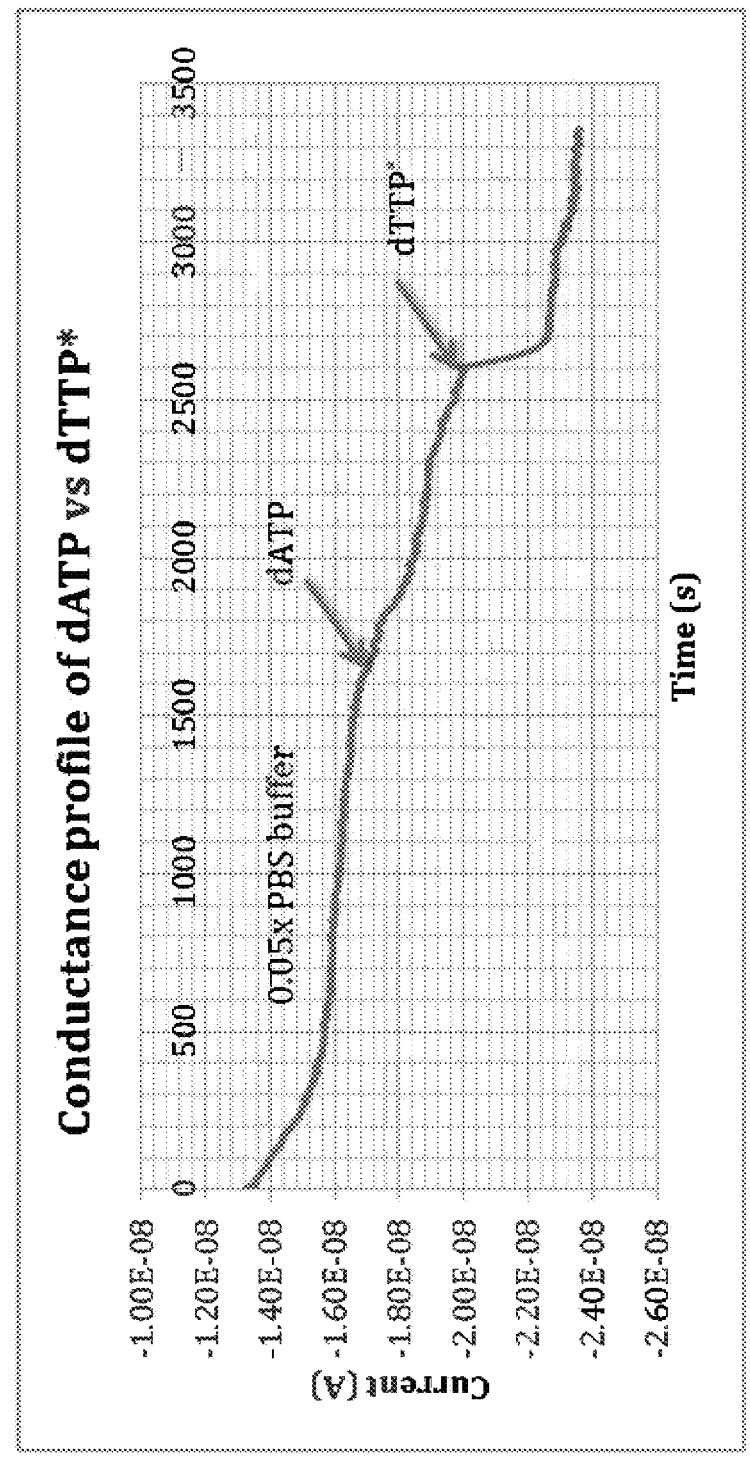
FIG. 1 shows a plot current over time of nanowire response to buffer, dATP (deoxyandenosinetriphosphate) and dTTP* (deoxythymidinetriphosphate).

The sequencing of the human genome and the subsequent studies have since demonstrated the great value in knowing the sequence of a person's DNA. The information obtained by genomic DNA sequence analysis can provide information about an individual's relative risk of developing certain diseases (such as breast cancer and the BRCA 1&2 genes). Furthermore, the analysis of DNA from tumors can provide information about stage and grading.

Infectious diseases, such as those caused by viruses or bacteria also carry their genetic information in nucleotide polymer genomes (either DNA or RNA). Many of these have now been sequenced, (or enough of their genome sequenced to allow for a diagnostic test to be produced) and the analysis of infectious disease genomes from clinical samples (a field called molecular diagnostics) has become one of important methods of sensitively and specifically diagnosing disease.

Measurements of the presence or absence, as well as the abundance of mRNA species in samples can provide information about the health status of individuals, the disease stage, prognosis and pharmacogenetic and pharmacogenomic information. These expression arrays are fast becoming tools in the fight against complex disease and may gain in popularity as prices begin to fall.

In short, the analysis of nucleotide polymers (DNA & RNA) has become important in the clinical routine, however, cost remains a barrier to widespread global adoption. One reason for this is the complexity of the analysis requiring expensive devices that are able to sensitively measure up to four different fluorescence channels as RT-PCR experiments progress. The cheaper alternatives may require skilled technicians to run and interpret low-tech equipment, such as electrophoresis gels, but this too may be expensive and a lack of skilled technicians in developing countries is prohibitive.

To solve this, a method of nucleotide polymer analysis that may require cheap and easy to use devices may be required. Some embodiments of the present disclosure describes chemical reagents, synthetic nucleotides, that can generally be utilized in such devices. Various embodiments used in connection with of the present disclosure describes novel synthetic nucleotides that comprises at least some standard nucleotides (or any modifications, or isoforms), with a high negative charge mass reporter moiety attached via a linker molecule (for instance, attached to the 5' phosphate group), with the linker length of such a length so as to protrude from a polymerase complex during polymerization, so as not to cause a significant deleterious effect on the polymerase's action.

As used in various embodiments herein, a nucleotide can be, but not limited to, one of the following compounds, Adenine, Guanine, Cytosine, Thymine, Uracil, and Inosine as well as any modified nucleotides, any nucleotide derivatives and any degenerate base nucleotides. Some non-limiting examples of such nucleotide may comprise a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof. Furthermore, single stranded deoxyribose nucleic acid (ssDNA) can generally be a single stranded nucleotide polymer molecule, comprising Nucleotides and double stranded deoxyribose nucleic acid (dsDNA) can generally be a double strand comprising two ssDNA molecules linked together via, for example, hydrogen bonding, in a reverse complimentary orientation.

Nucleotides can generally be synthesized through a variety of methods both in vitro and in vivo. This can involve salvage synthesis (the re-use of parts of nucleotides in resynthesizing new nucleotides through breakdown and synthesis reactions in order to exchange useful parts), or the use of protecting groups in a laboratory. In the latter case, a purified nucleoside or nucleobase can be protected to create a phosphoramidite, and can be used to obtain analogues not present in nature and/or to create an oligonucleotide.

In some embodiments, nucleotide synthesis comprises the formation of a nucleoside (the nitrogenous base joined to a sugar). The sugar involved in the synthesis and structure of a nucleotide may be either ribose or deoxyribose; in the latter case, the prefix 'deoxy' may be added before the name of the nucleoside in all cases except Uracil. A functional group of phosphate can be then esterified to the sugar, creating a nucleotide. The phosphate group may comprise one, two, or three phosphates, forming mono-phosphates, di-phosphates, or tri-phosphates, respectively.

Some other embodiments of the present disclosure describe the design, synthesis and use of special synthetic nucleotides comprising a nucleotide and a reporter moiety, in which the reporter moiety may not act as a polymerase enzyme blocking moiety attached via a linker.

A reporter moiety or reporter composition used in various embodiments in connection with the present inventions is a molecule or molecules that are easily detected by a biosensor or other detection method (such as by eye) and are attached to biomolecules, or probes, or primers that detect or amplify molecules of interest.

A linker molecule used in various embodiments is a polymer made up of more than one subunit that links a reporter molecule to a nucleotide. An example of a linker molecule is a Di-amine linker $H_2N-L-NH_2$, where L represents a number of further subunits.

As such, the present disclosure should be considered to include all configurations that include any nucleotide or its derivative with a linker molecule attaching a reporter moiety with an overall high charge, sufficient enough to get a detectable change in a sensitive biosensor that can detect small variations in charge mass at or near its surface. Accordingly several examples presented in this application are presented only for the purpose of illustration and should not be considered to limit the scope of the invention.

In various embodiments, the synthetic nucleotides can have at least some of the following aspects:
1. The reporter moieties reports based upon its charge mass, not enzymatic activity, fluorescence etc;
2. Each synthetic nucleotide may either carry the same charge mass reporter moiety, or carry a different charge mass;
3. The reporter moieties may be easily cleaved; and/or
4. The nucleotides may be cheaply and easily mass synthesized.

There are several possible positions available for the attachment of linkers and the reporter moieties. It is important to attach the linker so as to not interfere with polymerization or hydrogen bonding between the bases of nucleotides when hybridizing with its compliment base in another nucleotide polymer (i.e. when two strands of reverse compliment DNA hybridize to form a double stranded DNA molecule), One possible position can be the phosphate linkage in the nucleotide. Furthermore, by attaching the linker to the 5' position in the phosphate, it will block further nucleotide additions as it will prevent phosphodiester bond formation.

Another possible positions available for the attachment of linkers and the reporter moieties, is on either the sugar group or the base group.

Some other embodiments describe methods of the use in which the linker and reporter moiety can be cleaved from the synthetic nucleotide in the iterative manner after detection. As one of the possible places to attach the linker is the 5'-phosphate end of phosphate group, which will prevent further nucleotide additions then, by cleaving the linker will therefore remove this block and allow for further nucleotide additions.

As way of an example, there are at least two options available which could facilitate synthesis at the 5'-phosphate terminal:
1. Thiophosphate; and/or
2. Phosphoramidate.

The proposed linker therefore can have the following structure at least in some embodiments:

where, L could be, but is not limited to, any linear or branched chain molecule that is configured to link to a nucleotide as well as a high charge mass moiety, both of which are present in a synthetic nucleotide. In some embodiments, L comprises a plurality of an alkyl group, an oxy alkyl group or the combination thereof with various lengths. In one embodiment, the number of an alkyl group, an oxy alkyl group or the combination thereof in L is 1 to 100. In another embodiment, the number of an alkyl group, an oxy alkyl group or the combination thereof in L is 1 to 75. In still another embodiment, the number of an alkyl group, an oxy alkyl group or the combination thereof in L is 1 to 50. In still embodiment, the number of an alkyl group, an oxy alkyl group or the combination thereof in L is 1 to 25. In some other embodiments, the number of an alkyl group, an oxy alkyl group and the combination thereof in L can be more than 100. While $NH_2$ is presented for the purpose of illustration, this $NH_2$ can be substituted with any other function group that can be cross-linked to a nucleotide or its derivative as well as a high charge mass moiety, both of which are present in a synthetic nucleotide. Some illustrative examples that can be used instead of $NH_2$ include, but not limited to, any alkyl group (e.g. $C_nH_{2n+1}$, wherein n represents a positive integer number such as 1, 2, 3, and etc), any alcohol group (e.g. $C_nH_{2n}OH$, wherein n represents a positive integer number such as 1, 2, 3, and etc), any carboxyl group (e.g. COOH), any amide group (e.g. CONH), and any derivatives thereof. As the linker molecules can vary in length and chemical structure in part to enable the reporter moiety to extend out from a nucleotide polymerase (e.g. DNA polymerase, RNA polymerase and others) complex so that some aspects of polymerization may not be influenced entirely or partially The easy access to the linkers of various lengths can be considered as a benefit in a situation where the desired length of the linker may not be known completely or partially. This may make the optimization experiments easy.

The linker with the nucleotide (say Adenosine as an illustrative example) therefore may have the following structure at least in some embodiments. While adenosine is 2. Pentanediamine (5 carbon bond length separation)

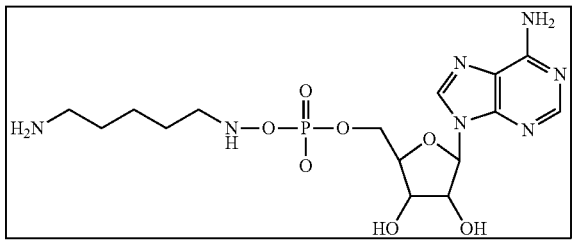

3. Length equivalent to 13 carbon bond length separation

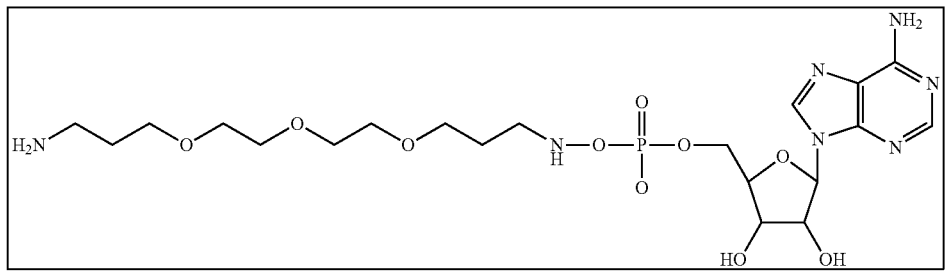

presented in some examples below, this adenosine can be substituted with any other natural or synthetic nucleotide, any modifications thereof and any derivatives thereof in some other embodiments.

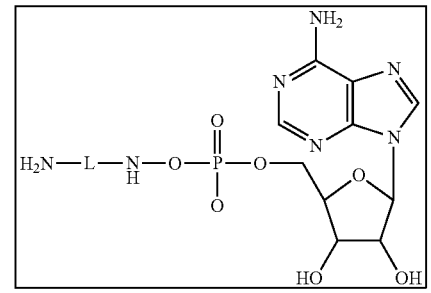

In some embodiments, various lengths of linkers at this position may have the following structures (exemplified with the Adenosine):

1. Ethylenediamine (2 carbon bond length separation)

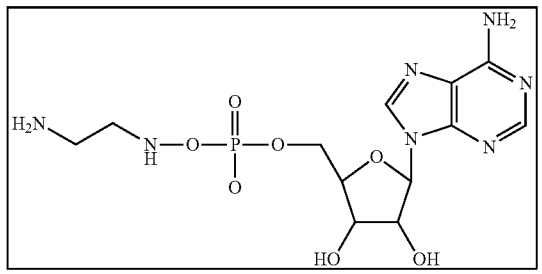 [SMILES: NCCNOP(=O)(O)OCC1OC(n2cnc3c(N)ncnc32)C(O)C1O]

Thus in some embodiments, the linkers thus selected can be:
  1. Easily available;
  2. Easy to link and cleave (please refer the probable protocols below); and/or
  3. Not to interact with the polymerase and the polynucleic acid strand and/or not affect nucleotide polymerization and growth of a nascent nucleotide polymer.

The reporter moiety: As used herein a "reporter moiety" is a molecule or molecules that are easily detected by a biosensor or other detection method (such as by eye) and are attached to biomolecules, or probes, or primers that detect or amplify molecules of interest that are normally difficult to detect without the presence of the reporter moiety 'reporting' on its presence. The reporter moieties can be any charged molecule, group of charged molecules and even many charged molecules arranged dendritically. The reporting mode is their charge, which is detected by sensitive charge detection biosensors, such as nanowire/nanotube FETS, nanopores and other piezoelectric biosensors. In some embodiments, the reporter moieties can be associated with the other properties like the chromophoric nature for enabling their detection by UV or visible detector or the fluorescent nature making them to be detected by the fluorimetric detection. Furthermore, the mass of the reporter moiety can be exploited using biosensors that can detect mass, such a surface Plasmon resonance biosensors and cantalivers.

The charge on the reporter: certain embodiments of the present invention describe the reporter moiety to carry a large charge mass. In one embodiment, the reporter moiety may introduce a higher charge mass to the synthetic nucleotide than the charge mass of the nucleotide or its derivative, which is present in the synthetic nucleotide. However, in another embodiment, the charge mass introduced by the reporter moiety can be substantially equal to or less than the charge mass of the nucleotide or its derivative, which is present in the synthetic nucleotide. Some non-limiting and illustrative examples of a reporter moiety are provided in this specification. These examples are provided only for the illustration purpose and therefore should not be considered to limit the scope of the invention. The chemical structure and/or dimension (e.g. length, size, and mass of a molecule used as a reporter moiety) of a reporter moiety may not be restricted as long as the reporter moiety is configured to provide a charge mass to the synthetic nucleotide and also not to affect polymerization reaction of nucleotides partially or entirely.

The charge on the moiety can be positive or negative. Taking into consideration the nature of linkage, the following provides some aspects of the selection of charge that can be possibly used in some embodiments of the present disclosure.

In some embodiments, a reporter moiety having a high charge mass, thereby also identified as a high charge mass moiety, may comprise an aromatic or aliphatic skeleton, comprising one or more charged groups selected from the group consisting of a tertiary amino group, a carboxyl group, a hydroxyl group, a phosphate group, a phenolic hydroxy group, any derivatives thereof, and any combinations thereof, wherein the one or more charged groups comprise a charge mass that is sufficient to change a property of a sensitive detection nanostructure or nano/micro-sensor operably coupled to the reporter composition.

Positive charge: In some embodiments, the large number of positive charges can generally be induced on the reporter moiety through the incorporation of tertiary amino groups on the aromatic or aliphatic skeleton. In such embodiments, in turn in the acidic pH (less than 7), these groups may acquire the positive charges making them detectable.

Negative charges: In some other embodiments, the negative charges can generally be induced on the reporter moiety through the incorporation of a carboxyl group, a hydroxyl group, a phosphate group, an alcohol hydroxyl group and/or a phenolic hydroxy group (or functionality) on the aromatic or aliphatic skeleton. Given below are some of the proposed reporter moieties which meet the above mentioned criteria. The fragments listed below may be available and able to link to the linker through the amino terminal. The additional advantage could be that the reagents that are proposed for the phosphoramidate linkage formation may be the same as this amide linkage formation (Therefore reducing costs of the system further).

Moreover, at least in part due to the stability of this linkage to the alkaline pH (above 7), the process of induction of negative charge would be of no or substantially small interference.

For the purpose of illustration, the following three non-limiting examples are presented. These examples are provided only for the purpose of illustration and therefore should not be considered to limit the scope of the invention. As such, any modifications on the following examples are certainly included in the scope of the invention. For example, any substitution of one or more groups (e.g. —OH, =O, COOH, and others) linked to the examples can be practiced. Also oligomerization or polymerization of one of more of the following examples can also be permitted. Further any other chemical structure or molecule with various dimensions (e.g. length, size, and mass of the reporter moiety) can be used as a reporter moiety if such chemical structure or molecule is configured to provide a charged mass to the synthetic nucleotide and also not to affect polymerization reaction of nucleotides partially or entirely.

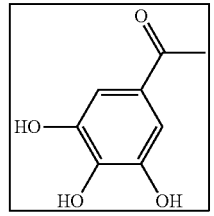

Reporter-1

Potential charge—3

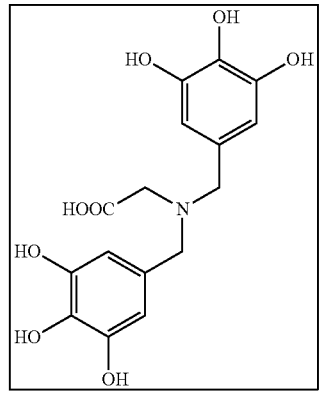

Reporter-2

Potential charge—6

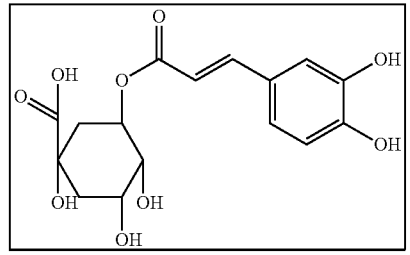

Reporter-3

Potential charge—5

After acquiring the charges, some of these reporters in certain embodiments may exist as follows,

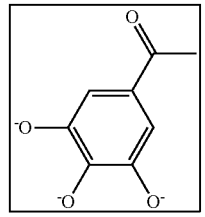

Reporter-1

Potential charge—3

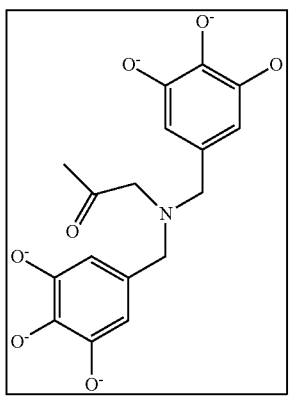

Reporter-2

Potential charge—6

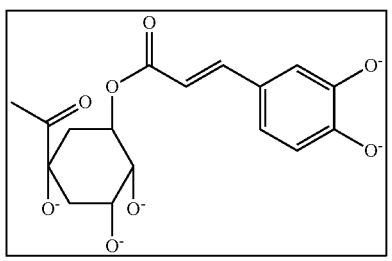

Reporter-3

Potential charge—5 whereas, the reporter-1 and reporter-3 may be available on shelf, reporter-2 may be custom synthesized.

The reporter moieties proposed can generally (be) thus:
1. Easily available or synthesizable;
2. Bear a large charge;
3. Not costly; and/or
4. Easy to link and cleave.

Final compounds (monomers): Based on the above propositions, the final structures of the nucleotides along with the linkers and the reporters would be as follows at least in certain parts of embodiments. The following examples of some final compounds are also provided for the purpose of illustration and therefore should not be considered to limit the scope of the invention. As described above, any variations permitted for a nucleotide or its derivative, a linker and a high charge mass reporter moiety are also permitted to a final compound. Thus, for the adenosine as a nucleotide at the 5'-phosphate terminal in some examples, if the linker is, say, C 13 equivalent (option 3 above), the various linkers would make the final structures looks as below:

One proposed final synthetic nucleotide-1 (note the reporter is in monomer form and this can be increased by aggregating these monomers to increase charge mass as required):

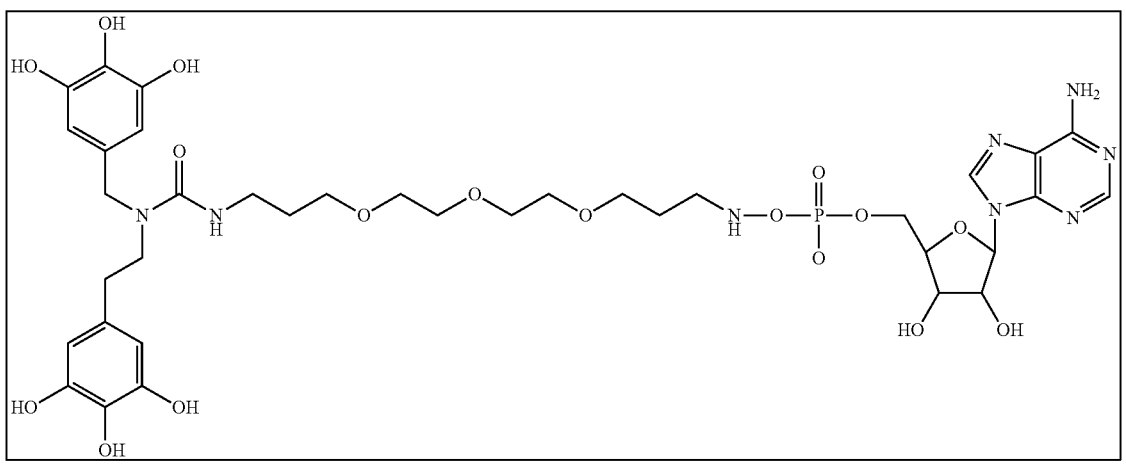 [SMILES: Nc1ncnc2c1ncn2C1OC(COP(=O)(O)ONCCCOCCOCCOCCCNC(=O)N(CCc2cc(O)c(O)c(O)c2)Cc2cc(O)c(O)c(O)c2)C(O)C1O]

Another proposed synthetic nucleotide-2 (note the reporter is in monomer form and this can be increased by aggregating these monomers to increase charge mass as required):

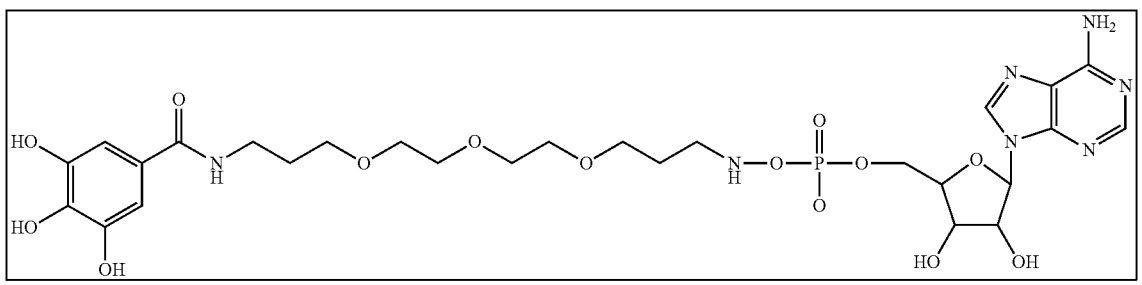 [SMILES: Nc1ncnc2c1ncn2C1OC(COP(=O)(O)ONCCCOCCOCCOCCCNC(=O)c2cc(O)c(O)c(O)c2)C(O)C1O]

Still another proposed synthetic nucleotide-3 (note the reporter is in monomer form and this can be increased by aggregating these monomers to increase charge mass as required):

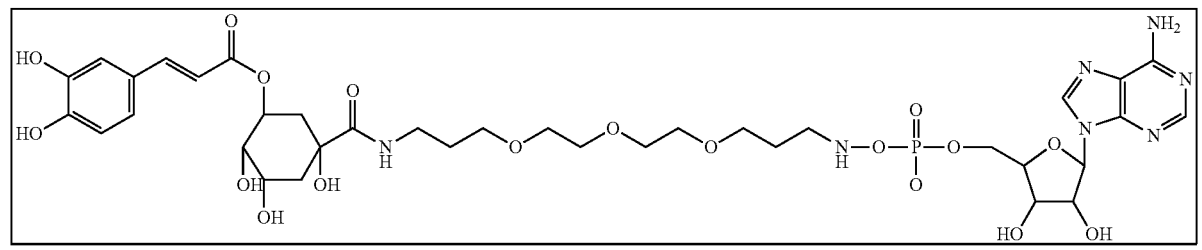 [SMILES: Nc1ncnc2c1ncn2C1OC(COP(=O)(O)ONCCCOCCOCCOCCCNC(=O)C2(O)CC(O)C(O)C(OC(=O)/C=C/c3ccc(O)c(O)c3)C2)C(O)C1O]

The following is a non-limiting, illustrative example of synthesis protocols used in at least some embodiments:

1. Synthesis of 5'-phosphoramidates of Adenosine: (Linkage of Nucleotide with the diamine linker). Method of Chu et. al. can be used for synthesizing 5'-amino derivatives of adenosine phosphoramidate in which diamantes and adenosine monophosphate (AMP) can be dissolved in water. EDAC was added later on and was incubated at room temperature with constant stirring. The reaction was monitored till completion.
2. Synthesis of Final proposed structures: (Linkage of the diamine linker with reporter moiety). Method of Chu et. al. can be used for synthesizing 5'-amino derivatives of adenosine phosphoramidate in which diamines and adenosine monophosphate (AMP) can be dissolved in water. EDAC was added later on and then incubated at room temperature with constant stirring. The reaction was monitored till completion.

One advantage of the similar procedure is that it may work out for both the steps leading to the formation of final compounds as monomers.

In some illustrative examples of some embodiments, (see below) cleavage of the linkers and reporter moieties may need to be done. The linkages like phosphoramidates can generally be rather readily cleaved by the use of acids like trifluoroacetic acid at an ambient temperature. By way of an illustrative example, the proposed synthetic nucleotide-2 demonstrated as a probable 3D view below. The aromatic ring at the bottom left of the molecule bears three hydroxy functions which could potentially get converted to the negative charge under slight alkaline conditions. Following is the 3D conformation of the adenosine attached with the Reporter-1 through linker 3 and the related data.

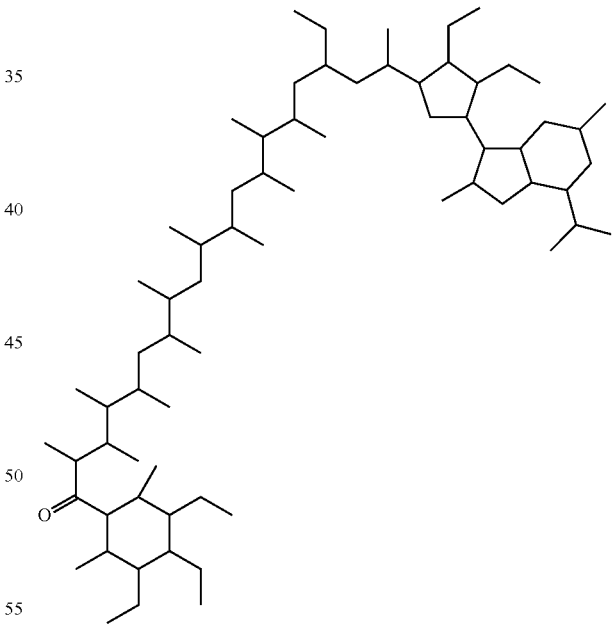

Approximate distance between the phosphoramidate and terminal charged atom may be about 20 angstroms, which could generally be sufficient to induce the charge potential in the surface for detection. This distance can further be altered with the further modifications in the phase at least in part by changing the linker lengths. The charge on the terminal reporter moieties can also be changed by the variations in the chemistry of reporter moieties.

In one embodiment, the reporter composition recited in the appended claims comprises any nucleotide with a cleavable linker molecule attached to a high charge mass moiety, wherein the synthetic nucleotide (otherwise referred to as the reporter composition) has a charge that is sufficient to cause a detectable change in the property of a sensitive detection nanostructure or nano/micro-sensor, when the reporter composition is operably coupled to the nanostructure (as for example, by addition of the synthetic nucleotide (reporter composition) to a nascent chain during a sequencing by synthesis procedure).

In some embodiments, sequencing reactions can be tracked through monitoring changing electrical properties of nanowires throughout primer extension. In such an instance, each nucleotide is then added one after another and the conductance of the nanowires monitored. When the conductance changes sufficiently (e.g., the change in conductance is detectable) then a nucleotide has been incorporated into the nascent chain.

In certain embodiments, sequencing reactions may utilize a reporter composition, e.g., comprising: a nucleotide or its derivative, a high charge mass moiety comprising an aromatic or aliphatic skeleton, comprising one or more charged groups selected from the group consisting of a tertiary amino group, a carboxyl group, a hydroxyl group, a phosphate group, a phenolic hydroxy group, any derivatives thereof, and any combinations thereof, wherein the one or more charged groups comprise a charge mass that is sufficient to change a property of a sensitive detection nanostructure or nano-/micro-sensor operably coupled to the reporter composition, and a linker molecule attached to the nucleotide or its derivative and the high charge mass moiety, wherein the linker molecule comprises a linear or branched chain comprising one or more selected from the group consisting of an alkyl group, an oxy alkyl group, an alcohol group, a carboxyl group, an amine group, am amide group, an aromatic group, and a naphthalene group, any derivatives thereof, and any combinations thereof.

In certain embodiments, it is configured to detect the addition of individual nucleotides by sensing electrical charge associated with a reporter moiety using a nanostructure that is capable of detecting a change in electrical charge density (e.g., by detecting a change in resistance). In some of such embodiments, a charged moiety (or a reporter moiety) has an electrical charge that is sufficient to change an electrical property of a sensitive nanostructure, when the reporter composition is operably coupled to the sensitive nanostructure. For example, when a new nucleotide that may contain a reporter composition is added to the growing polymer in a sequencing by synthesis reaction, the charge density at, or near the surface of the sensitive nanostructure increases, and this can be detected by a change in property in the sensitive detection nanostructure or nano-/micro-sensor. More particularly, if using a nanowire as the detecting structure, at least in some embodiments, an increase in charge caused by the addition of the reporter (having a charged moiety) may be detected by a change in resistance in the wire, due to a phenomenon called the field effect. In other words, at least in some embodiments, the claimed reporter composition, by virtue of its high electrical charge, is capable when coupled to a sensitive detection nanostructure or nano-/micro-sensor, of causing an electrical change (resistance) in the sensitive detection nanostructure or nano-/micro-sensor. In the detection of a change in resistance, e.g. a change in electrical charge at or near the surface of the sensitive nanostructure or sensor, or an innate electrical charge added by the newly added nucleotide at or near the surface of the sensitive nanostructure or sensor, the distance of which is dependant on mode of device operation and gate dielectric/fluid interface and for field effect transistors (FET) falls within a range of 0-100 nm based on the charge neutralization of oppositely charged species cancelling out the effect of Coulombic interactions beyond that range—although, as would be well understood by one skilled in the art, for other indirect detection methods the range may differ) by the sensitive detection may occur therefore when the new nucleotide is added to a growing chain of the nucleotide sequence to be sequenced that is located at or near the surface of the sensitive nanostructure. In certain alternative embodiments, the distance may be a function of a biosensor in use. Thus, for instance, if the biosensor is a field effect transistor, it could be dependent on a solution and the field effect transistor sensor, and in some of certain cases, the distance can be within a micron of the sensor or within the sensing ragen of the sensor. The detection of a change in resistance can be measured to determine the identity of the newly added nucleotide. In other words, in some embodiments, such a detection does not require any additional step, before or after the addition of the new nucleotide, such as removing the previously added one or more nucleotide from the growing chain of the nucleotide sequence (or from the reaction zone), removing a compound blocking the addition of the new nucleotide to the growing chain of the nucleotide sequence, and/or converting a chemical and/or physical property of the newly added nucleotide(s). Therefore, in some embodiments, the detection can occur instantly or substantially immediately after the new nucleotide is added to the reaction zone (or the growing chain of the nucleotide sequence). However, in some alternative embodiments, any additional step, before or after the addition of the new nucleotide could occur, e.g. removing the previously added one or more nucleotide from the growing chain of the nucleotide sequence (or from the reaction zone), removing a compound blocking the addition of the new nucleotide to the growing chain of the nucleotide sequence, and/or converting a chemical and/or physical property of the newly added nucleotide(s).

In certain embodiments, one or more derivatives of any of the compositions or compounds disclosed in this application may be utilized. In some of such embodiments, the derivatives may comprise the compounds having the same or substantially the same functionality (or activity) compared to its respective original compounds and having one or more substitutions in any of elements (e.g. C, O, N, H and more), any of functional groups (e.g. —OH, =O, —N$_3$, —NO$_2$, —COOH, —CH$_3$, and more), and any parts of the skeleton or branches of the compounds. An example of such a derivative can be but is not limited to combining reporter compositions 1 and 4 shown below in a range of combinations:

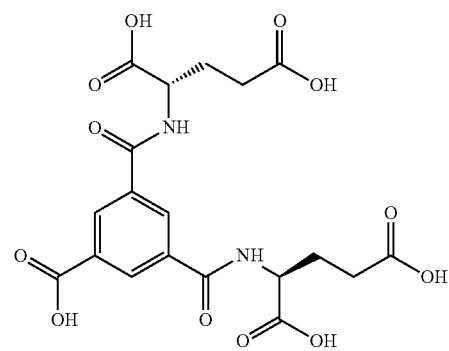 [SMILES: O=C(O)CC[C@H](NC(=O)c1cc(C(=O)O)cc(C(=O)N[C@@H](CCC(=O)O)C(=O)O)c1)C(=O)O]

The supercharged nucleotides may have a reporter moiety added to them via a linker. The linker length and nature can vary, while reporter compositions have a large negative charge. The large negative charge of the reporter moiety serves a number of functions. Some illustrative, and non-limiting examples of reporter moiety compositions (1-5) are shown below:
Reporter moieties can amplify the electronic effect of a supercharged nucleotide compared to that of an un-modified nucleotide when in close proximity to a nanowire, enabling
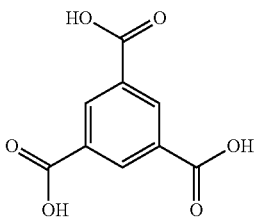
1
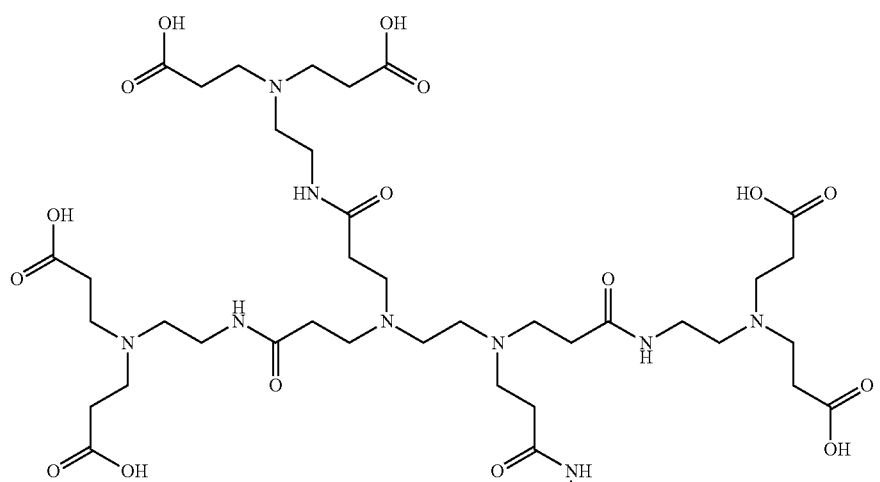
2
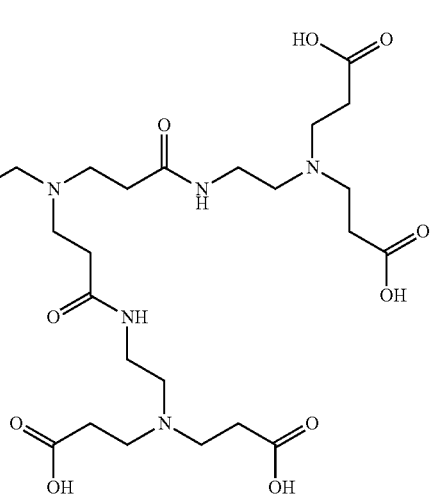
3
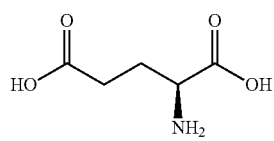
4
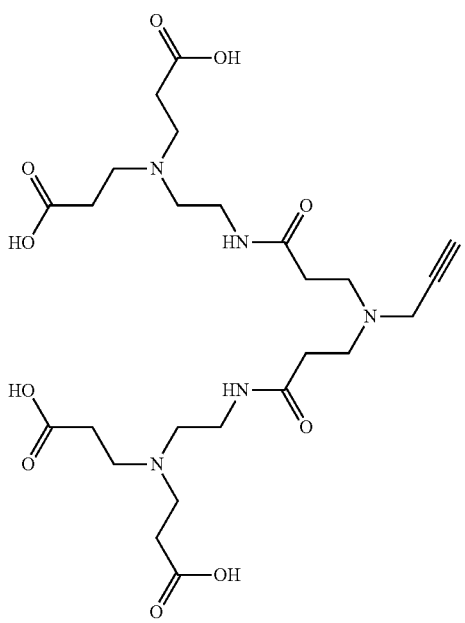
5 a particular base to be called based on the signature electronic response and it also allows for a longer read length as the charge can be detected further from the nanowire surface—nanowires can only detect charges close to their surface (the distance from the nanowire in which charge can be sensed is called the Debye length). FIG. 1 shows the relationship of current with time of nanowire response to buffer, dATP (deoxyandenosinetriphosphate) and dTTP* (deoxythymidinetriphosphate). For the results shown in FIG. 1, sensing experiments were performed by detecting the real-time conductance change of the silicon nanowires before and after dNTP (deoxyribonucleotide triphosphate) addition. The change in conductance is attributed to the introduction of the negatively charged nucleotides on the surface of the nanowires. The graph in the figure illustrates the detection of equimolar solutions (10 µM) of dATP and the supercharged dTTP, respectively, in a 0.05×PBS buffer solution. The injection of the negatively charged canonical dATP occurs at 1000 s and its detection is demonstrated with a 16% change in conductance. At 2000 s, the non-canonical supercharged dTTP is injected and the positive shift in conductance (20%) is attributed to the enhanced negative charge of the supercharged moiety associating towards the nanowire surface. These results demonstrate that it is possible to detect and differentiate between two nucleotides carrying discrete negative charges, by the change in the electrical conductance profile of the nanowires.

As the reaction proceeds, the nucleotides may be added further and further from the nanowire surface, which is where linker length may become important. And finally, the linker can serve to enable the high charge mass moiety to extend out from a DNA polymerase complex in order to avoid or minimize interference with the on-going polymerization. Some illustrative and non-limiting examples of supercharged nucleotides A, G, T and C (SCATP, SCGTP, SCTTP and SCCTP) are shown below:

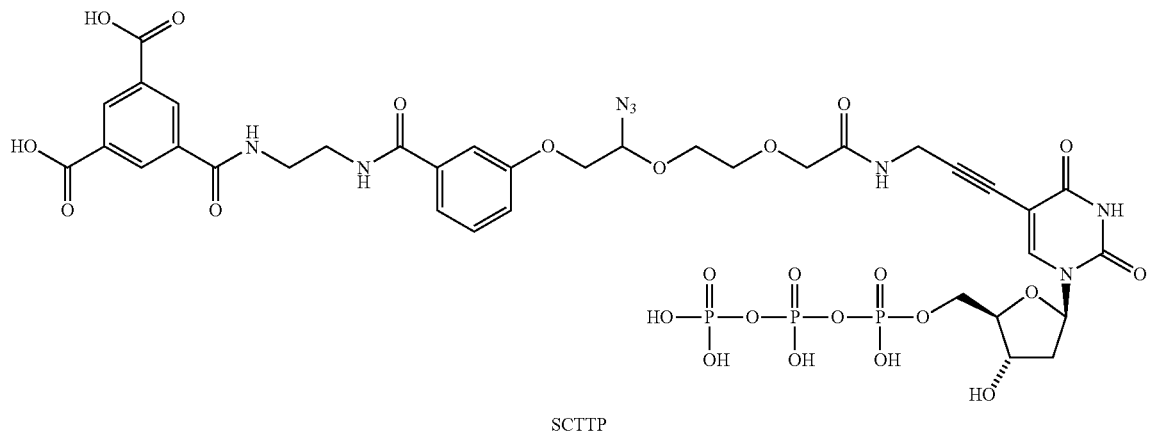

SCTTP

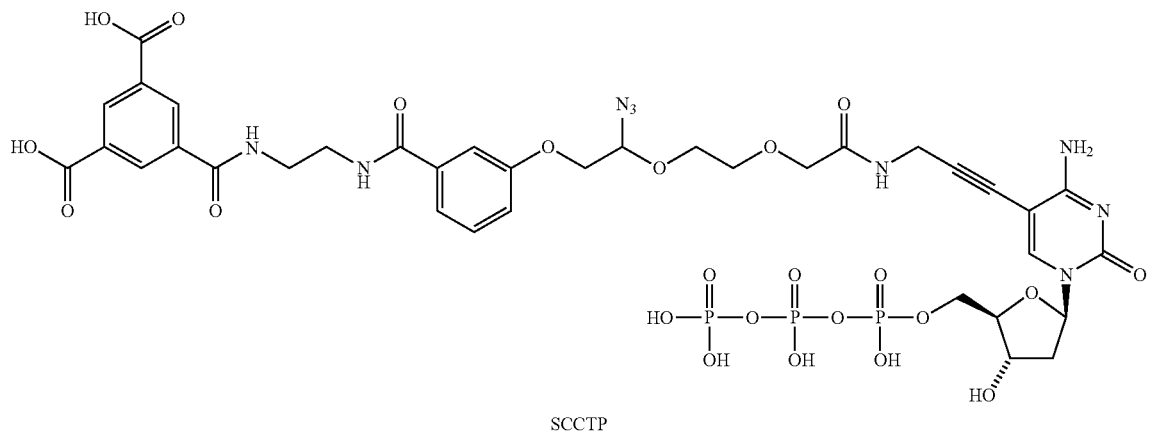

SCCTP

-continued
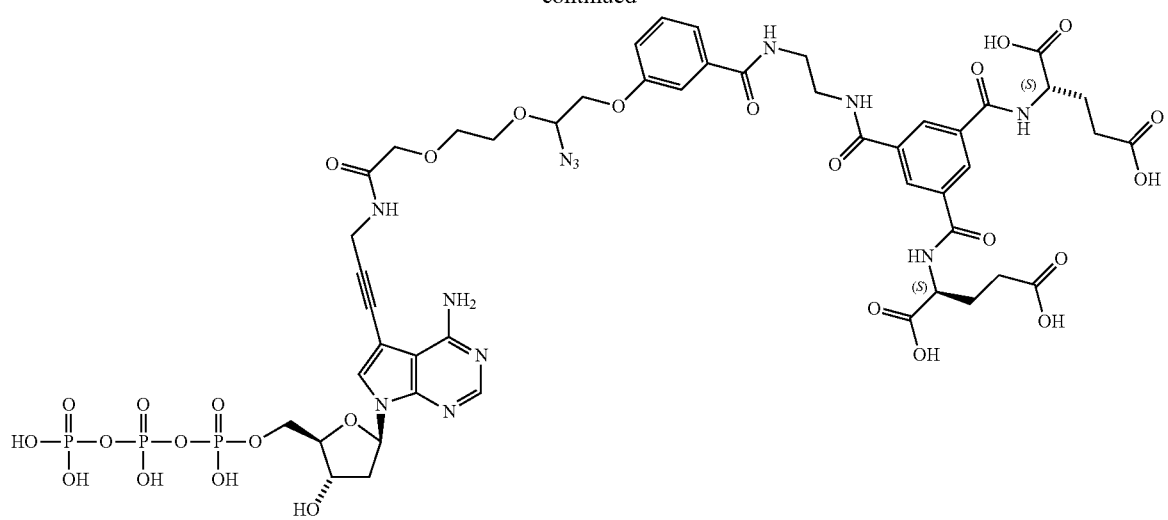
SCATP
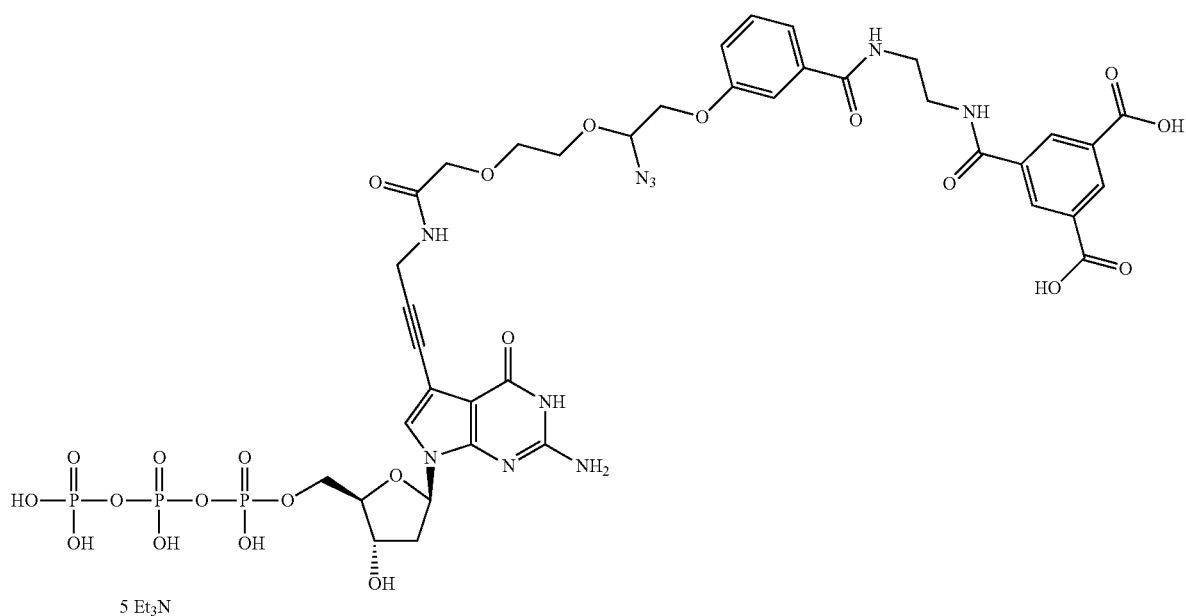
SCGTP

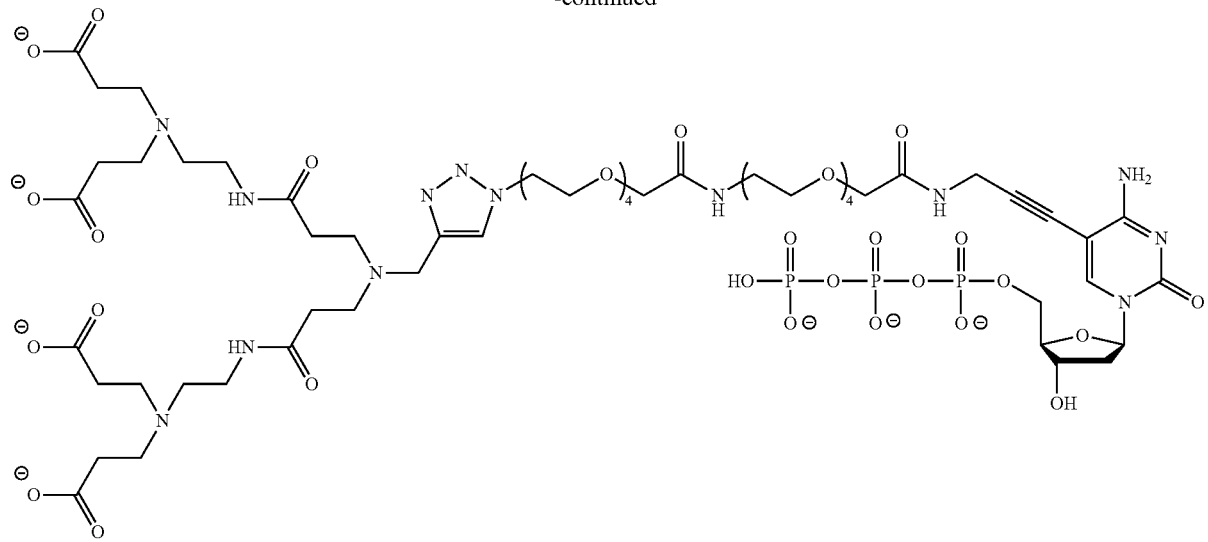

SCCTP Derivative

Once a nucleotide has been incorporated into the nascent chain, the high charged reporter moiety can be, but not necessarily, removed (cleaved) and the next synthetic nucleotide complete with a reporter moiety is incorporated. For example, there are two types of cleavable linkers sensitive to reductive conditions: disulfide bridges and azo compounds. They are efficiently and rapidly cleaved by mild reducing agents like dithiothreitol (DTT), b-mercaptoethanol or tris(2-carboxyethyl)phosphine (TCEP). Some illustrative and non-limiting examples of cleavable functionalities are shown below:

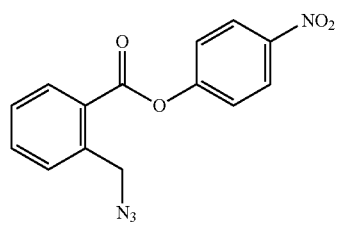 [SMILES: [N-]=[N+]=NCc1ccccc1C(=O)Oc1ccc([N+](=O)[O-])cc1]

4-Nitrophenyl 2-(azidomethyl)benzoate

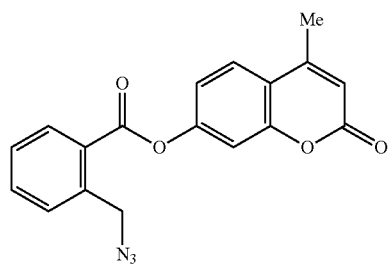 [SMILES: Cc1cc(=O)oc2cc(OC(=O)c3ccccc3CN=[N+]=[N-])ccc12]

7-Hydroxy-4-methylcoumarinyl 2-(azidomethyl)benzoate

Furthermore, numerous photoremovable protecting groups can be applicable and one of such groups includes compounds containing an ortho-nitrobenzyl motif (see, e.g. the compound no. 10 below). Known photoremovable groups, such as examples 6-10, have not been previously used in the context of nucleotides as previously describes. The photoremovable protecting group (ppg) can be efficiently removed in aqueous media by irradiation at a wavelength (e.g. 350 nm) avoiding damage to the nucleotide base.

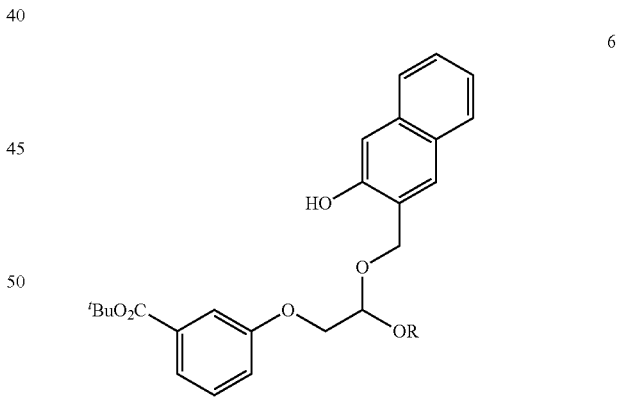

6

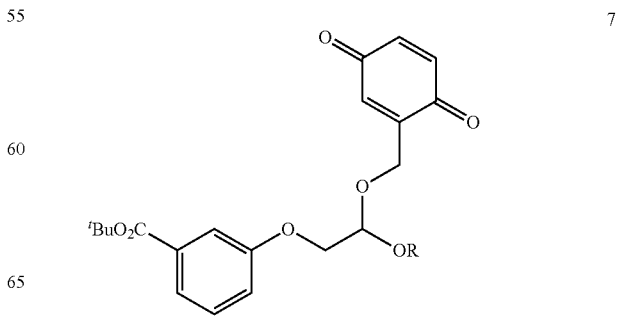

7

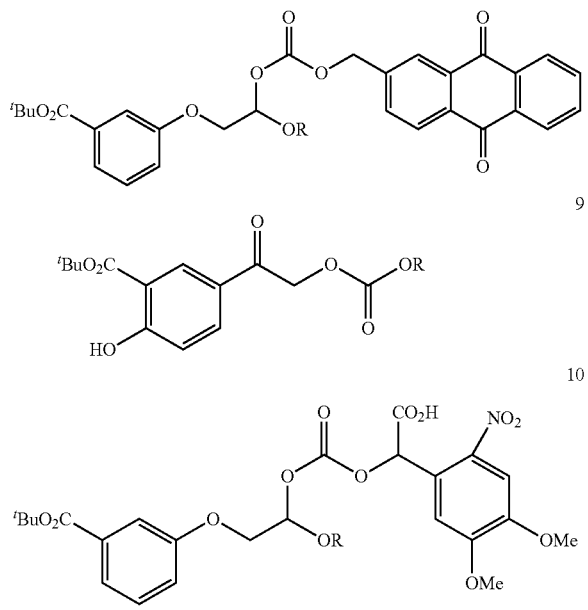

wherein, R comprises a linear or branched chain comprising of but not limited by an alkyl group, an oxy alkyl group, hydrocarbon, a hydrazone, a peptide linker, or a combination thereof.

For illustrative purpose, initial testing of 3-(hydroxymethyl)naphthalen-2-ol derivative was carried out. The molecule was dissolved in a mixture of methanol and water, and was then irradiated for 90 min with light from a mercury lamp, which emits light with a wavelength of approximately 250 nm. LCMS analysis showed 50% consumption of the starting material. After a further 90 min, there was approximately 20% starting material remaining.

Figure 2:
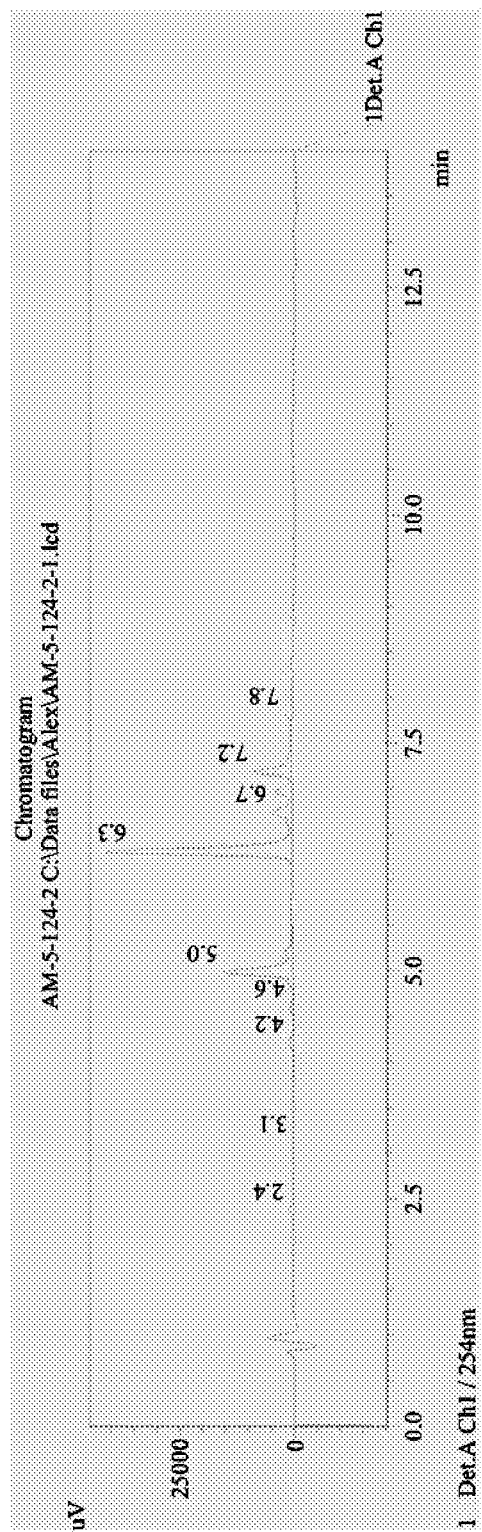
FIG. 2 shows a result from LCMS analysis done with 3-(hydroxymethyl)naphthalen-2-ol derivative.

As shown in FIG. 2, a major peak at 5 min was observed in the LCMS by UV detection, but it did not ionize in either positive or negative mode. $^1$H NMR spectroscopy showed the residual starting material along with other signals that correspond to a second benzylic group corresponding to the release of the diol. In the experiments illustrated in FIG. 2, the molecule was dissolved in a mixture of methanol and water, and was then irradiated for 90 min with light from a mercury lamp, which emits light with a wavelength of approximately 250 nm. LCMS analysis showed 50% consumption of the starting material. After a further 90 min, there was approximately 20% starting material remaining. As seen in the figure, AM-5-124-1 is after 90 mins and AM-5-124-2 is after the further 90 mins. The peak at 7.2 min is starting material and shows as m/z 404 in the MS as it is its sodium salt. The peak at 5 mins may be due to the diol being released.

As specified the linker chain can play an important role, at least in some embodiments, in enabling the nucleotide to remain a polymerase substrate, as such any modified nucleotides have to be shown to be biologically active. In order to exemplify this and as an example of certain embodiments, a polymerase reaction mix may be used for real-time primer extension analysis with Rotor Template, which requires the incorporation of a single SC-TTP nucleotide followed by a sequence of 44 dCTP, dGTP, dATP nucleotides.

Primer extension reactions were monitored using the Rotorgene Q Real-time thermocycler, this allows primer extension to be monitored fluorescently using a dsDNA intercalator (SYBR Safe) with secondary melt analysis to provide further information on product composition. This method can be used with an oligonucleotide primer/template pair designed to allow complete extension of the primer with the incorporation of a single SC-TTP nucleotide. Initially, the experiment was be conducted with a 40° C. incubation and then repeated with a 65° C. incubation (optimum synthesis temperature for most commercial DNA Polymerases). Control reactions with standard dNTPs (positive control) and no dNTPs (negative control) were included, alongside a control(s) for mis-incorporation. FIG. 3A captures the extension of the primers in the presence of standard dNTPs (yellow) and also in the reaction containing SCTTP (blue, yellow), although the maximum fluorescence intensity associated with SC-TTP (blue) incorporation is slightly reduced, indicating a slight reduction in final product concentration. Reactions lacking dTTP or DNA polymerase did not display the equivalent increase in fluorescence, indicating failure of primer extension (red amd purple). FIG. 3B shows the melt analysis and confirms the variance in end products between the negative (no polymerase, red and purple) and positive (standard dNTPs, yellow) control reactions with melt peaks at 64.3° C. and 80.5° C. respectively. Interestingly, a very weak secondary melt peak was identified in the No dTTP (GCA), indicating a low frequency of mis-incorporation.

Supercharged nucleotide incorporation can be further validated using accurate stage motors (Nanomotion, Israel) and a combination of microfluidic spotting devices functionalized areas on $Si/SiO_2$ wafer. In some embodiments, very small volumes of material are transferred to a surface via a sharp tip.

Figure 4:
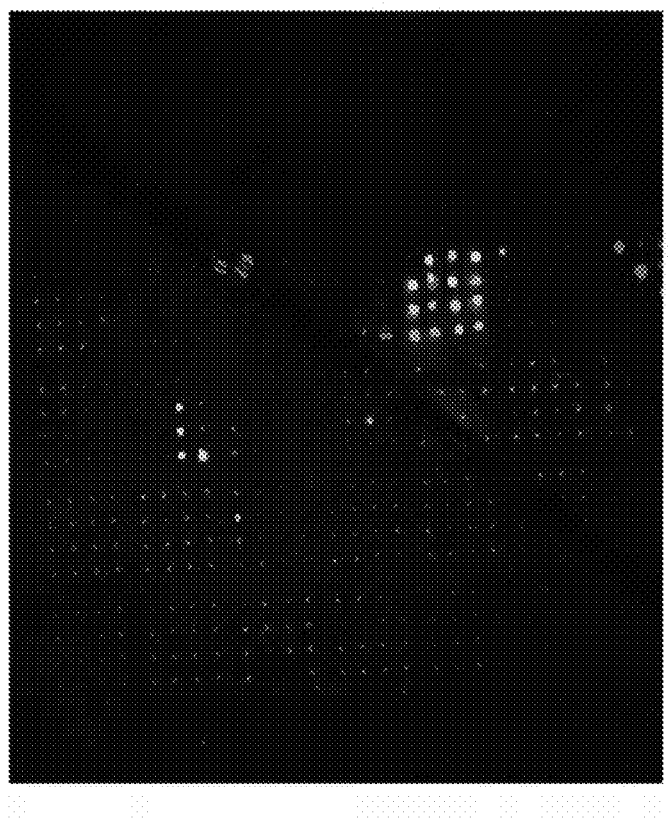
FIG. 4 shows fluorescence observed on the surface after a single Cy3 dCTP was incorporated into SCTTP.

In order to demonstrate primer extension optically, SC-TTP was incorporated into a sequence prior to a Cy3 labelled dCTP. SC-TTP does not contain a fluorescent moiety, by incorporating a Cy3 dCTP after the SC-TTP in the sequence; modified SC-TTP incorporation could be demonstrated (FIG. 4). Conditions for single Cy3 dCTP incorporation were elucidated using a standard PAGE-gel set-up and transferred to bulk silicon substrates. Competitor oligos, complementary to the templates were also designed to aid gel analysis of a single stranded product. Primer extension reactions were conducted using the following reaction mix:

| | |
|---|---|
| 2 µl | 10X Polymerase Buffer |
| 0.5 µl | 800 nM Primer |
| 0.5 µl | 600 nM Template |
| 2 µl | 2.5 mM dNTP mix |
| 2 µl | 1000 µ/ml DNA polymerase |
| 13 µl | Ultra-pure water |

Following incubated at 40° C. in a hot block reactions were terminated by the addition of a 'stop buffer' containing chelators to inhibit polymerase activity in addition to formamide and competitor oligo to encourage denaturation of the double stranded DNA duplex for electrophoresis. Interestingly, in reactions containing SC-TTP, bands were observed with a larger shift than in the positive control reaction. The additional shift is likely a result of the increased molecular weight of the SC-TTP compared to standard dCTP, potentially retarding gel migration. As such, this shift provides evidence towards successful SC-TTP incorporation.

Sequencing reactions performed on bulk Si/SiO$_2$ surfaces using both 3' and 5' surface tethered 30mer DNA, immobilised onto APDMES/PDC modified Si/SiO$_2$ surface in the typical 4×4 array format. Here, Cy3 labelled dCTP was selectively incorporated to a hybridised primer using the covalently bound 30mer probe as a template. The reaction mix was spread over the silicon surface and incubated overnight in a dark humid chamber at ambient temperature. The silicon was then rinsed in 1× Thermopol buffer and dried using a nitrogen line. Fluorescence was visualised using an Olympus BX60 and imaged using Axio vision camera and Axiovision 3.1 software.

FIG. 4 shows a fluorescence image taken of a printed array post-sequencing and wash steps. The very weak fluorescence indicates the single base incorporation of Cy3 labelled dCTP. It should be noted that each spot would contain a number of DNA strands where the primer extension has taken place and therefore the florescence observed is due to several Cy3 dCTP's not just one base. The control experiment where no primer was introduced into the reaction mixture yielded no fluorescence on the surface.

EXAMPLES

The following description is an illustrative example of some embodiments of the present disclosure.

Example 1

DNA Sequencing

The sequencing methodology in one example may not use fluorescence and expensive sensitive cameras, but instead may detect the addition of the synthetic nucleotides described in some aspects of the present disclosure, at least in part by sensing the electrical charge of reporter moiety, using sensitive nanostructures or sensors that may be capable of detecting a build up of charge mass at, or near, their surface. When a new nucleotide is added to the growing polymer in a sequencing by synthesis reaction, the charge density at, or near the surface of the sensitive nanostructure may increase and this can be detected by a change in property in the sensitive detection nanostructure or nano-/micro-sensor (for instance, if using a nanowire, or carbon nanotube, as the detecting structure, an increase in charge caused by the addition of a nucleotide close to its surface may be detected by a change in resistance in the wire, due to a phenomenon called the field effect). However, as the polymer grows, the signal may diminish as the charges carried by the nucleotides being added may be too far away from the sensitive nanostructure (e.g. nanowire) or sensor to illicit a change in property of the sensitive detection nanostructure or nano-/micro-sensor and no signal may be observed. Therefore, the 'read length' (amount of sequence data that is able to be obtained by this method of nucleotide sequencing) can be limited.

As used herein this particular example, a "sensitive detection nanostructure" can be any structure (nanoscale or not) which can be capable of detecting any change in charge at, or near it's surface and at any point may have at least one cross-sectional dimension less than about 500 nanometers, typically less than about 200 nanometers, more typically less than about 150 nanometers, still more typically less than about 100 nanometers, still more typically less than about 50 nanometers, even more typically less than about 20 nanometers, still more typically less than about 10 nanometers, and even less than about 5 nanometers. In other embodiments, at least one of the cross-sectional dimensions can generally be less than about 2 nanometers, or about 1 nanometer. In one set of embodiments the sensitive detection nanostructure or sensor can have at least one cross-sectional dimension ranging from about 0.5 nanometers to about 200 nanometers. For certain structures or sensors the detection of a change in charge is not direct but may be indirect i.e. via detection of from an additional property as a function of the fundamental change in charge.

The properties of a sensitive detection nanostructure or sensor may change in response to surface, or near surface charge in a way that may be measurable via piezoelectric measurements, electrochemical measurement, electromagnetic measurement, photodetection, mechanical, measurement, acoustic measurement, gravimetric measurement and the like. An example of a sensitive detection nanostructure or sensor may include, but not limited to, two dimension field effect transistors (FET), cantalevers, nanowires (operated as a FET or impedance or otherwise), nanopores, piezoelectric films, carbon nanotubes, and all appropriate macro-, micro-, nano-, pico-, zepto-, or smaller structures. The sensor may also be a waveguide.

Certain embodiments of the present disclosure may address this limitation, at least in part by using synthetic nucleotides that may comprise normal nucleotides, with a high negative (or positive) charge mass reporter moiety attached via a linker molecule (for instance, attached to the 5' phosphate group), with the linker length increasing as the reaction progresses. This charge mass can be designed to 'reach down' to the sensitive nanostructure (e.g. nanowire) to cause a change in property of the sensitive detection nanostructure or nano-/micro-sensor (e.g. a field effect or other piezo-electric change in the structure depending on the sensitive detection nanostructure or nano-/micro-sensor used). To enable a good quality control measure and to ensure long read lengths by eliminating the build up of many reporter moieties which would cause an ever increasing field effect, these reporter moieties can be cleaved at least in certain embodiments, to allow for the addition of the next nucleotide in the sequencing by synthesis sequence.

Therefore, in some embodiments the cyclical reaction may comprise at least some or whole of the following entire or partial series of events:

1. The template ssDNA molecule to be sequenced can be either ligated to the sensitive detection nanostructure or nano-/micro-sensor and a primer added, bind to a pre-immobilized primer sequence on the sensitive detection nanostructure or nano-/micro-sensor, or uncoiled and elongated in a microfluidics channel arrayed with sensitive detection nanostructure or nano-/micro-sensors.
2. The sensitive detection nanostructure or nano-/micro-sensors can be washed with water, or a low salt buffer (such as 1×SSC)
3. A measure of the sensitive detection nanostructure or nano-/micro-sensor can be made.
4. A mixture containing one synthetic nucleotide, the polymerase and other elements required for the polymerization reaction can be added. In one example, if the nucleotide added is complimentary to the base on the minus strand immediately after the primer sequence, it may be incorporated into the growing chain by the polymerase.
5. The reaction can then be washed with either water or a low salt buffer (such as 1×SSC).

6. A measure of the sensitive detection nanostructure or nano-/micro-sensor can be made which can observe the effect caused by the high charge mass of the reporter moiety.
7. The reporter moiety can then be cleaved (for instance by an acid solution or enzymatically).
8. Points 2 through 7 can be repeated for each of the four nucleotides. And this can be repeated repeatedly until a clear signal may degrade.

For some embodiments wherein the template molecule is immobilized to, or bound to a probe that can be in turn immobilized to the sensitive detection nanostructure or nano-/micro-sensor, the linker lengths that attach the high charge reporter moiety to the synthetic nucleotides may increase to enable the charge to 'reach down' to the sensitive detection nanostructure or nano-/micro-sensor to exert an effect. This may be necessary at least in some embodiments as the growing nucleotide polymer may move the next nucleotide addition site farther and farther from the sensitive detection nanostructure or nano-/micro-sensor as the sequencing by synthesis reaction may progress.

For some other embodiments wherein the template molecules is not immobilized to the sensitive detection nanostructure or nano-/micro-sensor, or hybridized to a primer/probe that can be in turn immobilized to the sensitive detection nanostructure or nano-/micro-sensor, and can be instead free or immobilized horizontally across a cluster of sensitive detection nanostructure or nano-/micro-sensors, a single linker length can be used for each of the cycle reactions.

Example 2

Primer Extension

In some embodiments, the synthetic nucleotides described in some aspects of the present disclosure for primer extension experiment wherein the detection is performed on electrical biosensors (nanowire/nanotube FETs, 2D FETS, nanopores, piezo-electric films/surfaces, etc). Primer extension is generally defined as a technique that can map or determine a 5' end of DNA or RNA. For example, primer extension can be used to determine the start site of the transcription start site for a gene. This technique generally requires a labelled primer, which is complementary to a region near the 3' end of the target gene. The primer is allowed to anneal to the transcript of the target gene and reverse transcriptase is used to synthesize complementary cDNA to the transcript until it reaches the 5' end of the transcript. By running the product on a polyacrylamide gel, it can be possible to determine the transcriptional start site, as the length of the sequence on the gel represents the distance from the start site to the labelled primer. During the synthesis of cDNA, the synthetic nucleotides disclosed in this application can be used and added to the nascent cDNA chain. The addition of the specific synthetic nucleic acid (e.g. deoxynucleotide with Adenine, Guanine, Thymidine, or Cystine) can be detected by a nanosensor. The nanosensor, which is further described below can be attached to the primer so that the nascent cDNA chain may be attached to the nanosensor in some embodiments. Alternatively, in some other embodiments, the transcript of the target sequence may be attached to the nanosensor (e.g. nanowires, nanotubes, nanobeads, nanopores, nanogaps and others).

Biosensors

As used in various embodiments, a biosensor is generally a device for the detection of an analyte that combines a biological component with a physicochemical detector component. In some embodiments, it may comprise three parts: 1. the sensitive biological element (biological material (e.g. tissue, microorganisms, organelles, cell receptors, enzymes, antibodies, nucleic acids, etc), a biologically derived material or biomimic). The sensitive elements can be created by biological engineering; 2. the transducer or the detector element (works in a physicochemical way; optical, piezo-electric, electrochemical, etc.) that transforms the signal resulting from the interaction of the analyte with the biological element into another signal (i.e., transducers) that can be more easily measured and quantified; 3. associated electronics or signal processors that is primarily responsible for the display of the results in a user-friendly way. In some other examples, the signal processing unit may further comprise one or more of a signal sensing unit, a signal recording unit, a data processing unit, and a data reporting unit.

Nanostructures

As used in various embodiments, a nanowire is an elongated nanoscale semiconductor which, at any point along its length, has at least one cross-sectional dimension and, in some embodiments, two orthogonal cross-sectional dimensions less than 500 nanometers, preferably less than 200 nanometers, more preferably less than 150 nanometers, still more preferably less than 100 nanometers, even more preferably less than 70, still more preferably less than 50 nanometers, even more preferably less than 20 nanometers, still more preferably less than 10 nanometers, and even less than 5 nanometers. In other embodiments, the cross-sectional dimension can be less than 2 nanometers or 1 nanometer. In one set of embodiments the nanowire has at least one cross-sectional dimension ranging from 0.5 nanometers to 200 nanometers. Where nanowires are described having a core and an outer region, the above dimensions relate to those of the core. The cross-section of the elongated semiconductor may have any arbitrary shape, including, but not limited to, circular, square, rectangular, elliptical and tubular. Regular and irregular shapes are included. A non-limiting list of examples of materials from which nanowires of the invention can be made appears below.

Nanotubes are a class of nanowires that may find use in the invention and, in one embodiment, devices of the invention include wires of scale commensurate with nanotubes. As used herein, a "nanotube" is a nanowire that has a hollowed-out core, and includes those nanotubes know to those of ordinary skill in the art. A "non-nanotube nanowire" is any nanowire that is not a nanotube. In one set of embodiments of the invention, a non-nanotube nanowire having an unmodified surface (not including an auxiliary reaction entity not inherent in the nanotube in the environment in which it is positioned) is used in any arrangement of the invention described herein in which a nanowire or nanotube can be used. A "wire" refers to any material having a conductivity at least that of a semiconductor or metal. For example, the term "electrically conductive" or a "conductor" or an "electrical conductor" when used with reference to a "conducting" wire or a nanowire refers to the ability of that wire to pass charge through itself. Preferred electrically conductive materials have a resistivity lower than about $10^{-3}$, more preferably lower than about $10^{-4}$, and most preferably lower than about $10^{-6}$ or $10^{-7}$ ohm-meters.

Nanopore generally has one or more small holes in an electrically insulating membrane that can be used as a single-molecule detector. In some cases, it can be a biological protein channel in a high electrical resistance lipid bilayer or a pore in a solid-state membrane. Nanopore is generally a spherical structure in a nanoscale size with one or more pores therein. According to some aspects, a nanopore is made of carbon or any conducting material.

Nanobead is generally a spherical structure in a nanoscale size. The shape of nanobead is generally spherical but can also be circular, square, rectangular, elliptical and tubular. Regular and irregular shapes are included. In some examples, the nanobead may have a pore inside.

Nanogap is generally used in a biosensor that consists of separation between two contacts in the nanometer range. It senses when a target molecule, or a number of target molecules hybridize or binds between the two contacts allowing for the electrical signal to be transmitted through the molecules.

The foregoing nanostructures, namely, nanowire, nanotube, nanopore, nanobead, and nanogap are described to provide the instant illustration of some embodiments, and not for limiting the scope of the present invention. In addition to the foregoing examples, any nanostructure that has a nanoscale size and is suitable to be applied to nucleic acid detection methods and apparatus as disclosed in the application should also be considered to be included in the scope of the invention. It should be appreciated that detection can also occur with other non nano-scale structures such on FET arrays which are in the micron-scale and discussed further below.

In general, sensing strategies for use with nanostructures or nanosensors to detect molecules and compounds is to sense changes in the charge at, or near their surfaces, or across a nanogap or nanopore, which cause a measurable change in their properties (such as field effect transistors, nanogaps, or piezoelectric nanosensors) to detect & quantify target nucleic acids (DNA, RNA, cDNA, etc).

Aspects of the invention provide a nanowire or nanowires preferably forming part of a system constructed and arranged to determine an analyte in a sample to which the nanowire(s) is exposed. "Determine", in this context, means to determine the quantity and/or presence of the analyte in the sample. Presence of the analyte can be determined by determining a change in a characteristic in the nanowire, typically an electrical characteristic or an optical characteristic. E.g. an analyte causes a detectable change in electrical conductivity of the nanowire or optical properties. In one embodiment, the nanowire includes, inherently, the ability to determine the analyte. The nanowire may be functionalized, i.e. comprising surface functional moieties, to which the analytes binds and induces a measurable property change to the nanowire. The binding events can be specific or non-specific. The functional moieties may include simple groups, selected from the groups including, but not limited to, —OH, —CHO, —COOH, —SO₃H, —CN, —NH₂, —SH, —COSH, COOR, halide; biomolecular entities including, but not limited to, amino acids, proteins, sugars, DNA, antibodies, antigens, and enzymes; grafted polymer chains with chain length less than the diameter of the nanowire core, selected from a group of polymers including, but not limited to, polyamide, polyester, polyimide, polyacrylic; a thin coating covering the surface of the nanowire core, including, but not limited to, the following groups of materials: metals, semiconductors, and insulators, which may be a metallic element, an oxide, an sulfide, a nitride, a selenide, a polymer and a polymer gel. In another embodiment, the invention provides a nanowire and a reaction entity with which the analyte interacts, positioned in relation to the nanowire such that the analyte can be determined by determining a change in a characteristic of the nanowire.

Microstructures or Microsensor

In some embodiments, a sensor which is similar in the foregoing nanostructures with respect to a shape, structure, and property but has a different dimension, e.g. micro-scale, can be used. Thus, in some examples, a microstructure may be in form of an elongated microscale semiconductor which, at any point along its length, has at least one cross-sectional dimension and, in some embodiments, two orthogonal cross-sectional dimensions less than 500 micrometers, preferably less than 200 micrometers, less than 150 micrometers, less than 100 micrometers, less than 70, less than 50 micrometers, less than 20 micrometers, less than 10 micrometers, less than 5 micrometers, less than 4 micrometers, less than 3 micrometers, less than 2 micrometers, and even less than 1 micrometer. In other embodiments, the cross-sectional dimension can be less than 2 micrometers or 1 micrometer. In one set of embodiments the microwire has at least one cross-sectional dimension ranging from 0.5 micrometers to 200 micrometers. Where microwires are described having a core and an outer region, the above dimensions relate to those of the core. The cross-section of the elongated semiconductor may have any arbitrary shape, including, but not limited to, circular, square, rectangular, elliptical and tubular. Regular and irregular shapes are included. A non-limiting list of examples of materials from which microwires of the invention can be made appears below. Alternatively or in combination, the microstructure or microsensor can be in any shape or structure, e.g. microtubes, micropores, microbeads, and microgaps that have essentially similar properties of nanostructures in terms of sensing an electrical signal but have a different dimension, at least in some part(s) of its structure, e.g. a cross-section, depth, and/or length, in micro-scale.

Field Effect Transistor (FET)

Field effect generally refers to an experimentally observable effect symbolized by F (on reaction rates, etc.) of intramolecular coulombic interaction between the centre of interest and a remote unipole or dipole, by direct action through space rather than through bonds. The magnitude of the field effect (or 'direct effect') may depend on the unipolar charge/dipole moment, orientation of dipole, shortest distance between the centre of interest and the remote unipole or dipole, and on the effective dielectric constant. This is exploited in transistors for computers and more recently in DNA field-effect transistors used as nanosensors.

Field-effect transistor (FET) is generally a field-effect transistor, which may use the field-effect due to the partial charges of biomolecules to function as a biosensor. The structure of FETs can be similar to that of metal-oxide-semiconductor field-effect transistor (MOSFETs) with the exception of the gate structure which, in biosensor FETs, may be replaced by a layer of immobilized probe molecules which act as surface receptors. When target biomolecules hybridize or bind, to the receptors, the charge distribution near the surface changes, which in turn modulates current transport through the semiconductor transducer (e.g. nanowire).

Biological Samples

The term sample or biological sample generally refers to any cell, tissue, or fluid from a biological source (a "biological sample"), or any other medium, biological or non-biological, that can be evaluated in accordance with the invention including, such as serum or water. A sample includes, but is not limited to, a biological sample drawn from an organism (e.g. a human, a non-human mammal, an invertebrate, a plant, a fungus, an algae, a bacteria, a virus, etc.), a sample drawn from food designed for human consumption, a sample including food designed for animal consumption such as livestock feed, milk, an organ donation sample, a sample of blood destined for a blood supply, a sample from a water supply, or the like. One example of a sample is a sample drawn from a human or animal to determine the presence or absence of a specific nucleic acid sequence.

Nucleic Acid or Oligonucleotide

The terms nucleic acid or oligonucleotide or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) Tetrahedron 49(10): 1925) and references therein; Letsinger (1970) J. Org. Chem. 35:3800; Sprinzl et al. (1977) Eur. J. Biochem. 81: 579; Letsinger et al. (1986) Nucl. Acids Res. 14: 3487; Sawai et al. (1984) Chem. Lett. 805, Letsinger et al. (1988) J. Am. Chem. Soc. 110: 4470; and Pauwels et al. (1986) Chemica Scripta 26: 1419), phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321, O-methylphophoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31: 1008; Nielsen (1993) Nature, 365: 566; Carlsson et al. (1996) Nature 380: 207). Other analog nucleic acids include those with positive backbones (Denpcy et al. (1995) Proc. Natl. Acad. Sci. USA 92: 6097; non-ionic backbones (U.S. Pat. Nos. 5,386,023, 5,637,684, 5,602,240, 5,216,141 and 4,469,863; Angew. (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), Chem. Soc. Rev. pp. 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

Sensing Strategies

In one aspect of the invention, a biological material configured to bind a nanostructure is a nucleic acids. Such nucleic acids may include DNA, RNA, and any derivatives thereof. In one embodiment, the biological material is DNA. When DNA is attached to the nanostructure, the number of nucleotides may range from 5 bases to 100 bases. In some embodiments, the number of DNA nucleotides may be 7 bases, 10 bases, 15 bases, 20, bases, 25 bases, 30 bases, 35 bases, 40 bases, 45 bases, 50 bases, 60 bases, 70 bases, 80 bases, 90 bases and 100 bases. In some other embodiments, ribonucleic acids and any nucleic acid derivatives may be attached to the nanostructure. In still some other embodiments, DNA, RNA and its derivatives may be used simultaneously. Therefore in one example, DNA sequences may be attached to the nanostructure, whereas in another example, RNA sequences may be attached to the nanostructure, still another example, nucleic acid derivatives such as a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof may be attached to the nanostructure. In some other examples, nucleotide sequences comprising DNA and RNA, DNA and nucleic acid derivatives, RNA and derivatives, and DNA, RNA and derivatives may be attached to the nanostructure.

In another aspect of the invention, a nanostructure is conducting and can sense the electric charge, which is originated from the synthetic nucleotide as disclosed in this application, at its surface, vicinity, inner tubes and/or the pores therein. One of key aspects of any diagnostic device is the ability to perform accurate detection of biomolecules with the performance determined by how well it detects specifically (i.e. a low false positive rate) and sensitively (i.e. a low false negative rate). Nanosensors that can sense changes in the charge at, or near their surfaces, or across a nanogap or nanopore, which cause a measurable change in their properties, at least in part due to the target molecule binding to a probe immobilized on or near the nanostructures, provide a method for ultra-sensitive detection without or with limited use of the need for labels (expensive chemicals that can be bound to the biomolecule or molecule of interest to enable detection devices to 'sense' them).

The present disclosure generally relates to molecular biological protocols and sensing strategies for use with nanosensors that may detect molecules and compounds by sensing changes in the charge at, or near their surfaces, or across a nanogap or nanopore, which cause a measurable change in their properties (such as field effect transistors, nanogaps, or piezoelectric nanostructures or nanosensors) to detect & quantify target nucleic acids (DNA, RNA, cDNA, etc). The basic function of these biosensors may require that a nucleotide polymer probe (or synthetic nucleotide polymer such as PNA, Morpholinos, etc) be immobilized on, or near to, the nanostructures and the build up of target molecules binding to the probe can cause an increase in charge density at or near the surface of the nanostructures or nanosensors, due to the charge of the probe. For instance, an amplified PCR fragment binding to a probe (with a reverse complimentary sequence to the target nucleotide polymer), immobilized on a nanowire can cause a measurable change conductance ($\Delta G$) due to the increase in negative charge at, or near to the nanowire's surface, due to a phenomena called the field effect. In some embodiments, the electric charge present in the synthetic nucleotide, which is originated from the nucleotide itself and the high charge mass reporter moiety, can be detected by the nanostructures/nanosensors.

These nanosensors may offer the potential for sensitive and dynamic detection of biomolecules, however, this sensitivity may bring with it a number of issues. For instance, natural fluctuations of charge at the surface, within the sample matrix may cause noise, in part due to the flanking sequences of target nucleotide polymer molecules (i.e. the over hanging sequences that don't bind to the probes). Furthermore, if many target molecules are being detected at the same time on an array of nanosensors, it would be favorable to standardize the size and therefore charge mass, of each of these molecules to allow for more stringent comparisons and quality control. Moreover, having a standard size for all target molecules allows for standardization of probe hybridization conditions in the array assay design.

Biosensor System

Biosensor is generally an analytical device that may convert molecular events into electrical signals. The nanostructures used in a biosensor are generally used to detect components of interest such as nucleic acids. Biosensors can generally operate in the liquid or gas phase, opening up an enormous variety of applications, e.g., for integrated devices and for downstream applications. Therefore, the biosensors can be manufactured inexpensively and portable and are optionally used as implantable detection and monitoring devices. Alternatively, the biosensor can be coupled with other high-resolution apparatus such as mass-spectroscopy and provide further information including the detection of presence, abundance and/or structural variation of the target biomolecules.

One aspect of the invention involves a sensing element of a biosensor, which can be an electronic sensing element, and a nanowire able to detect the presence, or absence, of an analyte in a sample (e.g. a fluid sample) containing, or suspected of containing, the analyte. Nanoscale sensors of the invention may be used, for example, in chemical applications to detect pH or the presence of metal ions; in biological applications to detect a protein, nucleic acid (e.g. DNA, RNA, etc.), a sugar or carbohydrate, and/or metal ions; and in environmental applications to detect pH, metal ions, or other analytes of interest.

Another aspect of the invention involves an article of a biosensor comprising a sample exposure region and a nanowire able to detect the presence of absence of an analyte. The sample exposure region may be any region in close proximity to the nanowire wherein a sample in the sample exposure region addresses at least a portion of the nanowire. Examples of sample exposure regions include, but are not limited to, a well, a channel, a microchannel, and a gel. In preferred embodiments, the sample exposure region holds a sample proximate the nanowire, or may direct a sample toward the nanowire for determination of an analyte in the sample. The nanowire may be positioned adjacent to or within the sample exposure region. Alternatively, the nanowire may be a probe that is inserted into a fluid or fluid flow path. The nanowire probe may also comprise a micro-needle and the sample exposure region may be addressable by a biological sample. In this arrangement, a device that is constructed and arranged for insertion of a micro-needle probe into a biological sample will include a region surrounding the micro-needle that defines the sample exposure region, and a sample in the sample exposure region is addressable by the nanowire, and vice-versa. Fluid flow channels can be created at a size and scale advantageous for use in the invention (microchannels) using a variety of techniques such as those described in International Patent Publication No. WO 97/33737, published Sep. 18, 1997, and incorporated herein by reference.

In another aspect of the invention, an article may comprise a plurality of nanowires able to detect the presence or absence of a plurality of one or more analytes. The individual nanowires may be differentially doped as described above, thereby varying the sensitivity of each nanowire to the analyte. Alternatively, individual nanowires may be selected based on their ability to interact with specific analytes, thereby allowing the detection of a variety of analytes. The plurality of nanowires may be randomly oriented or parallel to one another. Alternatively, the plurality of nanowires may be oriented in an array on a substrate.

Where a detector is present, any detector capable of determining a property associated with the nanowire can be used. The property can be electronic, optical, or the like. An electronic property of the nanowire can be, for example, its conductivity, resistivity, etc. An optical property associated with the nanowire can include its emission intensity, or emission wavelength where the nanowire is an emissive nanowire where emission occurs at a p-n junction. For example, the detector can be constructed for measuring a change in an electronic or magnetic property (e.g. voltage, current, conductivity, resistance, impedance, inductance, charge, etc.) can be used. The detector typically includes a power source and a voltmeter or amp meter. In one embodiment, a conductance less than 1 nS can be detected. In a preferred embodiment, a conductance in the range of thousandths of a nS can be detected. The concentration of a species, or analyte, may be detected from less than micromolar to molar concentrations and above. By using nanowires with known detectors, sensitivity can be extended to a single molecule. In one embodiment, an article of the invention is capable of delivering a stimulus to the nanowire and the detector is constructed and arranged to determine a signal resulting from the stimulus. For example, a nanowire including a p-n junction can be delivered a stimulus (electronic current), where the detector is constructed and arranged to determine a signal (electromagnetic radiation) resulting from the stimulus. In such an arrangement, interaction of an analyte with the nanowire, or with a reaction entity positioned proximate the nanowire, can affect the signal in a detectable manner. In another example, where the reaction entity is a quantum dot, the quantum dot may be constructed to receive electromagnetic radiation of one wavelength and emit electromagnetic radiation of a different wavelength. Where the stimulus is electromagnetic radiation, it can be affected by interaction with an analyte, and the detector can detect a change in a signal resulting therefrom. Examples of stimuli include a constant current/voltage, an alternating voltage, and electromagnetic radiation such as light.

Another aspect of the present invention provides an article comprising a nanowire and a detector constructed and arranged to determine a change in an electrical property of the nanowire. At least a portion of the nanowire is addressable by a sample containing, or suspected of containing, an analyte. The phrase "addressable by a fluid" is defined as the ability of the fluid to be positioned relative to the nanowire so that an analyte suspected of being in the fluid is able to interact with the nanowire. The fluid may be proximate to or in contact with the nanowire.

In some embodiments, the nanostructures can be assembled into a plurality of parallel arrays such as microcolumns at higher densities than is and in a format compatible with currently available micro-fluidic systems. The nanostructure arrays optionally comprise a plurality of nanostructures such as nanowires, nanotubes, nanopores, nanobeads, nanogaps, or a combination thereof. Each nanostructure of the array can be electrically connected, e.g., via two or more electrodes to a battery for applying a voltage across the nanowire and a detector, for detection of any changes in conductance of the nanowire. Alternatively, each nanostructure separately receives electricity or only a portion of nanostructures arrayed together may be electrically connected.

A single detector or a combination of detectors is optionally used to detect the signal from the array of nanowires. For example, each nanowire linked to a probe comprising different target sequence, which may be bound to a same or different probe, is optionally detected separately, such that a spatial array of a plurality of nanowires can be used to quickly identify, e.g., a plurality of different nucleotide sequences present in a biological sample such as blood. In some examples, a plurality of patches of nanostructures are prepared in the array and each patch presents different probes to detect multiple target sequences in a biological sample. Alternatively, in some other examples, an entire nanostructures present in the array may present same probes, thereby only one target sequence would be tested for its presence, abundance and/or variation in the sequence.

The detection by the nanostructure or nanosensor is generally a change in conductance of the nanostructure or of its environment. The signal can be expressed in terms of a change in the voltage across the nanostructure, or the current through the nanostructure. Such changes are typically detected electrically, e.g., with a voltmeter and/or a current meter. Alternatively, the signal is detected digitally. In one embodiment, a voltage is applied across a nanostructure, e.g., a nanowire, providing a steady state signal. When a binding event occurs on the probe attached to the nanostructure, the electric field in the vicinity of the nanostructure changes and the conductance of the nanostructure changes, producing a fluctuation or shift in the steady state signal. The signal may be detected, electrically or digitally, and provides real time detection of the event of interest.

Biosensor can also be integrated into a system for detecting a presence, level and/or variation of biomolecules. In one aspect, such system may include an electrical power supply, monitoring system for applying and measuring electrical current across the nanostructure element. In another aspect, such system may further include data processing capabilities to enable the programmed operation of the nanostructures and to receive, store, and provide useful analysis and display of the data that is obtained. In addition a computer system to process the obtained data as well as additional processor(s) may be integrated into a biosensor system if desired. The computer system or any additional elements present in a biosensor system may provide a software(s) for analyzing the data or for automatic operation and/or manual(s) to perform detection processes with a biosensor. Furthermore, any additional elements that may enhance the performance of a biosensor system can be added. A biosensor of the present invention can collect real time data.

Example 3

Hybridization Such as Microarrays

In other embodiments, the synthetic nucleotide disclosed in some aspects of the present disclosure can be used for hybridization procedures. Some non-limiting, illustrative examples of the hybridization procedures include a microarray for nucleonic acids as well as proteins. Further any other procedures that need hybridization and can determine presence, abundance or any structural variation of the target biomolecules can be included.

In one example, the probes used in a microarray can be attached to a medium such as nanosensors (e.g. nanowires, nanotubes, nanobeads, nanoopores, nanogaps, and other nanostructures). In some cases, the target nucleotide sequences obtained from the biological samples would be labeled and contacted with the probes. In such cases, the target nucleotide may incorporate the synthetic nucleotides thereby being labeled with "high charge mass". As such, the binding of the target sequences to the probes can be readily determined by the nanosensors that the probes are attached to. Moreover, the synthetic nucleotide disclosed in this application can be used, for example, in the methods of detecting presence, abundance and/or structural variation of nucleic acids as disclosed in the related application of the subject application, U.S. provisional application No. 61/094, 017 filed on Sep. 3, 2008, the disclosures of which are hereby expressly incorporated by reference in their entirety and are hereby expressly made a portion of this application. As such, the use of the synthetic nucleotide of this application is not limited and can be further extended if applicable.

Example 4

Synthesis of Supercharged TTP (SCTTP)

5'-O-Dimethoxytrityl-5-iodo-2'-deoxyuridine

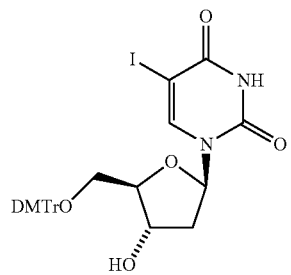

5-Iodo-2'-deoxyuridine (5.00 g, 14.1 mmol) was dissolved in anhydrous pyridine (57.5 mL) and stirred under nitrogen. After 5 min, 4-(dimethylamino)pyridine (86 mg, 0.70 mmol) and triethylamine (199 mg, 275 μL, 1.97 mmol) were added to the reaction mixture, followed by 4,4'-dimethoxytriphenylmethyl chloride (5.73 g, 16.9 mmol). The resulting reaction mixture was stirred at room temperature for 4 h and it was then quenched with methanol (8.3 mL) before being concentrated under reduced pressure. The residue obtained was partitioned between water (250 mL) and dichloromethane (250 mL). The aqueous phase was washed with dichloromethane (50 mL) and the organic phases were combined, dried ($MgSO_4$) and concentrated under reduced pressure to give a yellow glassy solid. This material was purified using a Biotage Isolera automated chromatography system under normal phase conditions (silica column, gradient of 0→80% ethyl acetate in dichloromethane) with detection at 254 nm to give 5'-O-dimethoxytrityl-5-iodo-2'-deoxyuridine (8.59 g, 93%), as a pale yellow solid.

$R_f$ 0.20 (dichloromethane-ethyl acetate, 8:2, v/v).

$^1$H NMR (300 MHz, $d_6$-DMSO): 11.76 (s, 1H, NH), 8.01 (s, 1H, CH), 7.33 (m, 9H, 9×ArH), 6.90 (m, 4H, 4×ArH), 6.10 (t, J=7.1 Hz, 1H, CH), 5.32 (d, J=4.5 Hz, 1H, OH), 4.23 (m, 1H, CH), 3.90 (m, 1H, CH), 3.74 (s, 6H, 2×$OCH_3$), 3.17 (m, 2H, $CH_2$), 2.22 (m, 2H, $CH_2$).

3'-O-Pivaloyl-5'-O-dimethoxytrityl-5-iodo-2'-deoxyuridine

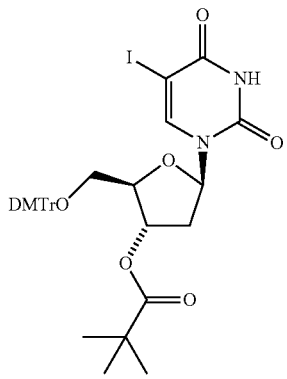

5'-O-Dimethoxytrityl-5-iodo-2'-deoxyuridine (10.2 g, 15.6 mmol) was dissolved in anhydrous acetonitrile (205 mL). 4-(Dimethylamino)pyridine (95 mg, 0.78 mmol) and triethylamine (3.95 g, 5.44 mL, 39.0 mmol) followed by trimethylacetic anhydride (5.97 g, 6.50 mL, 32.0 mmol) were added. The reaction mixture was stirred and heated at reflux for 20 h. after which it was allowed to cool to room temperature and methanol (6.6 mL) was added. The resulting solution was concentrated under reduced pressure to give a brown oil which was purified using a Biotage Isolera automated chromatography system under normal phase conditions (silica column, gradient of 0→70% ethyl acetate in dichloromethane) with detection at 254 nm to give 3'-O-pivaloyl-5'-O-dimethoxytrityl-5-iodo-2'-deoxyuridine (9.22 g, 80%), as a white solid. Unreacted 5'-O-dimethoxytrityl-5-iodo-2'-deoxyuridine (2.08 g) was also recovered and was recycled.

$R_f$ 0.68 (dichloromethane-ethyl acetate, 8:2, v/v).

$^1$H NMR (300 MHz, $d_6$-DMSO): 11.80 (s, 1H, NH), 8.08 (s, 1H, CH), 7.29 (m, 9H, 9×ArH), 6.89 (m, 4H, 4×ArH), 6.10 (t, J=7.1 Hz, 1H, CH), 5.21 (m, 1H, CH), 3.99 (m, 1H, CH), 3.74 (s, 6H, 2×OCH$_3$), 3.27 (m, 2H, CH$_2$), 2.28 (m, 2H, CH$_2$), 1.12 (s, 9H, 3×CH$_3$).

3'-O-Pivaloyl-5-iodo-2'-deoxyuridine

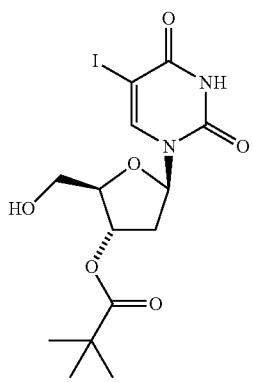

3'-O-Pivaloyl-5'-O-dimethoxytrityl-5-iodo-2'-deoxyuridine (5.35 g, 7.23 mmol) was dissolved in dichloromethane (34 mL) and trifluoroacetic acid (615 µL) was added dropwise. The resulting reaction mixture was stirred at room temperature for 1 h. A second portion of trifluoroacetic acid (615 µL) was added and the mixture was stirred at room temperature for a further 1 h. A third portion of trifluoroacetic acid (615 µL) was added and the mixture was stirred at room temperature for 1 h. The resulting mixture was diluted with dichloromethane (120 mL) and washed with saturated aqueous sodium bicarbonate solution (80 mL). The layers were separated and the aqueous phase was extracted with dichloromethane (80 mL). The organic layers were combined, dried (MgSO$_4$) and concentrated under reduced pressure to afford a pale yellow solid. This solid was purified using a Biotage Isolera automated chromatography system under normal phase conditions (silica column, gradient of 0→60% ethyl acetate in dichloromethane) with detection at 285 nm to give 3'-O-pivaloyl-5-iodo-2'-deoxyuridine (2.56 g, 81%), as a white solid.

$R_f$ 0.41 (dichloromethane-ethyl acetate, 7:3, v/v).

$^1$H NMR (300 MHz, $d_6$-DMSO): 11.74 (s, 1H, NH), 8.40 (s, 1H, CH), 6.14 (t, J=7.1 Hz, 1H, CH), 5.33 (t, J=5.0 Hz 1H, OH), 5.20 (m, 1H, CH), 3.97 (m, 1H, CH), 3.64 (m, 2H, CH$_2$), 2.28 (m, 2H, CH$_2$), 1.16 (s, 9H, 3×CH$_3$).

3'-O-Pivaloyl-5-(N-Boc-3-amido-propynyl)-2'-deoxyuridine

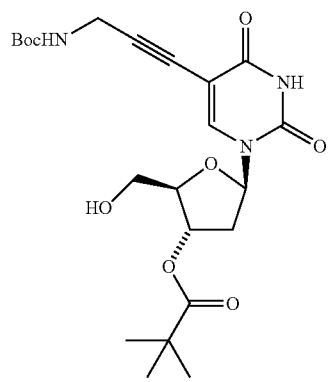 [SMILES: CC(C)(C)OC(=O)NCC#Cc1cn([C@H]2C[C@H](OC(=O)C(C)(C)C)[C@@H](CO)O2)c(=O)[nH]c1=O]

3'-O-Pivaloyl-5-iodo-2'-deoxyuridine (2.55 g, 5.82 mmol), copper(I) iodide (221 mg, 1.16 mmol) and tetrakis(triphenylphosphine)palladium(0) (670 mg, 0.58 mmol) were dissolved in anhydrous DMF (36.5 mL) and the flask was evacuated and purged with nitrogen. Hunig's base (1.50 g, 1.98 mL, 11.6 mmol) and N-Boc-propargylamine (2.71 g, 17.5 mmol) were added and the resulting mixture was stirred at room temperature overnight. The reaction mixture was diluted with ethyl acetate (170 mL), washed with 5% aqueous EDTA solution (2×60 mL) and saturated brine (50 mL). The organic layer was dried (MgSO$_4$) and concentrated under reduced pressure to give an orange oil. This oil was purified using a Biotage Isolera automated chromatography system under normal phase conditions (silica column, gradient of 0→100% ethyl acetate in dichloromethane) with detection at 295 nm to give 3'-O-pivaloyl-5-(N-Boc-3-aminopropynyl)-2'-deoxyuridine (2.31 g, 85%), as a yellow solid.

$R_f$ 0.38 (dichloromethane-ethyl acetate, 1:1, v/v).

$^1$H NMR (300 MHz, $d_6$-DMSO): 11.68 (s, 1H, NH), 7.34 (t, J=5.6 Hz, 1H, NH), 8.16 (s, 1H, CH), 6.14 (t, J=7.1 Hz, 1H, CH), 5.27 (t, J=5.0 Hz, 1H, OH), 5.19 (m, 1H, CH), 3.95

(m, 3H, CH+CH$_2$), 3.63 (m, 2H, CH$_2$), 2.28 (m, 2H, CH$_2$), 1.39 (s, 9H, 3×CH$_3$), 1.16 (s, 9H, 3×CH$_3$).

3'-O-Pivaloyl-5-(3-aminopropynyl)-2'-deoxyuridine Trifluoroacetate

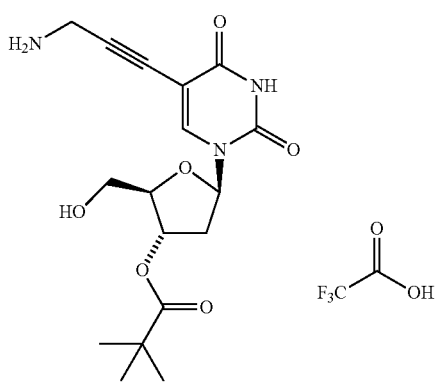 [SMILES: CC(C)(C)C(=O)O[C@H]1C[C@H](n2cc(C#CCN)c(=O)[nH]c2=O)O[C@@H]1CO ; O=C(O)C(F)(F)F]

3'-O-Pivaloyl-5-(N-Boc-3-aminopropynyl)-2'-deoxyuridine (2.02 g, 4.34 mmol) was dissolved in dichloromethane (32 mL) and trifluoroacetic acid (6 mL) was added. The resulting mixture was stirred for 2 h at room temperature and was subsequently concentrated under reduced pressure. The residual trifluoroacetic acid was azeotropically removed with dichloromethane (4×50 mL). The material obtained was purified using a Biotage Isolera automated chromatography system under reversed-phase conditions (C$_{18}$ column, gradient of 0→60% acetonitrile in 0.1% trifluoroacetic acid) with detection at 287 nm to afford, after freeze-drying, 3'-O-pivaloyl-5-(3-aminopropynyl)-2'-deoxyuridine trifluoroacetate (Fragment 1) (1.55 g, 75%), as an off-white solid.

$^1$H NMR (300 MHz, d$_6$-DMSO) 11.80 (s, 1H, NH), 8.28 (br, 4H, CH+NH$_3^+$), 6.14 (t, J=7.1 Hz, 1H, CH), 5.32 (br, 1H, OH), 5.21 (m, 1H, CH), 3.99 (m, 3H, CH+CH$_2$), 3.64 (m, 2H, CH$_2$), 2.28 (m, 2H, CH$_2$), 1.16 (s, 9H, 3×CH$_3$).

3-[(1,3)Dioxolan-2-ylmethoxy]benzoic acid ethyl ester

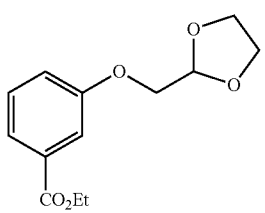 [SMILES: CCOC(=O)c1cccc(OCC2OCCO2)c1]

Ethyl 3-hydroxybenzoate (2.23 g, 13.4 mmol), bromoethyl-1,3-dioxolane (8.97 g, 5.56 mL, 53.7 mmol), potassium carbonate (3.72 g, 26.9 mmol) and sodium iodide (0.81 g, 5.37 mmol) were dissolved in anhydrous DMF (6 mL) and the reaction mixture was stirred at 120° C. for 17 h. The resulting suspension was cooled to room temperature and quenched with water (50 mL). The aqueous phase was extracted with ethyl acetate (3×50 mL). The organic layers were combined, washed with water (5×100 mL), dried (MgSO$_4$) and concentrated under reduced pressure to afford an orange oil. This oil was purified using a Biotage Isolera automated chromatography system under normal phase conditions (silica column, gradient of 0→35% ethyl acetate in petrol) with detection at 254 nm to give 3-[(1,3)dioxolan-2-ylmethoxy]benzoic acid ethyl ester (3.12 g, 92%), as a colorless oil.

R$_f$ 0.40 (petrol-ethyl acetate, 75:25, v/v).
$^1$H NMR (400 MHz, CDCl$_3$) δ 7.66 (dt, 1H, J=7.5, 1.1 Hz, ArH), 7.59 (dd, 1H, J=2.6, 1.5 Hz, ArH), 7.34 (t, 1H, J=7.9 Hz, ArH), 7.14 (ddd, 1H, J=8.3, 2.6, 1.0 Hz, ArH), 5.31 (t, 1H, J=4.1 Hz, CH), 4.36 (q, 2H, 7.2 Hz, OCH$_2$), 4.02 (m, 6H, OCH$_2$CH$_2$O+ArOCH$_2$), 1.39 (t, 3H, J=7.1 Hz, CH$_3$).

3-[2-Azido-2-(2-hydroxyethoxy)ethoxy]benzoic acid ethyl ester

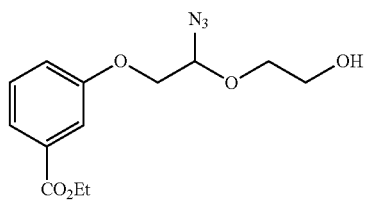

To a mixture of 3-[(1,3)dioxolan-2-ylmethoxy]benzoic acid ethyl ester (3.12 g, 12.4 mmol) and azidotrimethylsilane (1.57 g, 1.81 mL, 13.6 mmol) was added tin(IV) chloride (206 mg, 93 μL, 0.79 mmol). The reaction mixture was stirred at room temperature for 2 h. The resulting mixture was diluted with 2% aqueous methanol (20 mL) and stirred for 30 min before being concentrated under reduced pressure. The residue was azeotropically dried with ethanol (2×15 mL) to afford a colorless viscous oil. This oil was purified using a Biotage Isolera automated chromatography system under normal phase conditions (silica column, gradient of 0→70% ethyl acetate in petrol) with detection at 254 nm to give 3-[2-azido-2-(2-hydroxyethoxy)ethoxy]benzoic acid ethyl ester (2.46 g, 69%), as a colorless oil.

R$_f$ 0.40 (petrol-ethyl acetate, 53:47, v/v).
$^1$H NMR (300 MHz, CDCl$_3$) δ 7.69 (dt, 1H, J=7.7, 1.2 Hz, ArH), 7.59 (dd, 1H, J=2.6, 1.5 Hz, ArH), 7.36 (t, 1H, J=8.0 Hz, ArH), 7.13 (ddd, 1H, J=8.3, 2.7, 1.0 Hz, ArH), 4.89 (t, 1H, J=5.1 Hz, CH), 4.38 (q, 2H, 7.1 Hz, OCH$_2$), 4.19 (m, 2H, ArOCH$_2$), 4.00 (m, 1H, 0.5×OCH$_2$), 3.80 (m, 3H, 0.5×OCH$_2$+OCH$_2$), 1.40 (t, 3H, J=7.1 Hz, CH$_3$).

3-[2-Azido-2-(2-hydroxyethoxy)ethoxy]benzoic acid

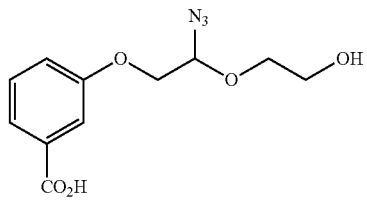 [SMILES: [N-]=[N+]=NC(COc1cccc(C(=O)O)c1)OCCO]

3-[2-Azido-2-(2-hydroxyethoxy)ethoxy]benzoic acid ethyl ester (2.39 g, 8.10 mmol) was dissolved in ethanol (22 mL) and 4 M sodium hydroxide solution (22 mL) was added. The mixture was stirred at room temperature for 3.5 h and the volume was reduced by ¾ under vacuum. The resulting mixture was diluted with water (50 mL) and acidified to pH 1-2 with 2 M hydrochloric acid. This mixture was extracted with dichloromethane (3×80 mL). The combined organic phases were washed with saturated brine (150 mL), dried (MgSO$_4$) and concentrated under reduced pressure to afford 3-[2-azido-2-(2-hydroxyethoxy)ethoxy]benzoic acid (2.20 g, 99%) as a colorless oil, which was used without further purification.

$^1$H NMR (300 MHz, CDCl$_3$) δ 7.76 (dt, 1H, J=7.7, 1.2 Hz, ArH), 7.65 (dd, 1H, J=2.4, 1.4 Hz, ArH), 7.41 (t, 1H, J=8.0 Hz, ArH), 7.19 (ddd, 1H, J=8.2, 2.7, 1.0 Hz, ArH), 4.90 (t, 1H, J=5.1 Hz, CH), 4.21 (m, 2H, ArOCH$_2$), 4.03 (m, 1H, 0.5×OCH$_2$), 3.81 (m, 3H, 0.5×OCH$_2$+OCH$_2$).

3-[2-Azido-2-(2-ethoxycarbonylmethoxyethoxy)ethoxy]benzoic acid

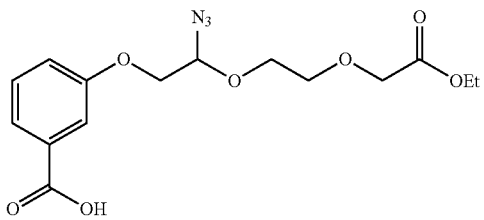 [SMILES: CCOC(=O)COCCOC(COc1cccc(C(=O)O)c1)N=[N+]=[N-]]

To an ice-cold solution of 3-[2-azido-2-(2-hydroxyethoxy)ethoxy]benzoic acid (2.20 g, 8.31 mmol) in anhydrous THF (25 mL) was added sodium hydride (0.99 g, 24.9 mmol) and the mixture was stirred at 0° C. for 10 min. Ethyl bromoacetate (3.05 g, 2.03 mL, 18.3 mmol) was added and the reaction mixture was allowed to warm up to room temperature over 5 h. The reaction was quenched with ice-water (20 mL) and washed with dichloromethane (2×100 mL). The aqueous layer was acidified to pH 1-2 by the addition of 2 M hydrochloric acid and was extracted with dichloromethane (3×50 mL). The combined organic layers were dried (MgSO$_4$) and concentrated under reduced pressure to afford a colorless oil. This crude material was purified using a Biotage Isolera automated chromatography system under normal phase conditions (silica column, gradient of 0→60% ethyl acetate in dichloromethane) with detection at 254 nm to give 3-[2-azido-2-(2-ethoxycarbonylmethoxyethoxy)ethoxy]benzoic acid (1.27 g, 43%), as a colorless oil.

R$_f$ 0.6 (ethyl acetate-dichloromethane, 4:6 v/v).

$^1$H NMR (300 MHz, CDCl$_3$) δ 7.75 (dt, 1H, J=7.7, 1.2 Hz, ArH), 7.64 (dd, 1H, J=2.7, 1.5 Hz, ArH), 7.40 (t, 1H, J=8.0 Hz, ArH), 7.19 (ddd, 1H, J=8.3, 2.7, 1.0 Hz, ArH), 4.95 (dd, 1H, J=5.5, 4.6 Hz, CH), 4.14 (m, 7H, ArOCH$_2$+0.5×OCH$_2$+OCH$_2$+OCH$_2$C(O)), 3.86 (m, 3H, 0.5×OCH$_2$+OCH$_2$), 1.28 (t, 3H, J=7.2 Hz, CH$_3$).

N-(2-Aminoethyl)-2,2,2-trifluoroacetamide Trifluoroacetate

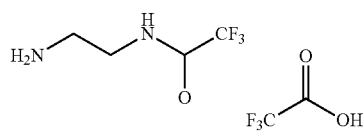 [SMILES: NCCNC(O)C(F)(F)F ; O=C(O)C(F)(F)F]

To an ice-cold solution of N-Boc-ethylenediamine (2.08 g, 2.05 mL, 13.0 mmol) in anhydrous THF (8 mL) was slowly added ethyl trifluoroacetate (1.85 g, 1.55 mL, 13.0 mmol) and the reaction mixture was stirred at room temperature overnight. The resulting solution was concentrated under reduced pressure to give tert-butyl [2-(2,2,2-trifluoroacetamido)ethyl]carbamate (3.30 g, 99%), as a white solid which was used without further purification.

tert-Butyl [2-(2,2,2-trifluoroacetamido)ethyl]carbamate (1.04 g, 4.06 mmol) was dissolved in trifluoroacetic acid (5 mL) and stirred at room temperature for 30 min. The resulting mixture was concentrated under reduced pressure and the residual trifluoroacetic acid was azeotropically removed with chloroform (3×10 mL). The material obtained was dried in vacuo at 50° C. for 2 h to give N-(2-aminoethyl)-2,2,2-trifluoroacetamide trifluoroacetate (1.07 g, 99%), as a yellow oil which was used without further purification.

$^1$H NMR (300 MHz, d$_6$-DMSO) δ 9.58 (br t, 1H, NH), 7.99 (br s, 3H, NH$_3^+$), 3.43 (m, 2H, CH$_2$N), 2.97 (m, 2H, CH$_2$N).

[2-(1-Azido-2-{3-[2-(2,2,2-trifluoroacetamido)ethylcarbamoyl]phenoxy}ethoxy)ethoxy]acetic acid ethyl ester

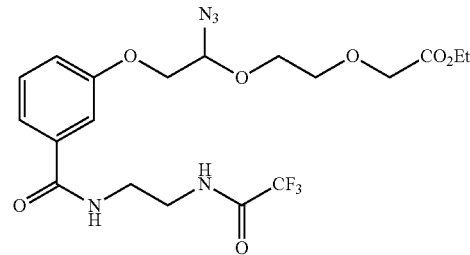 [SMILES: CCOC(=O)COCCOC(COc1cccc(C(=O)NCCNC(=O)C(F)(F)F)c1)N=[N+]=[N-]]

To a solution of N-(2-aminoethyl)-2,2,2-trifluoroacetamide trifluoroacetate (0.79 g, 2.94 mmol) in anhydrous DMF (15 mL) was added Hunig's base (0.95 g, 1.28 mL, 7.34 mmol), 3-[2-azido-2-(2-ethoxycarbonylmethoxyethoxy)ethoxy]benzoic acid (0.87 g, 2.45 mmol) and PyBOP (1.41 g, 2.69 mmol). The reaction mixture was stirred at room temperature overnight and was then quenched with 1 M hydrochloric acid (20 mL) and extracted with ethyl acetate (3×30 mL). The organic layers were combined, dried (MgSO$_4$) and concentrated under reduced pressure to give an orange oil. This oil was purified using a Biotage Isolera automated chromatography system under normal phase conditions (silica column, gradient of 0→90% ethyl acetate in dichloromethane) with detection at 254 nm to give [2-(1-azido-2-{3-[2-(2,2,2-trifluoroacetamido)ethylcarbamoyl]phenoxy}ethoxy)ethoxy]acetic acid ethyl ester (1.16 g, 96%), as a colorless oil.

R$_f$ 0.48 (dichloromethane-ethyl acetate, 1:1, v/v).

$^1$H NMR (300 MHz, CDCl$_3$) δ 8.01 (br, 1H, NH), 7.39 (m, 3H, 3×ArH), 7.10 (dt, 1H, J=5.8, 3.0 Hz, ArH), 6.97 (br, 1H, NH), 4.93 (t, 1H, J=5.1 Hz, CH), 4.18 (m, 6H, ArOCH$_2$+OCH$_2$+OCH$_2$C(O)), 4.04 (m, 1H, 0.5×OCH$_2$), 3.87 (m, 1H, 0.5×OCH$_2$), 3.81 (m, 2H, OCH$_2$), 3.69 (m, 2H, CH$_2$N), 3.62 (m, 2H, CH$_2$N), 1.30 (t, 3H, J=7.1 Hz, CH$_3$).

[2-(1-Azido-2-{3-[2-(tert-butoxycarbonyl)ethylcarbamoyl]phenoxy}ethoxy)ethoxy]acetic acid ethyl ester

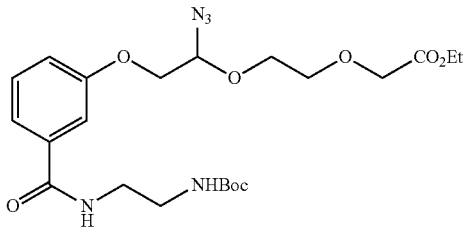 [SMILES: CCOC(=O)COCCOC(COc1cccc(C(=O)NCCNC(=O)OC(C)(C)C)c1)N=[N+]=[N-]]

To a solution of 3-[2-azido-2-(2-ethoxycarbonylmethoxyethoxy)ethoxy]benzoic acid (0.82 g, 2.33 mmol) in ethyl acetate (25 mL) was added N-Boc-ethylenediamine (410 mg, 0.41 mL, 2.56 mmol), PyBOP (1.34 g, 2.56 mmol) and Hunig's base (0.66 g, 0.41 mL, 5.12 mmol). The resulting reaction mixture was stirred at room temperature overnight. The solution was partitioned between ethyl acetate (20 mL) and 1 M hydrochloric acid (20 mL). The aqueous phase was separated and extracted with ethyl acetate (2×20 mL). The organic phases were combined and washed with saturated brine (50 mL), dried (MgSO4) and concentrated under reduced pressure to give a yellow oil. This oil was purified using a Biotage Isolera automated chromatography system under normal phase conditions (silica column, gradient of 0→80% ethyl acetate in dichloromethane) with detection at 254 nm. The fractions containing the product were combined and evaporated under reduced pressure. The material obtained was dissolved in ethyl acetate (50 mL) and washed with saturated aqueous sodium bicarbonate solution (50 mL), water (50 mL) and saturated brine (50 mL) before being dried (MgSO4) and concentrated under reduced pressure to give [2-(1-azido-2-{3-[2-(tert-butoxycarbonyl)ethylcarbamoyl]phenoxy}ethoxy)ethoxy]acetic acid ethyl ester (0.98 g, 86%) as a yellow oil.

$R_f$ 0.41 (dichloromethane-ethyl acetate, 1:1, v/v).

$^1$H NMR (300 MHz, CDCl$_3$) δ 7.42 (m, 2H, 2×ArH), 7.34 (t, 1H, J=7.8 Hz, ArH), 7.07 (m, 1H, ArH), 5.04 (br, 1H, NH), 4.94 (t, 1H, J=5.1 Hz, CH), 4.22 (m, 2H, OCH$_2$), 4.15 (m, 4H, ArOCH$_2$+OCH$_2$C(O)), 4.04 (m, 1H, 0.5×OCH$_2$), 3.88 (m, 1H, 0.5×OCH$_2$), 3.81 (m, 2H, OCH$_2$), 3.57 (m, 2H, CH$_2$N), 3.41 (m, 2H, CH$_2$N), 1.44 (s, 9H, 3×CH$_3$), 1.30 (t, 3H, J=7.1 Hz, CH$_3$).

Sodium (2-{2-[3-(2-aminoethylcarbamoyl)phenoxy]-1-azidoethoxy}ethoxy)acetate

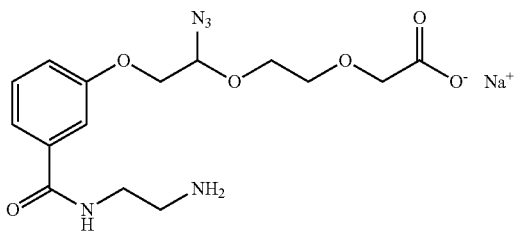 [SMILES: [N-]=[N+]=NC(COc1cccc(C(=O)NCCN)c1)OCCOCC(=O)[O-] ; [Na+]]

Method A
[2-(1-Azido-2-{3-[2-(2,2,2-trifluoroacetamido)ethylcarbamoyl]phenoxy}ethoxy)ethoxy]acetic acid ethyl ester;2q(1.16 g, 2.36 mmol) was dissolved in ethanol (7 mL) and 4 M sodium hydroxide solution (7 mL) was added. The resulting mixture was stirred at room temperature for 2.5 h before being concentrated under reduced pressure. The residue was dissolved in water (80 mL) and washed with dichloromethane (2×70 mL). The aqueous layer was acidified to pH 2 using 1 M hydrochloric acid and washed with dichloromethane (3×70 mL). The resulting aqueous layer was neutralised to pH 8 using 1 M sodium hydroxide solution and evaporated under reduced pressure to give a white solid which was entrained with dichloromethane and methanol (2×140 mL, 1:1, v/v). The solid obtained was collected by suction filtration and discarded. The filtrate was concentrated under reduced pressure to give a residual crude gum. This gum was entrained with dichloromethane and methanol (10 mL, 9:1, v/v) and the insoluble white solid obtained was collected by suction filtration and discarded. The filtrate was concentrated under reduced pressure to give sodium (2-{2-[3-(2-aminoethylcarbamoyl)phenoxy]-1-azidoethoxy}ethoxy)acetate (1.11 g, 100%), as a white glassy foam.

Method B
To a solution of [2-(1-azido-2-{3-[2-(tert-butoxycarbonyl)ethylcarbamoyl]phenoxy}ethoxy)ethoxy]acetic acid ethyl ester (0.59 g, 1.20 mmol) in ethanol (4 mL) was added 4 M sodium hydroxide solution (4 mL) and the mixture was stirred for 2.5 h. The solution was concentrated under reduced pressure and the residue was dissolved in water (15 mL). This aqueous mixture was acidified to pH 1-2 using 2 M hydrochloric acid and was extracted with dichloromethane (3×20 mL). The combined organic layers were dried (MgSO$_4$) and then concentrated under reduced pressure to give [2-(1-azido-2-{3-[2-(tert-butoxycarbonyl)ethylcarbamoyl]phenoxy}ethoxy)ethoxy]acetic acid (0.52 g, 92%), as a colorless oil.

To a solution of [2-(1-azido-2-{3-[2-(tert-butoxycarbonyl)ethylcarbamoyl]phenoxy}ethoxy)ethoxy]acetic acid (50 mg, 0.11 mmol) in dichloromethane (1.5 mL) was added trifluoroacetic acid (80 µL) and the mixture was stirred at room temperature for 40 min. The solution was concentrated under reduced pressure to afford a colorless oil. This oil was partitioned between dichloromethane (2 mL) and 1 M hydrochloric acid (2 mL). The organic layer was discarded and the aqueous layer was adjusted to pH 8 using 3 M sodium hydroxide solution before being concentrated under reduced pressure. The white solid obtained was entrained with a mixture of dichloromethane and methanol (2×10 mL, 1:1, v/v) and the precipitate was discarded. The filtrate was evaporated and the residue was entrained with a mixture of dichloromethane and methanol (10 mL, 9:1, v/v) and the precipitate was discarded. The filtrate was concentrated under reduced pressure to give sodium (2-{2-[3-(2-aminoethylcarbamoyl)phenoxy]-1-azidoethoxy}ethoxy)acetate (43 mg, 99%), as a white glassy solid.

$^1$H NMR (300 MHz, D$_2$O) δ 7.31 (m, 3H, 3×ArH), 7.11 (ddd, 1H, J=7.8, 2.6, 1.5 Hz, ArH), 4.99 (t, 1H, J=4.5 Hz, CH), 4.15 (m, 2H, ArOCH$_2$), 3.94 (m, 1H, 0.5×OCH$_2$), 3.79 (m, 3H, 0.5×OCH$_2$+OCH$_2$C(O)), 3.58 (m, 4H, OCH$_2$+CH$_2$N), 3.10 (t, 2H, J=5.8 Hz CH$_2$N), 1.30 (t, 3H, J=7.1 Hz, CH$_3$).

2-(2-{1-Azido-2-[3-({2-[3,5-bis(methoxycarbonyl)benzamido]ethyl}carbamoyl)phenoxy]ethoxy}ethoxy)acetic acid (Fragment 2)

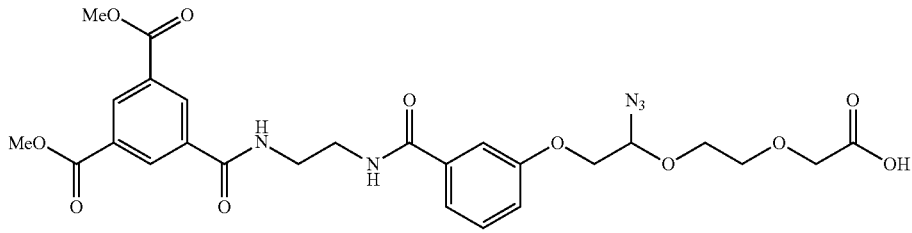 [SMILES: COC(=O)c1cc(C(=O)NCCNC(=O)c2cccc(OCC(N=[N+]=[N-])OCCOCC(=O)O)c2)cc(C(=O)OC)c1]

Trimethyl 1,3,5-benzenetricarboxylate (2.00 g, 7.93 mmol) was suspended in methanol (180 mL) and 1 M sodium hydroxide solution (7.14 mL) was added. The mixture was stirred at room temperature for 18 h. The resulting solution was concentrated under reduced pressure to afford a white solid which was partitioned between dichloromethane (150 mL) and saturated aqueous sodium bicarbonate solution (150 mL). The organic phase was separated and was extracted with saturated aqueous sodium bicarbonate solution (150 mL) before being discarded. The combined aqueous layers were acidified to pH 1-2 using concentrated hydrochloric acid and were extracted with ethyl acetate (2×150 mL). The combined organic layers were dried (MgSO$_4$) and concentrated to give 3,5-bis(methoxycarbonyl)benzoic acid (1.66 g, 88%), as a white solid.

3,5-bis(Methoxycarbonyl)benzoic acid (0.80 g, 3.36 mmol) was dissolved in ethyl acetate (20 mL) and N-hydroxysuccinimide (425 mg, 3.69 mmol) was added followed by N,N'-dicyclohexylcarbodiimide (0.76 g, 3.69 mmol). The resulting mixture was stirred at room temperature for 20 h. The suspension was filtered over Celite and the filtrate was washed with saturated aqueous sodium bicarbonate solution (2×100 mL), water (100 mL) and saturated brine (100 mL). The organic layer was dried (MgSO$_4$) and concentrated under reduced pressure to afford a white glassy solid. This material was purified using a Biotage Isolera automated chromatography system under normal phase conditions (silica column, gradient of 0→100% ethyl acetate in petrol) with detection at 254 nm to give N-hydroxysuccinimide 3,5-bis(methoxycarbonyl)benzoate (1.06 g, 95%), as a white solid.

R$_f$ 0.44 (petrol-ethyl acetate, 4:6, v/v).

To a solution of N-hydroxysuccinimide 3,5-bis(methoxycarbonyl)benzoate (0.95 g, 2.83 mmol) and sodium (2-{2-[3-(2-aminoethylcarbamoyl)phenoxy]-1-azidoethoxy}ethoxy)acetate (0.92 g, 2.36 mmol) in anhydrous DMF (15 mL) was added Hunig's base (0.61 g, 0.83 mL, 4.72 mmol) and the mixture was stirred at room temperature overnight. The resulting mixture was diluted with ethyl acetate (20 mL) and quenched with 1 M hydrochloric acid (20 mL). The aqueous phase was separated and was extracted with ethyl acetate (3×30 mL) and the combined organic phases were washed with water (5×50 mL) and saturated brine (50 mL). The resulting solution was dried (MgSO$_4$) before being concentrated under reduced pressure to give a white glassy solid. This material was purified using a Biotage Isolera automated chromatography system under normal phase conditions (silica column, gradient of 0→50% methanol in dichloromethane) with detection at 254 nm to give 2-(2-{1-azido-2-[3-({2-[3,5-bis(methoxycarbonyl)benzamido]ethyl}carbamoyl)phenoxy]ethoxy}ethoxy)acetic acid (Fragment 2) (0.92 g, 66%), as a white glassy solid.

R$_f$ 0.37 (dichloromethane-methanol, 83:17, v/v).

$^1$H NMR (300 MHz, d$_6$-DMSO) δ 9.42 (br s, 1H, NH), 8.99 (br s, 1H, NH), 8.66 (d, 2H, J=1.5 Hz, 2×ArH), 8.53 (t, 1H, J=1.5 Hz, ArH), 7.50 (m, 1H, ArH), 7.43 (d, 1H, J=7.7 Hz, ArH), 7.33 (t, 1H, J=7.9 Hz, ArH), 7.07 (dd, 1H, J=8.0, 2.4 Hz, ArH), 5.21 (t, 1H, J=5.0 Hz, CH), 4.24 (dd, 1H, J=10.6, 4.4 Hz, 0.5×ArOCH$_2$), 4.07 (dd, 1H, J=10.6, 5.9 Hz, 0.5×ArOCH$_2$), 3.88 (m, 8H, OCH$_2$+2×OCH$_3$), 3.84 (m, 1H, 0.5×OCH$_2$), 3.77 (m, 1H, 0.5×OCH$_2$), 3.62 (m, 2H, OCH$_2$C(O)), 3.40 (m, 4H, 2×CH$_2$N).

Pre-Cleavable SCTTP

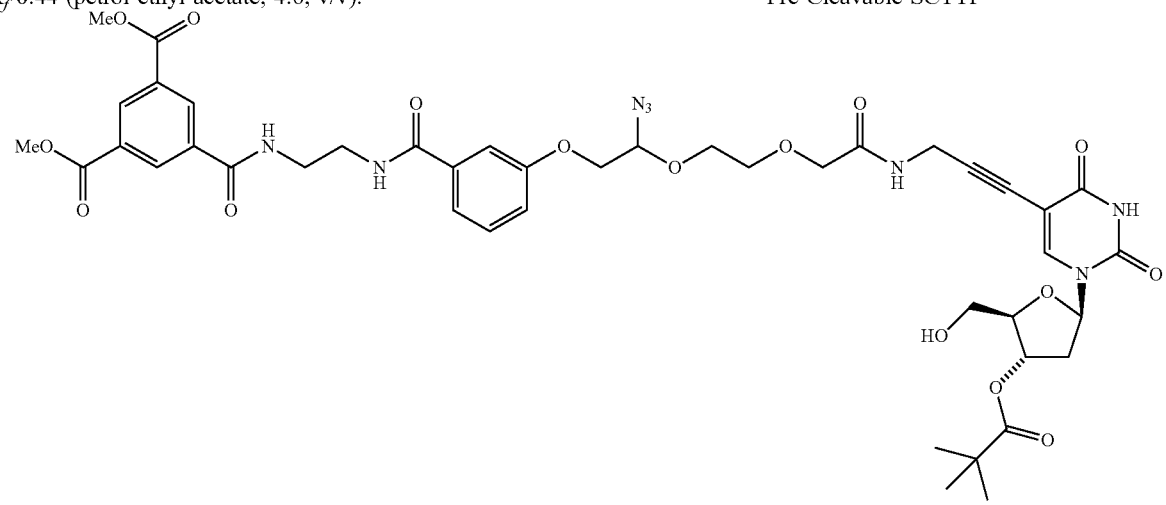

3'-O-Pivaloyl-5-(3-aminopropynyl)-2'-deoxyuridine trifluoroacetate (1.04 g, 2.16 mmol) was dissolved in anhydrous DMF (20 mL). Hunig's base (0.80 g, 1.08 mL, 6.18 mmol) followed by 2-(2-{1-azido-2-[3-({2-[3,5-bis(methoxycarbonyl)benzamido]ethyl}carbamoyl)phenoxy]ethoxy}ethoxy)acetic acid (0.91 g, 1.55 mmol) and HBTU (0.62 g, 1.62 mmol) were then added. The reaction mixture was stirred at room temperature for 20 h. and was quenched with 1 M hydrochloric acid (20 mL) and diluted with ethyl acetate (20 mL). The aqueous phase was separated and extracted with ethyl acetate (2×50 mL). The combined organic phases were washed with water (5×60 mL), saturated aqueous sodium bicarbonate solution (60 mL) and brine (60 mL), before being dried (MgSO$_4$) and concentrated under reduced pressure to give an off-white solid. This solid was purified using a Biotage Isolera automated chromatography system under normal phase conditions (silica column, gradient of 0→10% methanol in dichloromethane) with detection at 254 nm to afford Pre-Cleavable SCTTP (1.20 g, 83%), as an off-white solid.

R$_f$ 0.42 (dichloromethane-methanol, 92:8, v/v).

$^1$H NMR (300 MHz, d$_6$-DMSO) δ 11.69 (s, 1H, deoxyuridine NH), 9.09 (br t, 1H, NH), 8.68 (d, 2H, J=1.6 Hz, 2×ArH), 8.64 (br t, 1H, NH), 8.58 (t, 1H, J=1.6 Hz, ArH), 8.26 (t, 1H, J=5.8 Hz, NH), 8.16 (s, 1H, deoxyuridine CH), 7.46 (m, 2H, 2×ArH), 7.38 (t, 1H, J=7.8 Hz, ArH), 7.13 (m, 1H, ArH), 6.12 (dd, 1H, J=8.3, 6.0 Hz, CH), 5.27 (m, 1H, CHN), 5.16 (m, 2H, CHOPiv+OH), 4.23 (dd, 1H, J=10.4, 4.5 Hz, 0.5×ArOCH$_2$), 4.13 (m, 2H, 0.5×ArOCH$_2$+0.5×OCH$_2$), 3.88 (m, 10H, CH$_2$N+OCH$_2$+2×OCH$_3$), 3.85 (m, 1H, 0.5×OCH$_2$), 3.68 (m, 2H, deoxyuridine CH$_2$), 3.63 (m, 2H, OCH$_2$C(O)), 3.46 (m, 4H, 2×CH$_2$N), 2.27 (m, 2H, deoxyuridine CH$_2$), 1.15 (s, 9H, 3×CH$_3$).

Penta-Triethylammonium Cleavable SCTTP

Pre-Cleavable SCTTP (390 mg, 0.42 mmol) was dissolved in 1,4-dioxane (0.39 mL) and pyridine (1.2 mL) and the flask was evacuated and purged with a nitrogen atmosphere. 1.0 M Salicyl chlorophosphite solution in 1,4-dioxane (460 µL, L, 0.46 mmol) was added and the reaction mixture was stirred for 10 min. 0.5 M Tributylammonium pyrophosphate solution in DMF (1.25 mL, 0.63 mmol) and tributylamine (358 mg, 460 µL, 1.93 mmol) were added and the reaction mixture was stirred for 20 min. 1% Iodine solution in pyridine and water (8.4 mL, 98:2) was added and the solution was stirred for 15 min before being quenched with 5% aqueous sodium thiosulfate solution (1 mL) and concentrated under reduced pressure. The material obtained was purified using a Biotage Isolera automated chromatography system under reversed-phase conditions (C$_{18}$ column, gradient of 0→40% acetonitrile in 0.1 M TEAA at pH 7.0) with detection at 287 nm to afford, after freeze-drying, impure protected Cleavable SCTTP (360 mg) which was used without further purification.

Protected Cleavable SCTTP (360 mg) was dissolved in water (3.0 mL) and the resulting solution was stirred for 15 min before addition of 1 M sodium hydroxide solution (3.0 mL). The mixture was stirred at room temperature for 2 h and was quenched with 1 M aqueous triethylammonium bicarbonate (TEAB) solution (pH 8.5, 10 mL). The resulting solution was lyophilized overnight and the residue was dissolved in water (4 mL) to give a concentration of 100 mg/mL. This solution was purified by semi-preparative HPLC injecting 100 µL portions and collecting the eluent containing the pure substance. The combined fractions were reduced in volume by removing the acetonitrile and most of the water and finally lyophilized to give penta-triethylammonium Cleavable SCTTP (233 mg, 35 over two steps), as a white solid.

HPLC Conditions

Column: Phenomenex Luna C18(2), 15 mm×250 mm

Solvent Gradient: 90% 0.1 M aqueous TEAB to 84.5% 0.1 M aqueous TEAB over 22 min with the balance being acetonitrile.

Flow Rate: 7.8 mL/min

Temp: 30° C.

Detection: UV at 287 nm

Under these conditions the product had a retention time of ca. 17-19 min.

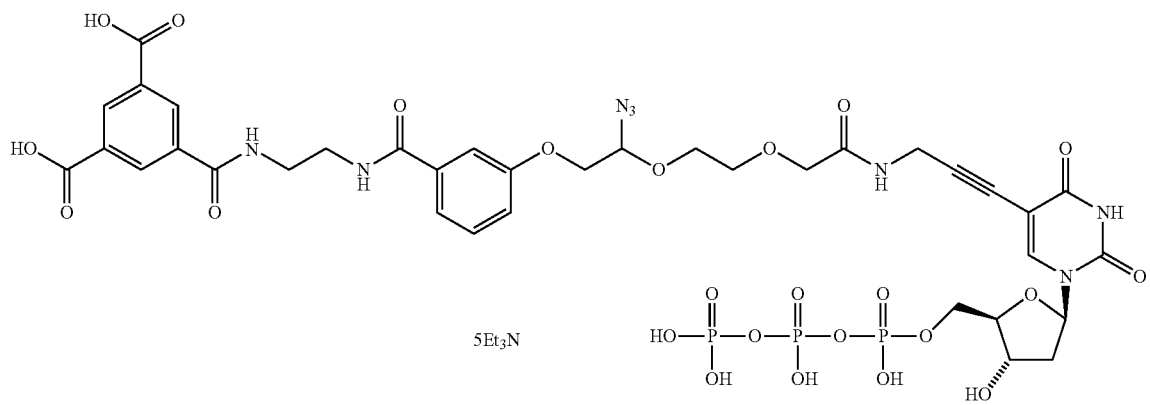 [SMILES: [N-]=[N+]=NC(COc1cccc(C(=O)NCCNC(=O)c2cc(C(=O)O)cc(C(=O)O)c2)c1)OCCOCC(=O)NCC#Cc1cn([C@H]2C[C@H](O)[C@@H](COP(=O)(O)OP(=O)(O)OP(=O)(O)O)O2)c(=O)[nH]c1=O]

Example 5

Synthesis of Supercharged CTP (SCCTP)

5'-O-Dimethoxytrityl-5-iodo-2'-deoxycytidine

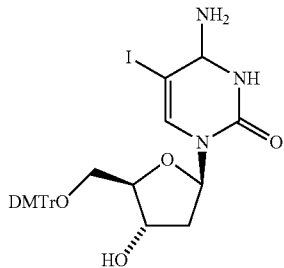

5-Iodo-2'-deoxycytidine (500 mg, 1.42 mmol) was dissolved in anhydrous pyridine (6.0 mL) and stirred under nitrogen. After 5 min, 4-(dimethylamino)pyridine (10 mg, 0.08 mmol) and triethylamine (22 mg, 30 µL, 0.21 mmol) were added to the reaction mixture, followed by 4,4'-dimethoxytriphenylmethyl chloride (576 mg, 1.70 mmol). The resulting mixture was stirred overnight at room temperature and quenched with methanol (~1.0 mL) before being concentrated under reduced pressure. The residue obtained was partitioned between a saturated aqueous sodium bicarbonate solution (25 mL) and dichloromethane (25 mL). The layers were separated and the aqueous phase was extracted with dichloromethane (25 mL). The organic phases were combined, dried ($MgSO_4$) and concentrated under reduced pressure to give a yellow semi-solid. This crude material was purified using a Biotage Isolera automated chromatography system under normal phase conditions (silica column, gradient of 1.5→24% methanol in dichloromethane) with detection at 254 nm to give 5'-O-dimethoxytrityl-5-iodo-2'-deoxycytidine (0.58 g, 62%), as a white solid.

$R_f$ 0.35 (dichloromethane-methanol, 94:6, v/v).

$^1$H NMR (300 MHz, $d_6$-DMSO): 7.97 (s, 1H, CH), 7.89 (br, 1H, 0.5×$NH_2$), 7.32 (m, 9H, 9×ArH), 6.91 (m, 4H, 4×ArH), 6.66 (br, 1H, 0.5×$NH_2$), 6.11 (t, J=6.7 Hz, 1H, CH), 5.29 (d, J=4.1 Hz, 1H, OH), 4.20 (m, 1H, CH), 3.91 (m, 1H, CH), 3.74 (s, 6H, 2×$OCH_3$), 3.17 (m, 2H, $CH_2$), 2.21 (m, 1H, 0.5×$CH_2$), 2.09 (m, 1H, 0.5×$CH_2$).

4-N-3'-O-Di-pivaloyl-5'-O-dimethoxytrityl-5-iodo-2'-deoxycytidine

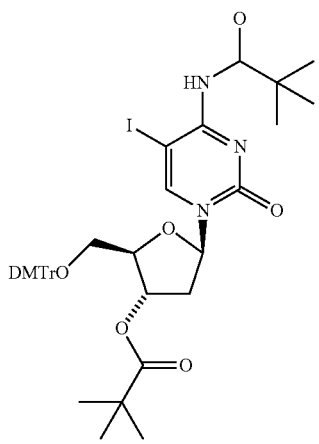

5'-O-Dimethoxytrityl-5-iodo-2'-deoxycytidine (0.57 g, 0.87 mmol) was dissolved in anhydrous acetonitrile (11.4 mL). 4-(Dimethylamino)pyridine (21 mg, 0.17 mmol) and triethylamine (369 mg, 0.51 mL, 3.65 mmol) followed by trimethylacetic anhydride (0.65 g, 0.71 mL, 3.48 mmol) were added. The reaction mixture was stirred and heated at reflux for 20 h under nitrogen, then allowed to cool to room temperature and methanol (~1.0 mL) was added. The resulting solution was concentrated under reduced pressure to give a crude residue which was purified using a Biotage Isolera automated chromatography system under normal phase conditions (silica column, gradient of 3→30% ethyl acetate in petrol) with detection at 254 nm to give 4-N-3'-O-di-pivaloyl-5'-O-dimethoxytrityl-5-iodo-2'-deoxycytidine (0.70 g, 97%), as a colorless oil which solidified on standing.

$R_f$ 0.32 (petrol-ethyl acetate, 85:15, v/v).

$^1$H NMR (300 MHz, $d_6$-DMSO): 7.32 (m, 9H, 9×ArH), 6.90 (m, 4H, 4×ArH), 6.08 (t, J=6.8 Hz, 1H, CH), 5.21 (m, 1H, CH), 4.04 (m, 1H, CH), 3.74 (s, 6H, 2×$OCH_3$), 3.30 (obscured, 2H, $CH_2$), 2.40 (obscured, 2H, $CH_2$), 1.19 (s, 9H, 3×$CH_3$), 1.13 (s, 9H, 3×$CH_3$).

3'-O-Pivaloyl-5'-O-dimethoxytrityl-5-iodo-2'-deoxycytidine

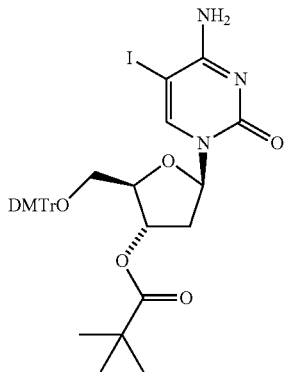

4-N-3'-O-Di-pivaloyl-5'-O-dimethoxytrityl-5-iodo-2'-deoxycytidine (0.70 g, 0.85 mmol) was dissolved in anhydrous methanol (8.8 mL) and Hunig's base (165 mg, 221 µL, 1.28 mmol) was added. The reaction mixture was heated in a sealed vial at ~110° C. for 3 h before being concentrated under reduced pressure. The resulting impure material was purified using a Biotage Isolera automated chromatography system under normal phase conditions (silica column, gradient of 1→10% methanol in dichloromethane) with detection at 254 nm to give 3'-O-pivaloyl-5'-O-dimethoxytrityl-5-iodo-2'-deoxycytidine (0.50 g, 80%), as a white solid.

$R_f$ 0.33 (dichloromethane-methanol, 96:4, v/v).

$^1$H NMR (300 MHz, $d_6$-DMSO): δ 8.02 (s, 1H, CH), 7.94 (br, 1H, 0.5×$NH_2$), 7.33 (m, 9H, 9×ArH), 6.90 (m, 4H, 4×ArH), 6.73 (br, 1H, 0.5×$NH_2$), 6.12 (t, J=7.0 Hz, 1H, CH), 5.19 (m, 1H, CH), 3.98 (m, 1H, CH), 3.74 (s, 6H, 2×$OCH_3$), 3.27 (m, 2H, $CH_2$), 2.33 (m, 2H, $CH_2$), 1.13 (s, 9H, 3×$CH_3$).

3'-O-Pivaloyl-5'-O-dimethoxytrityl-5-(N-Boc-3-amido-propynyl)-2'-deoxycytidine

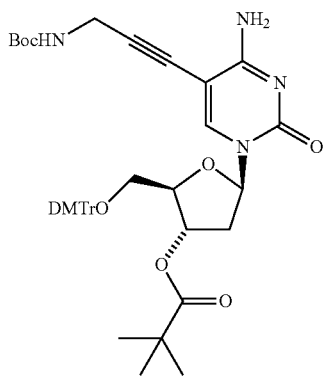

3'-O-Pivaloyl-5'-O-dimethoxytrityl-5-iodo-2'-deoxycytidine (0.50 g, 0.68 mmol), copper(I) iodide (26 mg, 0.14 mmol) and tetrakis(triphenylphosphine)palladium(0) (81 mg, 0.07 mmol) were dissolved in ethyl acetate (5.9 mL) and the flask was evacuated then purged with nitrogen four times. Hunig's base (175 mg, 230 µL, 1.35 mmol) and N-Boc-propargylamine (315 mg, 2.03 mmol) were added and the resulting mixture was evacuated and purged with nitrogen before being left to stir at room temperature overnight. The reaction mixture was diluted with ethyl acetate (25 mL) and washed with 5% aqueous EDTA solution (25 mL). The layers were separated and the aqueous phase was washed with ethyl acetate (10 mL). The combined organic layers were washed with saturated brine (25 mL), dried (MgSO$_4$) and concentrated under reduced pressure to give an orange solid. This solid was purified using a Biotage Isolera automated chromatography system under normal phase conditions (silica column, gradient of 1→13% methanol in dichloromethane) with detection at 254 nm to give 3'-O-pivaloyl-5'-O-dimethoxytrityl-5-(N-Boc-3-amido-propynyl)-2'-deoxycytidine (470 mg, 91%), as a pale yellow solid.

R$_f$ 0.33 (dichloromethane-methanol, 96:4, v/v).

$^1$H NMR (300 MHz, d$_6$-DMSO): δ 7.94 (s, 1H, CH), 7.92 (br, 1H, 0.5×NH$_2$), 7.31 (m, 9H, 9×ArH), 6.89 (m, 5H, 4×ArH+0.5×NH$_2$), 6.15 (t, J=7.0 Hz, 1H, CH), 5.23 (m, 1H, CH), 4.02 (m, 1H, CH), 3.85 (m, 2H, CH$_2$), 3.74 (s, 6H, 2×OCH$_3$), 3.38 (obscured, 1H, 0.5×CH$_2$), 3.17 (m, 1H, 0.5×CH$_2$), 2.35 (m, 2H, CH$_2$), 1.38 (s, 9H, 3×CH$_3$), 1.13 (s, 9H, 3×CH$_3$).

3'-O-Pivaloyl-5-(3-aminopropynyl)-2'-deoxycytidine Trifluoroacetate

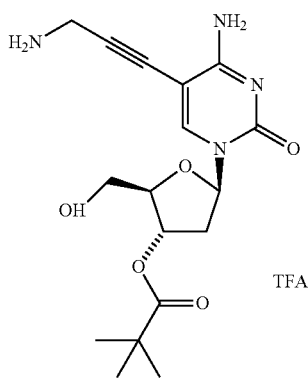 [SMILES: CC(C)(C)C(=O)O[C@H]1C[C@H](n2cc(C#CCN)c(N)nc2=O)O[C@@H]1CO]

3'-O-Pivaloyl-5'-O-dimethoxytrityl-5-(N-Boc-3-amido-propynyl)-2'-deoxycytidine (465 mg, 0.61 mmol) was dissolved in anhydrous dichloromethane (11.9 mL) and trifluoroacetic acid (2.77 g, 1.87 mL, 24.3 mmol) was added dropwise. The mixture was stirred for 2 h at room temperature and was subsequently diluted with dichloromethane (20 mL). The resulting solution was concentrated under reduced pressure and the residual trifluoroacetic acid was azeotropically removed with dichloromethane (3×20 mL). The impure material was purified using a Biotage Isolera automated chromatography system under reversed-phase conditions (C$_{18}$ column, gradient of 0→40% acetonitrile in 0.1% aqueous trifluoroacetic acid) with detection at 254 nm to afford, after freeze-drying, 3'-O-pivaloyl-5-(3-aminopropynyl)-2'-deoxycytidine trifluoroacetate (Fragment 1) (269 mg, 92%), as an off-white solid.

$^1$H NMR (300 MHz, DMSO-d$_6$): δ 8.33 (br, 1H, 0.5× NH$_2$), 8.27 (s, 1H, CH), 8.24 (br, 3H, NH$_3^+$), 7.32 (br, 1H, 0.5×NH$_2$), 6.14 (m, 1H, CH), 5.19 (m, 1H, CH), 3.98 (m, 3H, CH+CH$_2$), 3.64 (m, 2H, CH$_2$), 2.28 (m, 2H, CH$_2$), 1.17 (s, 9H, 3×CH$_3$).

3-[(1,3)Dioxolan-2-ylmethoxy]benzoic acid ethyl ester

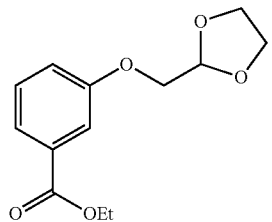 [SMILES: CCOC(=O)c1cccc(OCC2OCCO2)c1]

Ethyl 3-hydroxybenzoate (3.50 g, 21.1 mmol), bromoethyl-1,3-dioxolane (14.1 g, 8.72 mL, 84.3 mmol), potassium carbonate (5.83 g, 42.1 mmol) and sodium iodide (1.26 g, 8.43 mmol) were dissolved in anhydrous DMF (10 mL) and the reaction mixture was stirred at 120° C. for 20 h. The suspension was cooled to room temperature and quenched with water (30 mL). The aqueous phase was extracted with ethyl acetate (3×50 mL). The organic layers were combined, washed with water (5×100 mL) and saturated brine (100 mL), before being dried (MgSO$_4$) and concentrated under reduced pressure to afford a residual orange oil. This oil was purified using a Biotage Isolera automated chromatography system under normal phase conditions (silica column, gradient of 0→30% ethyl acetate in petrol) with detection at 254 nm to give 3-[(1,3)dioxolan-2-ylmethoxy]benzoic acid ethyl ester (5.09 g, 96%), as a colorless oil.

R$_f$ 0.40 (petrol-ethyl acetate, 75:25, v/v).

$^1$H NMR (400 MHz, CDCl$_3$): δ 7.66 (dt, J=7.5, 1.1 Hz, 1H, ArH), 7.59 (dd, J=2.6, 1.5 Hz, 1H, ArH), 7.34 (t, J=7.9 Hz, 1H, ArH), 7.14 (ddd, J=8.3, 2.6, 1.0 Hz, 1H, ArH), 5.31 (t, J=4.1 Hz, 1H, CH), 4.36 (q, J=7.2 Hz, 2H, OCH$_2$), 4.02 (m, 6H, OCH$_2$CH$_2$O+ArOCH$_2$), 1.39 (t, J=7.1 Hz, 3H, CH$_3$).

3-[2-Azido-2-(2-hydroxyethoxy)ethoxy]benzoic acid ethyl ester

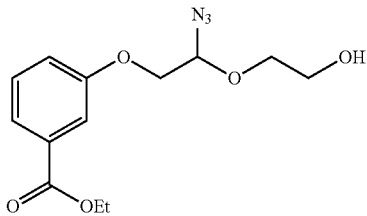

To a mixture of 3-[(1,3)dioxolan-2-ylmethoxy]benzoic acid ethyl ester (5.08 g, 20.1 mmol) and azidotrimethylsilane (2.55 g, 2.94 mL, 22.2 mmol) was added tin(IV) chloride (336 mg, 151 µL, 1.29 mmol). The reaction mixture was stirred at room temperature for 2 h. The resulting mixture was diluted with 2% aqueous methanol (60 mL) and stirred for 30 min before being concentrated under reduced pressure. The residue was azeotropically dried with ethanol (2×30 mL) to afford a colorless oil. This oil was purified using a Biotage Isolera automated chromatography system under normal phase conditions (silica column, gradient of 0→70% ethyl acetate in petrol) with detection at 254 nm to give 3-[2-azido-2-(2-hydroxyethoxy)ethoxy]benzoic acid ethyl ester (3.59 g, 59%), as a colorless oil.

$R_f$ 0.41 (petrol-ethyl acetate, 53:47, v/v).

$^1$H NMR (300 MHz, CDCl$_3$): δ 7.69 (dt, J=7.7, 1.2 Hz, 1H, ArH), 7.59 (dd, J=2.6, 1.5 Hz, 1H, ArH), 7.36 (t, J=8.0 Hz, 1H, ArH), 7.13 (ddd, J=8.3, 2.7, 1.0 Hz, 1H, ArH), 4.89 (t, J=5.1 Hz, 1H, CH), 4.38 (q, J=7.1 Hz, 2H, OCH$_2$), 4.19 (m, 2H, ArOCH$_2$), 4.00 (m, 1H, 0.5×OCH$_2$), 3.80 (m, 3H, 0.5×OCH$_2$+OCH$_2$), 1.40 (t, J=7.1 Hz, 3H, CH$_3$).

3-[2-Azido-2-(2-hydroxyethoxy)ethoxy]benzoic acid

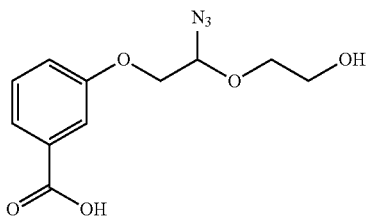 [SMILES: [N-]=[N+]=NC(COc1cccc(C(=O)O)c1)OCCO]

3-[2-Azido-2-(2-hydroxyethoxy)ethoxy]benzoic acid ethyl ester (3.51 g, 11.9 mmol) was dissolved in ethanol (30 mL) and 4 M aqueous sodium hydroxide (30 mL) was added. The mixture was stirred at room temperature for 3.5 h and the volume was then reduced by ¾ under vacuum. The resulting mixture was diluted with water (50 mL) and acidified to pH 1-2 with 2 M hydrochloric acid. This mixture was extracted with dichloromethane (3×100 mL). The combined organic phases were washed with saturated brine (150 mL), dried (MgSO$_4$) and concentrated under reduced pressure to afford 3-[2-azido-2-(2-hydroxyethoxy)ethoxy]benzoic acid (3.39 g, quantitative), as a colorless oil which was used without further purification.

$^1$H NMR (300 MHz, CDCl$_3$): δ 7.76 (dt, J=7.7, 1.2 Hz, 1H, ArH), 7.65 (dd, J=2.4, 1.4 Hz, 1H, ArH), 7.41 (t, J=8.0 Hz, 1H, ArH), 7.19 (ddd, J=8.2, 2.7, 1.0 Hz, 1H, ArH), 4.90 (t, J=5.1 Hz, 1H, CH), 4.21 (m, 2H, ArOCH$_2$), 4.03 (m, 1H, 0.5×OCH$_2$), 3.81 (m, 3H, 0.5×OCH$_2$+OCH$_2$).

3-[2-Azido-2-(2-ethoxycarbonylmethoxyethoxy)ethoxy]benzoic acid

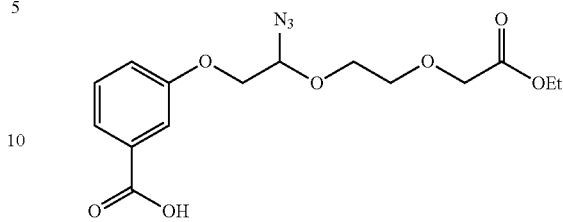

To an ice-cold solution of 3-[2-azido-2-(2-hydroxyethoxy)ethoxy]benzoic acid (1.42 g, 5.31 mmol) in anhydrous THF (18 mL) was added sodium hydride (0.64 g, 15.9 mmol) and the mixture was stirred at 0° C. for 10 min. Ethyl bromoacetate (1.95 g, 1.30 mL, 11.7 mmol) was added and the reaction mixture was allowed to warm up to room temperature over 5 h. The resulting mixture was quenched with ice-water (20 mL) and washed with dichloromethane (2×70 mL). The aqueous layer was acidified to pH 1-2 using 2 M hydrochloric acid and was extracted with dichloromethane (3×70 mL). The combined organic layers were dried (MgSO$_4$) and concentrated under reduced pressure to afford a colorless oil. This material was purified using a Biotage Isolera automated chromatography system under normal phase conditions (silica column, gradient of 0→60% ethyl acetate in dichloromethane) with detection at 254 nm to give 3-[2-azido-2-(2-ethoxycarbonylmethoxyethoxy)ethoxy]benzoic acid (0.62 g, 33%), as a colorless oil.

$R_f$ 0.45 (ethyl acetate-dichloromethane, 4:6 v/v).

$^1$H NMR (300 MHz, CDCl$_3$): δ 7.75 (dt, J=7.7, 1.2 Hz, 1H, ArH), 7.64 (dd, J=2.7, 1.5 Hz, 1H, ArH), 7.40 (t, J=8.0 Hz, 1H, ArH), 7.19 (ddd, J=8.3, 2.7, 1.0 Hz, 1H, ArH), 4.95 (dd, J=5.5, 4.6 Hz, 1H, CH), 4.14 (m, 7H, ArOCH$_2$+0.5× OCH$_2$+OCH$_2$+OCH$_2$C(O)), 3.86 (m, 3H, 0.5×OCH$_2$+ OCH$_2$), 1.28 (t, J=7.2 Hz, 3H, CH$_3$).

N-(2-Aminoethyl)-2,2,2-trifluoroacetamide Trifluoroacetate

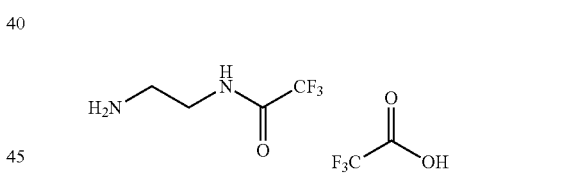

To an ice-cold solution of N-Boc-ethylenediamine (2.08 g, 2.05 mL, 13.0 mmol) in anhydrous THF (8 mL) was slowly added ethyl trifluoroacetate (1.85 g, 1.55 mL, 13.0 mmol) and the reaction mixture was stirred at room temperature overnight. The resulting solution was concentrated under reduced pressure to give tert-butyl [2-(2,2,2-trifluoroacetamido)ethyl]carbamate (3.30 g, 99%), as a white solid which was used without further purification.

tert-Butyl [2-(2,2,2-trifluoroacetamido)ethyl]carbamate (1.04 g, 4.06 mmol) was dissolved in trifluoroacetic acid (5 mL) and stirred at room temperature for 30 min. The resulting mixture was concentrated under reduced pressure and the residual trifluoroacetic acid was azeotropically removed with chloroform (3×10 mL). The material obtained was dried in vacuo at 50° C. for 2 h to give N-(2-aminoethyl)-2,2,2-trifluoroacetamide trifluoroacetate (1.07 g, 99%), as a yellow oil which was used without further purification.

$^1$H NMR (300 MHz, DMSO-d$_6$): δ 9.58 (br, 1H, NH), 7.99 (br, 3H, NH$_3^+$), 3.43 (m, 2H, CH$_2$N), 2.97 (m, 2H, CH$_2$N).

[2-(1-Azido-2-{3-[2-(2,2,2-trifluoroacetamido)ethyl-carbamoyl]phenoxy}ethoxy)ethoxy]acetic acid ethyl ester

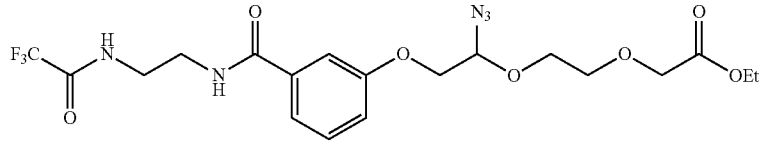 [SMILES: CCOC(=O)COCCOC(COc1cccc(C(=O)NCCNC(=O)C(F)(F)F)c1)N=[N+]=[N-]]

To a solution of N-(2-aminoethyl)-2,2,2-trifluoroacetamide trifluoroacetate (1.31 g, 4.86 mmol) in anhydrous DMF (25 mL) was added Hunig's base (1.57 g, 2.12 mL, 12.1 mmol), 3-[2-azido-2-(2-ethoxycarbonylmethoxyethoxy)ethoxy]benzoic acid (1.43 g, 4.05 mmol) and PyBOP (2.32 g, 4.45 mmol). The reaction mixture was stirred at room temperature for 20 h before being diluted with ethyl acetate (20 mL) and quenched with 1 M hydrochloric acid (40 mL). The aqueous phase was extracted with ethyl acetate (3×50 mL). The combined organic layers were washed with water (5×100 mL), saturated brine (100 mL), dried (MgSO$_4$) and concentrated under reduced pressure to give a residual yellow oil. This oil was purified using a Biotage Isolera automated chromatography system under normal phase conditions (silica column, gradient of 0→90% ethyl acetate in dichloromethane) with detection at 254 nm to give [2-(1-azido-2-{3-[2-(2,2,2-trifluoroacetamido)ethylcarbamoyl]phenoxy}ethoxy)ethoxy]acetic acid ethyl ester (1.75 g, 88%), as a colorless oil.

R$_f$ 0.48 (dichloromethane-ethyl acetate, 1:1, v/v).

$^1$H NMR (300 MHz, CDCl$_3$): δ 8.01 (br, 1H, NH), 7.39 (m, 3H, 3×ArH), 7.10 (dt, J=5.8, 3.0 Hz, 1H, ArH), 6.97 (br, 1H, NH), 4.93 (t, J=5.1 Hz, 1H, CH), 4.18 (m, 6H, ArOCH$_2$+OCH$_2$+OCH$_2$C(O)), 4.04 (m, 1H, 0.5×OCH$_2$), 3.87 (m, 1H, 0.5×OCH$_2$), 3.81 (m, 2H, OCH$_2$), 3.69 (m, 2H, CH$_2$N), 3.62 (m, 2H, CH$_2$N), 1.30 (t, J=7.1 Hz, 3H, CH$_3$).

Sodium (2-{2-[3-(2-aminoethylcarbamoyl)phenoxy]-1-azidoethoxy}ethoxy)acetate

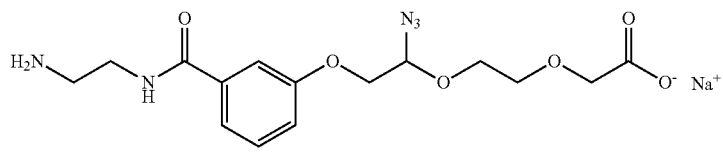 [SMILES: [N-]=[N+]=NC(COc1cccc(C(=O)NCCN)c1)OCCOCC(=O)[O-] ; [Na+]]

[2-(1-Azido-2-{3-[2-(2,2,2-trifluoroacetamido)ethylcarbamoyl]phenoxy}ethoxy)ethoxy]acetic acid ethyl ester (0.90 g, 1.83 mmol) was dissolved in ethanol (7 mL) and 4 M aqueous sodium hydroxide (7 mL) was added. The resulting mixture was stirred at room temperature for 2.5 h before being concentrated under reduced pressure. The material obtained was dissolved in water (55 mL) and washed with dichloromethane (2×50 mL). The aqueous layer was acidified to pH 2 using 1 M hydrochloric acid and washed with dichloromethane (2×50 mL). The organic layer was removed and discarded while the aqueous layer was neutralised to pH 8 using 1 M aqueous sodium hydroxide and evaporated under reduced pressure to give a white solid which was entrained with dichloromethane and methanol (2×95 mL, 1:1, v/v). The solid obtained was removed by suction filtration. The combined filtrates were concentrated under reduced pressure to give a gum. This impure gum was entrained with dichloromethane and methanol (10 mL, 9:1, v/v) and the insoluble white solid obtained was removed by suction filtration. The filtrate was concentrated under reduced pressure to give sodium (2-{2-[3-(2-aminoethylcarbamoyl)phenoxy]-1-azidoethoxy}ethoxy)acetate (0.76 g, quantitative), as a white foam.

$^1$H NMR (300 MHz, D$_2$O): δ 7.31 (m, 3H, 3×ArH), 7.11 (ddd, J=7.8, 2.6, 1.5 Hz, 1H, ArH), 4.99 (t, J=4.5 Hz, 1H, CH), 4.15 (m, 2H, ArOCH$_2$), 3.94 (m, 1H, 0.5×OCH$_2$), 3.79 (m, 3H, 0.5×OCH$_2$+OCH$_2$C(O)), 3.58 (m, 4H, OCH$_2$+CH$_2$N), 3.10 (t, J=5.8 Hz, 2H, CH$_2$N).

2-(2-{1-Azido-2-[3-({2-[3,5-bis(methoxycarbonyl)benzamido]ethyl}carbamoyl)phenoxy]ethoxy}ethoxy)acetic acid (Fragment 2)

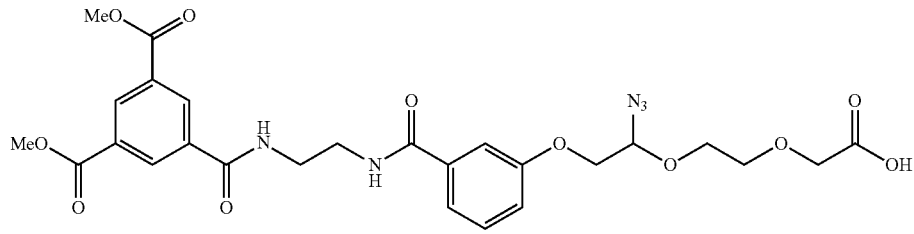 [SMILES: COC(=O)c1cc(C(=O)NCCNC(=O)c2cccc(OCC(N=[N+]=[N-])OCCOCC(=O)O)c2)cc(C(=O)OC)c1]

Trimethyl 1,3,5-benzenetricarboxylate (2.00 g, 7.93 mmol) was suspended in methanol (180 mL) and 1 M aqueous sodium hydroxide solution (7.14 mL) was added. The reaction mixture was stirred at room temperature for 18 h. The resulting solution was concentrated under reduced pressure to afford a white solid which was partitioned between dichloromethane (150 mL) and saturated aqueous sodium bicarbonate solution (150 mL). The organic phase was separated and was extracted with saturated aqueous sodium bicarbonate solution (150 mL) before being discarded. The combined aqueous layers were acidified to pH 1-2 using concentrated hydrochloric acid and were extracted with ethyl acetate (2×150 mL). The combined organic layers were dried (MgSO$_4$) and concentrated to give 3,5-bis(methoxycarbonyl)benzoic acid (1.66 g, 88%), as a white solid.

3,5-bis(Methoxycarbonyl)benzoic acid (0.80 g, 3.36 mmol) was dissolved in ethyl acetate (20 mL) and N-hydroxysuccinimide (425 mg, 3.69 mmol) was added followed by N,N'-dicyclohexylcarbodiimide (0.76 g, 3.69 mmol). The reaction mixture was stirred at room temperature for 20 h. The resulting suspension was filtered over Celite and the filtrate was washed with saturated aqueous sodium bicarbonate solution (2×100 mL), water (100 mL) and saturated brine (100 mL). The organic layer was dried (MgSO$_4$) and concentrated under reduced pressure to afford a white glassy solid. This material was purified using a Biotage Isolera automated chromatography system under normal phase conditions (silica column, gradient of 0→100% ethyl acetate in petrol) with detection at 254 nm to give N-hydroxysuccinimido 3,5-bis(methoxycarbonyl)benzoate (1.06 g, 95%), as a white solid.

R$_f$ 0.44 (petrol-ethyl acetate, 4:6, v/v).

To a solution of N-hydroxysuccinimido 3,5-bis(methoxycarbonyl)benzoate (0.95 g, 2.83 mmol) and sodium (2-{2-[3-(2-aminoethylcarbamoyl)phenoxy]-1-azidoethoxy}ethoxy)acetate (0.92 g, 2.36 mmol) in anhydrous DMF (15 mL) was added Hunig's base (0.61 g, 0.83 mL, 4.72 mmol) and the reaction mixture was stirred at room temperature overnight. The resulting mixture was diluted with ethyl acetate (20 mL) and quenched with 1 M hydrochloric acid (20 mL). The aqueous phase was separated, extracted with ethyl acetate (3×30 mL) and the combined organic phases were washed with water (5×50 mL) and saturated brine (50 mL). The resulting solution was dried (MgSO$_4$) before being concentrated under reduced pressure to give a white glassy solid. This material was purified using a Biotage Isolera automated chromatography system under normal phase conditions (silica column, gradient of 0→50% methanol in dichloromethane) with detection at 254 nm to give 2-(2-{1-azido-2-[3-({2-[3,5-bis(methoxycarbonyl)benzamido]ethyl}carbamoyl)phenoxy]ethoxy}ethoxy)acetic acid (Fragment 2) (0.92 g, 66%), as a white glassy solid.

R$_f$ 0.37 (dichloromethane-methanol, 83:17, v/v).

$^1$H NMR (300 MHz, d$_6$-DMSO) δ 9.42 (br, 1H, NH), 8.99 (br, 1H, NH), 8.66 (d, J=1.5 Hz, 2H, 2×ArH), 8.53 (t, J=1.5 Hz, 1H, ArH), 7.50 (m, 1H, ArH), 7.43 (d, J=7.7 Hz, 1H, ArH), 7.33 (t, J=7.9 Hz, 1H, ArH), 7.07 (dd, J=8.0, 2.4 Hz, 1H, ArH), 5.21 (t, J=5.0 Hz, 1H, CH), 4.24 (dd, J=10.6, 4.4 Hz, 1H, 0.5×ArOCH$_2$), 4.07 (dd, J=10.6, 5.9 Hz, 1H, 0.5×ArOCH$_2$), 3.88 (m, 8H, OCH$_2$+2×OCH$_3$), 3.84 (m, 1H, 0.5×OCH$_2$), 3.77 (m, 1H, 0.5×OCH$_2$), 3.62 (m, 2H, OCH$_2$C(O)), 3.40 (m, 4H, 2×CH$_2$N).

Pre-Cleavable SCCTP

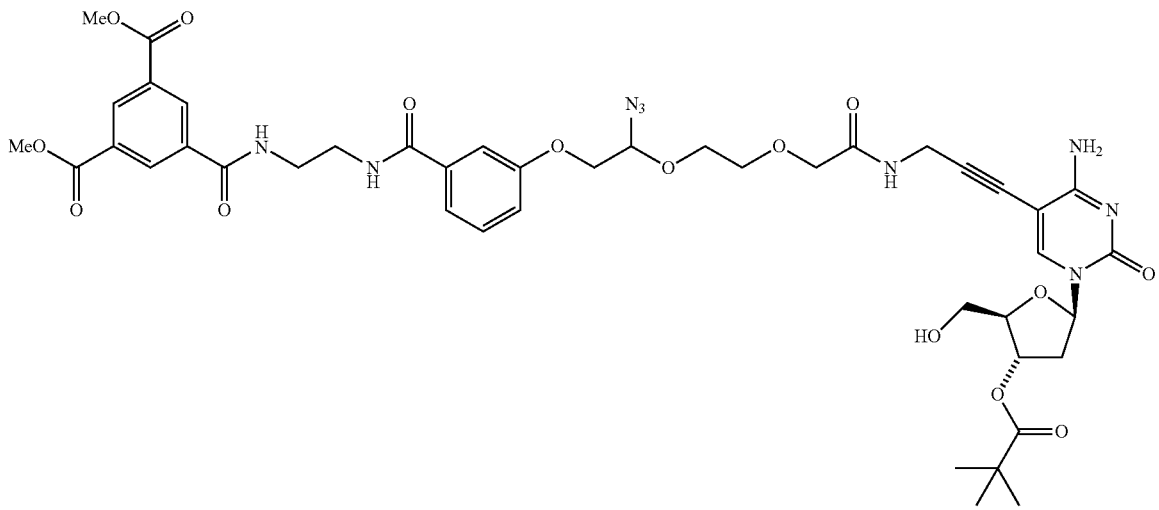 [SMILES: COC(=O)c1cc(C(=O)NCCNC(=O)c2cccc(OCC(N=[N+]=[N-])OCCOCC(=O)NCC#Cc3cn([C@H]4C[C@H](OC(=O)C(C)(C)C)[C@@H](CO)O4)c(=O)nc3N)c2)cc(C(=O)OC)c1]

3'-O-Pivaloyl-5-(3-aminopropynyl)-2'-deoxycytidine trifluoroacetate (379 mg, 0.79 mmol) was dissolved in anhydrous DMF (11.1 mL). Hunig's base (292 mg, 391 µL, 2.26 mmol) followed by 2-(2-{1-azido-2-[3-({2-[3,5-bis(methoxycarbonyl)benzamido]ethyl}carbamoyl)phenoxy]ethoxy}ethoxy)acetic acid (332 mg, 0.57 mmol) and HBTU (223 mg, 0.59 mmol) were added. The reaction mixture was stirred at room temperature overnight. The resulting mixture was diluted with ethyl acetate (50 mL) and washed with water (50 mL). The aqueous phase was separated and extracted with ethyl acetate (2×50 mL). The combined organic phases were washed with water (5×50 mL), saturated brine (50 mL), dried (MgSO$_4$) and concentrated under reduced pressure to give a pale yellow solid. This solid was purified using a Biotage Isolera automated chromatography system under normal phase conditions (silica column, gradient of 2→16% methanol in dichloromethane) with detection at 254 nm to give Pre-Cleavable SCCTP (410 mg, 77%), as a white solid.

R$_f$ 0.46 (dichloromethane-methanol, 92:8, v/v).

$^1$H NMR (300 MHz, DMSO-d$_6$): δ 9.09 (br t, J=5.8 Hz, 1H, NH), 8.68 (d, J=1.6 Hz, 2H, 2×ArH), 8.63 (br t, J=5.8 Hz, 1H, NH), 8.59 (t, J=1.6 Hz, 1H, ArH), 8.24 (t, J=5.4 Hz, 1H, NH), 8.11 (s, 1H, deoxycytidine CH), 7.86 (br, 1H, 0.5×NH$_2$), 7.46 (m, 2H, 2×ArH), 7.38 (t, J=7.8 Hz, 1H, ArH), 7.13 (m, 1H, ArH), 6.94 (br, 1H, 0.5×NH$_2$), 6.12 (dd, J=8.4, 5.8 Hz, 1H, CH), 5.24 (t, J=5.2 Hz, 1H, OH), 5.16 (m, 2H, CHOPiv+CHN), 4.23 (dd, J=10.4, 4.5 Hz, 1H, 0.5×ArOCH$_2$), 4.13 (m, 3H, 0.5×ArOCH$_2$+OCH$_2$), 3.88 (m, 10H, CH$_2$N+CH+0.5×OCH$_2$+2×OCH$_3$), 3.85 (m, 1H, 0.5×OCH$_2$), 3.68 (m, 2H, OCH$_2$C(O)), 3.62 (m, 2H, deoxycytidine CH$_2$), 3.47 (m, 4H, 2×CH$_2$N), 2.17 (m, 2H, deoxycytidine CH$_2$), 1.16 (s, 9H, 3×CH$_3$).

Penta-Triethylammonium Cleavable SCCTP

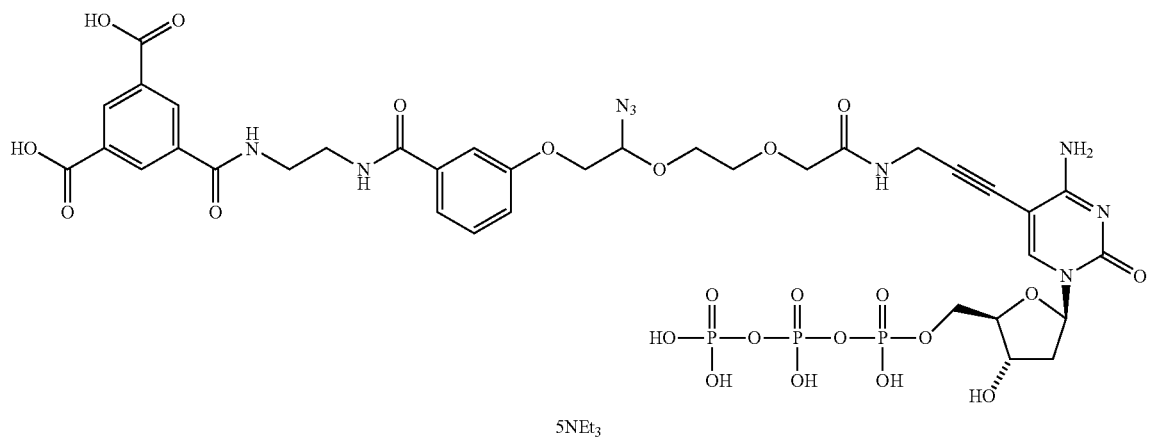 [SMILES: [N-]=[N+]=NC(COc1cccc(C(=O)NCCNC(=O)c2cc(C(=O)O)cc(C(=O)O)c2)c1)OCCOCC(=O)NCC#Cc1cn([C@H]2C[C@H](O)[C@@H](COP(=O)(O)OP(=O)(O)OP(=O)(O)O)O2)c(=O)nc1N]

5NEt$_3$

Pre-Cleavable SCCTP (155 mg, 0.17 mmol) was dissolved in 1,4-dioxane (510 µL) and anhydrous pyridine (430 µL) and the flask was evacuated and purged with a nitrogen atmosphere three times. 1.0 M Salicyl chlorophosphite solution in 1,4-dioxane (480 µL, 0.18 mmol) was added and the reaction mixture was stirred for 10 min. 0.5 M Tributylammonium pyrophosphate solution in anhydrous DMF (480 µL, 0.25 mmol) and tri-n-butylamine (129 mg, 165 µL, 0.70 mmol) were simultaneously added and the reaction mixture was stirred for 15 min. 1% Iodine solution in pyridine and water (3.4 mL, 92:8 v/v) was added and the solution was stirred for 30 min before being quenched with 5% aqueous sodium thiosulfate solution (100 μL) and concentrated under reduced pressure. The material obtained was purified using a Biotage Isolera automated chromatography system under reversed-phase conditions ($C_{18}$ column, gradient of 0→100% acetonitrile in 0.1 M TEAA at pH 8) with detection at 292 nm to afford, after freeze-drying, impure protected Cleavable SCCTP (147 mg, 59%) which was used without further purification.

1 M Aqueous sodium hydroxide solution (730 μL) was added to a solution of protected Cleavable SCCTP (94 mg) in water (800 μL) and stirred at room temperature for 40 min. The reaction mixture was quenched with 1 M aqueous triethylammonium bicarbonate (TEAB) solution (pH 8.5, 6 mL). The resulting solution was lyophilized overnight and the material was dissolved in water (1 mL) to give a concentration of 115 mg/mL. This solution was purified by semi-preparative HPLC injecting 60 μL portions and collecting the eluent containing the pure substance. The combined fractions were reduced in volume by removing the acetonitrile and most of the water and finally lyophilized to give penta-triethylammonium Cleavable SCCTP (45 mg, 17% over two steps), as a white solid.

HPLC Conditions:
Column: Phenomenex Luna C18(2), 15 mm×250 mm
Solvent Gradient: 90% 0.1 M aqueous TEAB to 85.6% 0.1 M aqueous TEAB over 22 min with the balance being acetonitrile.
Flow Rate: 7.8 mL/min
Temp: 30° C.
Detection: UV at 290 nm
Under these conditions the product had a retention time of ca. 19-21 min.

Example 6

Synthesis of Supercharged ATP (SCATP)

7-Deaza-7-iodo-2'-deoxyadenosine

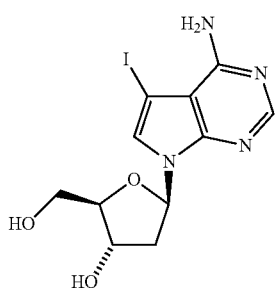 [SMILES: Nc1ncnc2c1c(I)cn2[C@H]1C[C@H](O)[C@@H](CO)O1]

6-Chloro-7-iodo-7-deazapurine (0.56 g, 2.00 mmol) was added to a fine slurry of potassium hydroxide (236 mg, 4.20 mmol) and tris(2-(2-methoxyethoxy)ethyl)amine (81 mg, 80 μL, 0.25 mmol) in anhydrous acetonitrile (25 mL) and the resulting mixture was stirred for 10 min. 3,5-di-O-(p-toluyl)-2-deoxy-D-ribofuranosyl chloride (0.97 g, 2.50 mmol) was added to the reaction mixture and the resulting yellow mixture was stirred for 25 min. The resulting mixture was filtered through Celite and the filter cake was washed with acetonitrile (10 mL) followed by dichloromethane (100 mL). The combined filtrates were concentrated under reduced pressure and the material obtained was purified using a Biotage Isolera automated chromatography system under normal phase conditions (silica column, gradient of 0→40% ethyl acetate in petrol) with detection at 254 nm to give 7-deaza-6-chloro-7-iodo-2'-deoxyadenosine (0.94 g, 75%) as a pale yellow solid.

7-Deaza-6-chloro-7-iodo-2'-deoxyadenosine (0.94 g, 1.49 mmol) was suspended in a 7 N solution of ammonia in methanol (19 mL) and heated under microwave irradiation at 120° C. for 10 h. The resulting solution was concentrated under reduced pressure and the residue obtained was purified using a Biotage Isolera automated chromatography system under normal phase conditions (silica column, gradient of 0→20% methanol in dichloromethane) with detection at 254 nm to give 7-deaza-7-iodo-2'-deoxyadenosine (476 mg, 85%), as a white solid.

$R_f$ 0.46 (dichloromethane-methanol, 9:1, v/v).

$^1$H NMR (300 MHz, DMSO-$d_6$): δ 8.10 (s, 1H, ArH), 7.66 (s, 1H, ArH), 6.68 (br s, 2H, $NH_2$), 6.48 (dd, J=8.3, 5.6 Hz, 1H, CH), 5.26 (d, J=4.6 Hz, 1H, OH), 5.05 (t, J=5.4 Hz, 1H, OH), 4.32 (m, 1H, CH), 3.81 (m, 1H, CH), 3.53 (m, 2H, $OCH_2$), 2.44 (m, 1H, 0.5×$CH_2$), 2.15 (m, 1H, 0.5×$CH_2$).

5'-O-Dimethoxytrityl-7-deaza-7-iodo-2'-deoxyadenosine

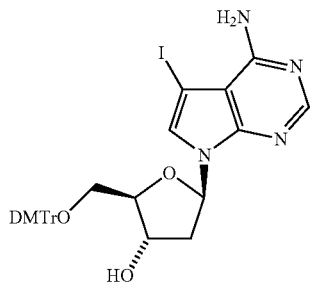

7-Deaza-7-iodo-2'-deoxyadenosine (475 mg, 1.26 mmol) was dissolved in anhydrous pyridine (6 mL) and stirred under nitrogen. After 5 min, 4-(dimethylamino)pyridine (8 mg, 0.07 mmol) and triethylamine (18 mg, 23 μL, 0.18 mmol) were added to the reaction mixture, followed by 4,4'-dimethoxytriphenylmethyl chloride (470 mg, 1.39 mmol). The resulting reaction mixture was stirred at room temperature overnight and was quenched with methanol (3 mL) before being concentrated under reduced pressure. The pyridine residues were azeotropically removed with methanol (3×10 mL) and dichloromethane (10 mL) to give a white solid. This crude material was purified using a Biotage Isolera automated chromatography system under normal phase conditions (silica column, gradient of 0→10% methanol in dichloromethane) with detection at 254 nm to give 5'-O-dimethoxytrityl-7-deaza-7-iodo-2'-deoxyadenosine (450 mg, 53%), as a white solid.

$R_f$ 0.36 (dichloromethane-methanol, 9:1, v/v).

$^1$H NMR (300 MHz, $CDCl_3$): δ 8.16 (s, 1H, ArH), 7.36 (m, 2H, 2×ArH), 7.25 (m, 8H, 8×ArH), 6.78 (m, 4H, 4×ArH), 6.61 (t, J=6.6 Hz, 1H, CH), 5.61 (s, 2H, $NH_2$), 4.54 (m, 1H, CH), 4.01 (m, 1H, CH), 3.73 (s, 6H, 2×$OCH_3$), 3.31 (m, 2H, $CH_2$), 2.42 (m, 2H, $CH_2$).

N-3'-Di-pivaloyl-5'-O-dimethoxytrityl-7-deaza-7-iodo-2'-deoxyadenosine

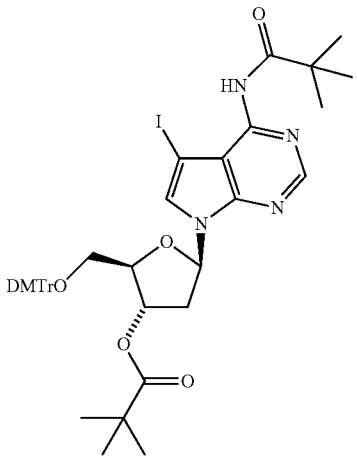

5'-O-Dimethoxytrityl-7-deaza-7-iodo-2'-deoxyadenosine (420 mg, 0.62 mmol) was dissolved in anhydrous acetonitrile (9 mL). 4-(Dimethylamino)pyridine (15 mg, 0.12 mmol), triethylamine (414 mg, 570 µL, 4.09 mmol) and trimethylacetic anhydride (0.76 g, 0.83 mL, 4.09 mmol) were added and the reaction mixture was stirred at 50° C. for 48 h. The resulting mixture was allowed to cool to room temperature and was concentrated under reduced pressure. The impure material was azeotropically dried with dichloromethane (3×10 mL) to give a pale-yellow, glassy solid which was purified using a Biotage Isolera automated chromatography system under normal phase conditions (silica column, gradient of 0→10% methanol in dichloromethane) with detection at 254 nm to give N-3'-O-dipivaloyl-5'-O-dimethoxytrityl-7-deaza-7-iodo-2'-deoxyadenosine (0.52 g, quantitative), as a white solid.

$R_f$ 0.60 (dichloromethane-methanol, 9:1, v/v).
$^1$H NMR (300 MHz, CDCl$_3$): δ 8.92 (s, 1H, NH), 8.74 (s, 1H, ArH), 7.62 (s, 1H, ArH), 7.43 (m, 2H, 2×ArH), 7.31 (m, 7H, 7×ArH), 6.86 (m, 4H, 4×ArH), 6.78 (m, 1H, CH), 5.54 (m, 1H, CH), 4.19 (m, 1H, CH), 3.81 (s, 6H, 2×OCH$_3$), 3.50 (m, 1H, 0.5×CH$_2$), 3.41 (m, 1H, 0.5×CH$_2$), 2.79 (m, 1H, 0.5×CH$_2$), 2.59 (m, 1H, 0.5×CH$_2$), 1.25 (s, 18H, 6×CH$_3$).

3'-O-Pivaloyl-5'-O-dimethoxytrityl-7-deaza-7-iodo-2'-deoxyadenosine

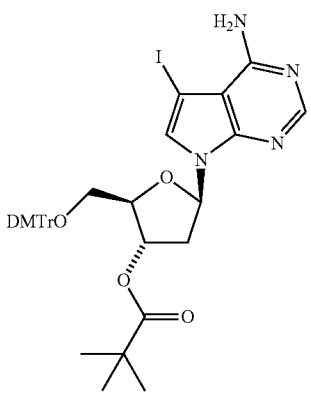

N-3'-O-Dipivaloyl-5'-O-dimethoxytrityl-7-deaza-7-iodo-2'-deoxyadenosine (0.52 g, 0.61 mmol) was dissolved in anhydrous methanol (10.5 mL) and Hunig's base (119 mg, 160 µL, 0.92 mmol) was added. The reaction mixture was heated under microwave irradiation at 110° C. for 6 h before being concentrated under reduced pressure. The impure material was purified using a Biotage Isolera automated chromatography system under normal phase conditions (silica column, gradient of 0→10% methanol in dichloromethane) with detection at 254 nm to give 3'-O-pivaloyl-5'-O-dimethoxytrityl-7-deaza-7-iodo-2'-deoxyadenosine (423 mg, 91%), as a pale yellow solid.

$R_f$ 0.44 (dichloromethane-methanol, 96:4, v/v).
$^1$H NMR (300 MHz, CDCl$_3$): δ 8.14 (s, 1H, ArH), 7.30 (m, 10H, 10×ArH), 6.76 (m, 4H, 4×ArH), 6.61 (m, 1H, CH), 6.29 (s, 2H, NH$_2$), 5.43 (m, 1H, CH), 4.09 (m, 1H, CH), 3.73 (s, 6H, 2×OCH$_3$), 3.37 (m, 2H, CH$_2$), 2.66 (m, 1H, 0.5×CH$_2$), 2.43 (m, 1H, 0.5×CH$_2$), 1.17 (s, 9H, 3×CH$_3$).

3'-O-Pivaloyl-5'-O-dimethoxytrityl-7-deaza-7-(3-Boc-aminoprop-1-yn-1-yl)-2'-deoxyadenosine

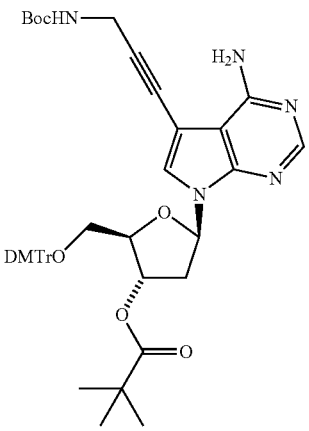

3'-O-Pivaloyl-5'-O-dimethoxytrityl-7-deaza-7-iodo-2'-deoxyadenosine (420 mg, 0.55 mmol), copper(I) iodide (23 mg, 0.12 mmol) and tetrakis(triphenylphosphine)palladium (0) (64 mg, 0.06 mmol) were dissolved in ethyl acetate (4.2 mL) and the flask was evacuated then purged with nitrogen four times. Hunig's base (142 mg, 187 µL, 1.10 mmol) and N-Boc-propargylamine (256 mg, 1.65 mmol) were added and the resulting mixture was evacuated and purged with nitrogen before being left to stir at room temperature overnight. The reaction mixture was diluted with ethyl acetate (25 mL) and washed with 5% aqueous EDTA solution (10 mL). The layers were separated and the aqueous phase was washed with ethyl acetate (10 mL). The combined organic layers were washed with saturated brine (10 mL), dried (MgSO$_4$) and concentrated under reduced pressure to give a dark yellow solid. This solid was purified using a Biotage Isolera automated chromatography system under normal phase conditions (silica column, gradient of 0→13% methanol in dichloromethane) with detection at 254 nm to give 3'-O-pivaloyl-5'-O-dimethoxytrityl-7-deaza-7-(3-Boc-aminoprop-1-yn-1-yl)-2'-deoxyadeno sine (0.51 g), as a yellow solid.

$R_f$ 0.51 (dichloromethane-methanol, 9:1, v/v).
$^1$H NMR (300 MHz, CDCl$_3$): δ 8.18 (s, 1H, ArH), 7.26 (m, 10H, 10×ArH), 6.76 (m, 4H, 4×ArH), 6.58 (m, 1H, CH), 5.94 (s, 2H, NH$_2$), 5.37 (m, 1H, CH), 4.94 (m, 1H, CH), 4.10 (m, 1H, NH), 4.01 (d, J=5.7 Hz, 2H, CH$_2$), 3.73 (s, 6H, 2×OCH$_3$), 3.32 (m, 2H, CH$_2$), 2.62 (m, 1H, 0.5×CH$_2$), 2.40 (m, 1H, 0.5×CH$_2$), 1.39 (s, 9H, 3×CH$_3$), 1.17 (s, 9H, 3×CH$_3$).

3'-O-Pivaloyl-7-deaza-7-(3-aminoprop-1-yn-1-yl)-2'-deoxyadenosine Di-trifluoroacetate

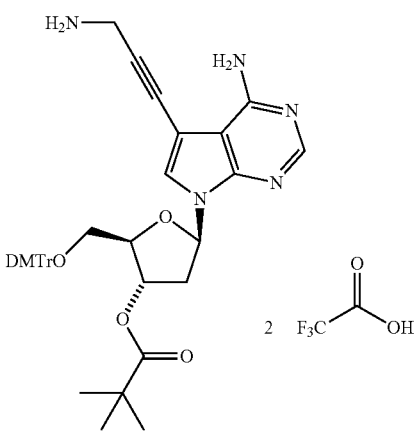

3'-O-Pivaloyl-5'-O-dimethoxytrityl-7-deaza-7-(3-Boc-aminoprop-1-yn-1-yl)-2'-deoxyadenosine (0.51 g, 0.55 mmol) was dissolved in anhydrous dichloromethane (12 mL) and trifluoroacetic acid (1.70 mL) was added dropwise. The mixture was then stirred for 2 h at room temperature and was subsequently diluted with dichloromethane (25 mL). The resulting solution was concentrated under reduced pressure and the residual trifluoroacetic acid was azeotropically removed with dichloromethane (4×25 mL). The crude material obtained was purified using a Biotage Isolera automated chromatography system under reversed-phase conditions (C$_{18}$ column, gradient of 0→40% acetonitrile in 0.1% aqueous trifluoroacetic acid) with detection at 254 nm to afford, after freeze-drying, the required 3'-O-Pivaloyl-7-deaza-7-(3-aminoprop-1-yn-1-yl)-2'-deoxyadenosine di-trifluoroacetate (Fragment 1) (257 mg, 76% over two-steps), as an off-white solid.

$^1$H NMR (300 MHz, DMSO-d$_6$): δ 8.29 (m, 7H, ArH+ 2×NH$_3^+$), 7.98 (m, 1H, ArH), 6.50 (m, 1H, CH), 5.32 (m, 1H, CH), 4.03 (m, 3H, CH+CH$_2$), 3.62 (m, 2H, CH$_2$), 2.72 (m, 1H, 0.5×CH$_2$), 2.40 (m, 1H, 0.5×CH$_2$), 1.19 (s, 9H, 3×CH$_3$).

3-[(1,3)Dioxolan-2-ylmethoxy]benzoic acid ethyl ester

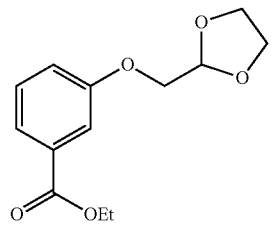 [SMILES: CCOC(=O)c1cccc(OCC2OCCO2)c1]

Ethyl 3-hydroxybenzoate (3.50 g, 21.1 mmol), bromoethyl-1,3-dioxolane (14.1 g, 8.72 mL, 84.3 mmol), potassium carbonate (5.83 g, 42.1 mmol) and sodium iodide (1.26 g, 8.43 mmol) were dissolved in anhydrous DMF (10 mL) and the reaction mixture was stirred at 120° C. for 20 h. The suspension was cooled to room temperature and quenched with water (30 mL). The aqueous phase was extracted with ethyl acetate (3×50 mL). The organic layers were combined, washed with water (5×100 mL) and saturated brine (100 mL), before being dried (MgSO$_4$) and concentrated under reduced pressure to afford an orange oil. This oil was purified using a Biotage Isolera automated chromatography system under normal phase conditions (silica column, gradient of 0→30% ethyl acetate in petrol) with detection at 254 nm to give 3-[(1,3)dioxolan-2-ylmethoxy]benzoic acid ethyl ester (5.09 g, 96%), as a colorless oil.

R$_f$ 0.40 (petrol-ethyl acetate, 75:25, v/v).

$^1$H NMR (400 MHz, CDCl$_3$): δ 7.66 (dt, J=7.5, 1.1 Hz, 1H, ArH), 7.59 (dd, J=2.6, 1.5 Hz, 1H, ArH), 7.34 (t, J=7.9 Hz, 1H, ArH), 7.14 (ddd, J=8.3, 2.6, 1.0 Hz, 1H, ArH), 5.31 (t, J=4.1 Hz, 1H, CH), 4.36 (q, J=7.2 Hz, 2H, OCH$_2$), 4.02 (m, 6H, OCH$_2$CH$_2$O+ArOCH$_2$), 1.39 (t, J=7.1 Hz, 3H, CH$_3$).

3-[2-Azido-2-(2-hydroxyethoxy)ethoxy]benzoic acid ethyl ester

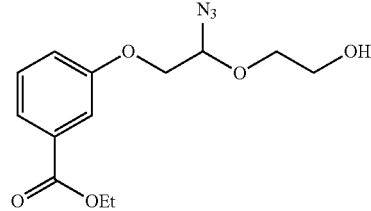

To a mixture of 3-[(1,3)dioxolan-2-ylmethoxy]benzoic acid ethyl ester (5.08 g, 20.1 mmol) and azidotrimethylsilane (2.55 g, 2.94 mL, 22.2 mmol) was added tin(IV) chloride (336 mg, 151 µL, 1.29 mmol). The reaction mixture was stirred at room temperature for 2 h. The resulting mixture was diluted with 2% aqueous methanol (60 mL) and stirred for 30 min before being concentrated under reduced pressure. The residue was azeotropically dried with ethanol (2×30 mL) to afford a colorless oil. This oil was purified using a Biotage Isolera automated chromatography system under normal phase conditions (silica column, gradient of 0→70% ethyl acetate in petrol) with detection at 254 nm to give 3-[2-azido-2-(2-hydroxyethoxy)ethoxy]benzoic acid ethyl ester (3.59 g, 59%), as a colorless oil.

R$_f$ 0.41 (petrol-ethyl acetate, 53:47, v/v).

$^1$H NMR (300 MHz, CDCl$_3$): δ 7.69 (dt, J=7.7, 1.2 Hz, 1H, ArH), 7.59 (dd, J=2.6, 1.5 Hz, 1H, ArH), 7.36 (t, J=8.0 Hz, 1H, ArH), 7.13 (ddd, J=8.3, 2.7, 1.0 Hz, 1H, ArH), 4.89 (t, J=5.1 Hz, 1H, CH), 4.38 (q, J=7.1 Hz, 2H, OCH$_2$), 4.19 (m, 2H, ArOCH$_2$), 4.00 (m, 1H, 0.5×OCH$_2$), 3.80 (m, 3H, 0.5×OCH$_2$+OCH$_2$), 1.40 (t, J=7.1 Hz, 3H, CH$_3$).

3-[2-Azido-2-(2-hydroxyethoxy)ethoxy]benzoic acid

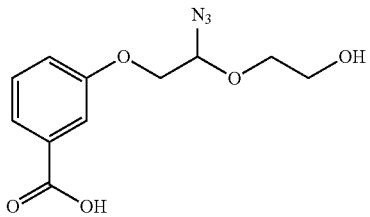

3-[2-Azido-2-(2-hydroxyethoxy)ethoxy]benzoic acid ethyl ester (3.51 g, 11.9 mmol) was dissolved in ethanol (30 mL) and 4 M aqueous sodium hydroxide (30 mL) was added. The mixture was stirred at room temperature for 3.5 h and the volume was then reduced by ¾ under vacuum. The resulting mixture was diluted with water (50 mL) and acidified to pH 1-2 with 2 M hydrochloric acid. This mixture was extracted with dichloromethane (3×100 mL). The combined organic phases were washed with saturated brine (150 mL), dried (MgSO$_4$) and concentrated under reduced pressure to afford 3-[2-azido-2-(2-hydroxyethoxy)ethoxy]benzoic acid (3.39 g, quantitative), as a colorless oil which was used without further purification.

$^1$H NMR (300 MHz, CDCl$_3$): δ 7.76 (dt, J=7.7, 1.2 Hz, 1H, ArH), 7.65 (dd, J=2.4, 1.4 Hz, 1H, ArH), 7.41 (t, J=8.0 Hz, 1H, ArH), 7.19 (ddd, J=8.2, 2.7, 1.0 Hz, 1H, ArH), 4.90 (t, J=5.1 Hz, 1H, CH), 4.21 (m, 2H, ArOCH$_2$), 4.03 (m, 1H, 0.5×OCH$_2$), 3.81 (m, 3H, 0.5×OCH$_2$+OCH$_2$).

3-[2-Azido-2-(2-ethoxycarbonylmethoxyethoxy)ethoxy]benzoic acid

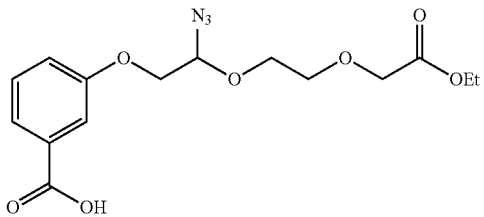 [SMILES: CCOC(=O)COCCOC(COc1cccc(C(=O)O)c1)N=[N+]=[N-]]

To an ice-cold solution of 3-[2-azido-2-(2-hydroxyethoxy)ethoxy]benzoic acid (1.42 g, 5.31 mmol) in anhydrous THF (18 mL) was added sodium hydride (0.64 g, 15.9 mmol) and the mixture was stirred at 0° C. for 10 min. Ethyl bromoacetate (1.95 g, 1.30 mL, 11.7 mmol) was added and the reaction mixture was allowed to warm up to room temperature over 5 h. The resulting mixture was quenched with ice-water (20 mL) and washed with dichloromethane (2×70 mL). The aqueous layer was acidified to pH 1-2 using 2 M hydrochloric acid and was extracted with dichloromethane (3×70 mL). The combined organic layers were dried (MgSO$_4$) and concentrated under reduced pressure to afford a colorless oil. This material was purified using a Biotage Isolera automated chromatography system under normal phase conditions (silica column, gradient of 0→60% ethyl acetate in dichloromethane) with detection at 254 nm to give 3-[2-azido-2-(2-ethoxycarbonylmethoxyethoxy)ethoxy]benzoic acid (0.62 g, 33%), as a colorless oil.

R$_f$ 0.45 (ethyl acetate-dichloromethane, 4:6 v/v).
$^1$H NMR (300 MHz, CDCl$_3$): δ 7.75 (dt, J=7.7, 1.2 Hz, 1H, ArH), 7.64 (dd, J=2.7, 1.5 Hz, 1H, ArH), 7.40 (t, J=8.0 Hz, 1H, ArH), 7.19 (ddd, J=8.3, 2.7, 1.0 Hz, 1H, ArH), 4.95 (dd, J=5.5, 4.6 Hz, 1H, CH), 4.14 (m, 7H, ArOCH$_2$+0.5× OCH$_2$+OCH$_2$+OCH$_2$C(O)), 3.86 (m, 3H, 0.5×OCH$_2$+ OCH$_2$), 1.28 (t, J=7.2 Hz, 3H, CH$_3$).

N-(2-Aminoethyl)-2,2,2-trifluoroacetamide Trifluoroacetate

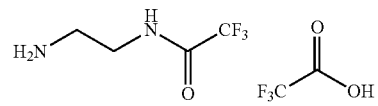

To an ice-cold solution of N-Boc-ethylenediamine (2.08 g, 2.05 mL, 13.0 mmol) in anhydrous THF (8 mL) was slowly added ethyl trifluoroacetate (1.85 g, 1.55 mL, 13.0 mmol) and the reaction mixture was stirred at room temperature overnight. The resulting solution was concentrated under reduced pressure to give tert-butyl [2-(2,2,2-trifluoroacetamido)ethyl]carbamate (3.30 g, 99%), as a white solid which was used without further purification.

tert-Butyl [2-(2,2,2-trifluoroacetamido)ethyl]carbamate (1.04 g, 4.06 mmol) was dissolved in trifluoroacetic acid (5 mL) and stirred at room temperature for 30 min. The resulting mixture was concentrated under reduced pressure and the residual trifluoroacetic acid was azeotropically removed with chloroform (3×10 mL). The material obtained was dried in vacuo at 50° C. for 2 h to give N-(2-aminoethyl)-2,2,2-trifluoroacetamide trifluoroacetate (1.07 g, 99%), as a yellow oil which was used without further purification.

$^1$H NMR (300 MHz, DMSO-d$_6$): δ 9.58 (br t, 1H, NH), 7.99 (br s, 3H, NH$_3^+$), 3.43 (m, 2H, CH$_2$N), 2.97 (m, 2H, CH$_2$N).

[2-(1-Azido-2-{3-[2-(2,2,2-trifluoroacetamido)ethylcarbamoyl]phenoxy}ethoxy)ethoxy]acetic acid ethyl ester

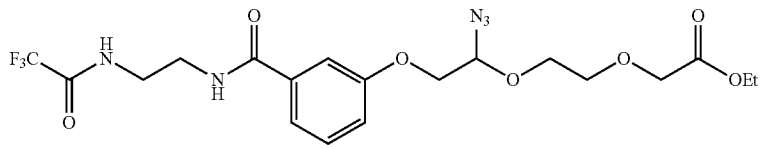 [SMILES: CCOC(=O)COCCOC(COc1cccc(C(=O)NCCNC(=O)C(F)(F)F)c1)N=[N+]=[N-]]

To a solution of N-(2-aminoethyl)-2,2,2-trifluoroacetamide trifluoroacetate (1.31 g, 4.86 mmol) in anhydrous DMF (25 mL) was added Hunig's base (1.57 g, 2.12 mL, 12.1 mmol), 3-[2-azido-2-(2-ethoxycarbonylmethoxyethoxy)ethoxy]benzoic acid (1.43 g, 4.05 mmol) and PyBOP (2.32 g, 4.45 mmol). The reaction mixture was stirred at room temperature for 20 h before being diluted with ethyl acetate (20 mL) and quenched with 1 M hydrochloric acid (40 mL). The aqueous phase was extracted with ethyl acetate (3×50 mL). The combined organic layers were washed with water (5×100 mL), saturated brine (100 mL), dried (MgSO$_4$) and concentrated under reduced pressure to give a yellow oil. This oil was purified using a Biotage Isolera automated chromatography system under normal phase conditions (silica column, gradient of 0→90% ethyl acetate in dichloromethane) with detection at 254 nm to give [2-(1-azido-2-{3-[2-(2,2,2-trifluoroacetamido)ethylcarbamoyl]phenoxy}ethoxy)ethoxy]acetic acid ethyl ester (1.75 g, 88%) as a colorless oil.

R$_f$ 0.48 (dichloromethane-ethyl acetate, 1:1, v/v).

$^1$H NMR (300 MHz, CDCl$_3$): δ 8.01 (br, 1H, NH), 7.39 (m, 3H, 3×ArH), 7.10 (dt, J=5.8, 3.0 Hz, 1H, ArH), 6.97 (br, 1H, NH), 4.93 (t, J=5.1 Hz, 1H, CH), 4.18 (m, 6H, ArOCH$_2$+OCH$_2$+OCH$_2$C(O)), 4.04 (m, 1H, 0.5×OCH$_2$), 3.87 (m, 1H, 0.5×OCH$_2$), 3.81 (m, 2H, OCH$_2$), 3.69 (m, 2H, CH$_2$N), 3.62 (m, 2H, CH$_2$N), 1.30 (t, J=7.1 Hz, 3H, CH$_3$).

<p style="text-align: center;">Sodium (2-{2-[3-(2-aminoethylcarbamoyl)phenoxy]-1-azidoethoxy}ethoxy)acetate</p>

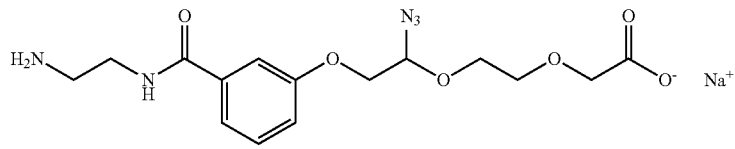 [SMILES: [N-]=[N+]=NC(COc1cccc(C(=O)NCCN)c1)OCCOCC(=O)[O-] ; [Na+]]

[2-(1-Azido-2-{3-[2-(2,2,2-trifluoroacetamido)ethylcarbamoyl]phenoxy}ethoxy)ethoxy]acetic acid ethyl ester (0.90 g, 1.83 mmol) was dissolved in ethanol (7 mL) and 4 M aqueous sodium hydroxide (7 mL) was added. The resulting mixture was stirred at room temperature for 2.5 h before being concentrated under reduced pressure. The material obtained was dissolved in water (55 mL) and washed with dichloromethane (2×48 mL). The aqueous layer was acidified to pH 2 using 1 M hydrochloric acid and washed with dichloromethane (2×50 mL). The organic layer was removed and discarded while the aqueous layer was neutralised to pH 8 using 1 M aqueous sodium hydroxide and evaporated under reduced pressure to give a white solid which was entrained with dichloromethane and methanol (2×95 mL, 1:1, v/v). The solid obtained was removed by suction filtration. The combined filtrates were concentrated under reduced pressure to give a gum. This crude gum was entrained with dichloromethane and methanol (10 mL, 9:1, v/v) and the insoluble white solid obtained was removed by suction filtration. The filtrate was concentrated under reduced pressure to give sodium (2-{2-[3-(2-amino ethylcarbamoyl)phenoxy]-1-azidoethoxy}ethoxy)acetate (0.76 g, quantitative), as a white foam.

$^1$H NMR (300 MHz, D$_2$O): δ 7.31 (m, 3H, 3×ArH), 7.11 (ddd, J=7.8, 2.6, 1.5 Hz, 1H, ArH), 4.99 (t, J=4.5 Hz, 1H, CH), 4.15 (m, 2H, ArOCH$_2$), 3.94 (m, 1H, 0.5×OCH$_2$), 3.79 (m, 3H, 0.5×OCH$_2$+OCH$_2$C(O)), 3.58 (m, 4H, OCH$_2$+CH$_2$N), 3.10 (t, J=5.8 Hz, 2H, CH$_2$N).

<p style="text-align: center;">N-Hydrosuccinimido 3,5-bis{[(S)-1,5-dimethoxy-1,5-dioxopentan-2-yl]carbamoyl}benzoate</p>

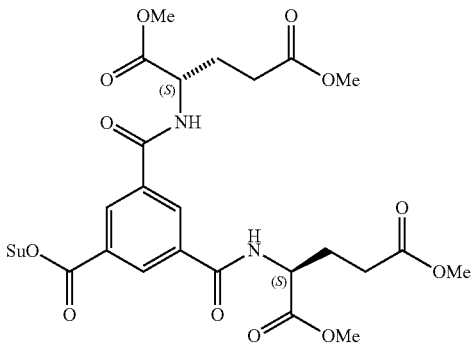

Trimethyl 1,3,5-benzenetricarboxylate (4.00 g, 15.9 mmol) was suspended in methanol (360 mL) and 1 M aqueous sodium hysroxide (14.3 mL, 14.3 mmol) was added. The mixture was vigorously stirred at room temperature for 18 h. The resulting solution was concentrated under reduced pressure to afford a white solid which was partitioned between dichloromethane (300 mL) and saturated aqueous sodium bicarbonate solution (300 mL). The organic phase was separated and was extracted with saturated aqueous sodium bicarbonate solution (300 mL) before being discarded. The combined aqueous extracts were acidified to pH 1-2 using concentrated hydrochloric acid and were extracted with ethyl acetate (2×300 mL). The combined organic layers were dried (MgSO$_4$) and concentrated to give 3,5-bis(methoxycarbonyl)benzoic acid (3.10 g, 82%), as a white solid.

To an ice-cold suspension of 3,5-bis(methoxycarbonyl)benzoic acid (1.35 g, 5.67 mmol) in anhydrous pyridine (15 mL) was added tosyl chloride (1.84 g, 9.63 mmol) and tert-butanol (0.50 g, 0.64 mL, 6.80 mmol) and the reaction mixture was stirred at room temperature for 20 h. The resulting suspension was diluted with ethyl acetate (75 mL) and a 20% aqueous solution of citric acid (75 mL). The aqueous layer was extracted with diethyl ether (3×100 mL) and the combined organic layers were washed with a 20% aqueous solution of citric acid (100 mL), 1 M hydrochloric acid (100 mL), water (3×100 mL) and saturated brine (100 mL), before being dried (MgSO$_4$) and concentrated to give a pale yellow solid. This material was purified using a Biotage Isolera automated chromatography system under normal phase conditions (silica column, gradient of 0→50% ethyl acetate in petrol) with detection at 254 nm to give 1-(tert-butyl) 3,5-dimethyl benzene-1,3,5-tricarboxylate (1.10 g, 66%), as a white solid.

R$_f$ 0.32 (ethyl acetate-petrol, 3:7, v/v).

1-(tert-Butyl) 3,5-dimethyl benzene-1,3,5-tricarboxylate (0.50 g, 1.70 mmol) was suspended in anhydrous THF (25 mL) and 0.1 M aqueous sodium hydroxide (15 mL) was added. The resulting suspension was stirred at room temperature for 2 h. The pH of the reaction mixture was adjusted to 11 by addition of 1 M aqueous sodium hydroxide and the resulting mixture was stirred for 1 h. The reaction mixture was neutralised with 1 M hydrochloric acid before being concentrated to ⅓ of the volume. This resulting mixture was diluted with water (15 mL) and the pH was adjusted to 2 with addition of 2 M hydrochloric acid. The precipitate formed was collected by suction filtration and azeotropically dried with acetonitrile (3×10 mL) to give an off-white solid. This reaction sequence was repeated due to the presence of mono-methyl ester left in the resulting solid to afford 5-(tert-butoxycarbonyl)isophthalic acid (428 mg, 95%), as a white solid.

To a solution of H-Glu(OMe)-OMe hydrochloride (1.27 g, 5.99 mmol) and Hunig's base (1.03 g, 1.39 mL, 7.98 mmol) in anhydrous DMF (7 mL) was added a solution of 5-(tert-butoxycarbonyl)isophthalic acid (0.53 g, 2.00 mmol) in anhydrous DMF (8 mL), followed by PyBOP (2.29 g, 4.39 mmol) and the reaction mixture was stirred at room temperature for 20 h. The resulting mixture was diluted with ethyl acetate (40 mL) and quenched with 1 M aqueous sodium hydroxide (50 mL). The aqueous layer was separated and was then extracted with ethyl acetate (3×25 mL). The combined organic layers were washed with water (70 mL), saturated aqueous sodium bicarbonate solution (70 mL), water (5×70 mL) and saturated brine (70 mL) before being dried (MgSO$_4$) and concentrated under reduced pressure to give a white solid. This solid was purified using a Biotage Isolera automated chromatography system under normal phase conditions (silica column, gradient of 0→70% ethyl acetate in dichloromethane) with detection at 254 nm to give tetramethyl 2,2'-{[5-(tert-butoxycarbonyl)isophthaloyl]bis(azanediyl)}(2S,2'S)-diglutarate (0.69 g, 60%), as a white solid.

$R_f$ 0.44 (dichloromethane-ethyl acetate, 6:4, v/v).

Tetramethyl 2,2'-{[5-(tert-butoxycarbonyl)isophthaloyl]bis(azanediyl)}(2S,2'S)-diglutarate (0.67 g, 1.15 mmol) was stirred in trifluoroacetic acid (9 mL) for 1 h. The solution was concentrated under reduced pressure and the residual trifluoroacetic acid was azeotropically removed with chloroform (5×10 mL) and diethyl ether (3×10 mL) to give 5-bis{[(S)-1,5-dimethoxy-1,5-dioxopentan-2-yl]carbamoyl}benzoic acid (0.61 g, 99%), as a white foam.

This reaction was repeated to yield further batches of material.

5-bis{[(S)-1,5-Dimethoxy-1,5-dioxopentan-2-yl]carbamoyl}benzoic acid (0.64 g, 1.23 mmol) was dissolved in ethyl acetate (20 mL) and N-hydroxysuccinimide (156 mg, 1.35 mmol) was added followed by N,N'-dicyclohexylcarbodiimide (279 mg, 1.35 mmol). The resulting mixture was stirred at room temperature for 20 h. The suspension was filtered through Celite and the filtrate was washed with saturated aqueous sodium bicarbonate solution (2×30 mL), water (2×30 mL) and saturated brine (30 mL). The organic layer was dried (MgSO$_4$) and concentrated under reduced pressure to afford a white foam. This material was purified using a Biotage Isolera automated chromatography system under normal phase conditions (silica column, gradient of 0→100% ethyl acetate in petrol) with detection at 254 nm to give N-hydrosuccinimido 3,5-bis{[(S)-1,5-dimethoxy-1,5-dioxopentan-2-yl]carbamoyl}benzoate (0.63 g, 79%), as a white solid.

$R_f$ 0.44 (petrol-ethyl acetate, 4:6, v/v).

$^1$H NMR (300 MHz, DMSO-d$_6$): δ 9.32 (d, J=7.5 Hz, 2H, 2×NH), 8.77 (m, 1H, ArH), 8.71 (m, 2H, 2×ArH), 4.53 (m, 2H, 2× α-CH), 3.67 (s, 6H, 2×OCH$_3$), 3.59 (s, 6H, 2×OCH$_3$), 2.94 (s, 4H, 2×CH$_2$-su), 2.46 (m, 4H, 2×CH$_2$), 2.07 (m, 4H, 2×CH$_2$).

2-{2-[1-azido-2-(3-{[2-(3,5-bis{[(S)-1,5-dimethoxy-1,5-dioxopentan-2-yl]carbamoyl}benzamido)ethyl]carbamoyl}phenoxy)ethoxy]ethoxy}acetic acid

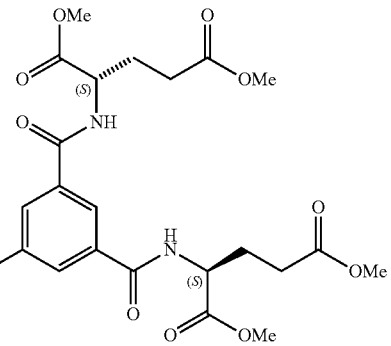

To a solution of N-hydroxysuccinimido 3,5-bis(methoxycarbonyl)benzoate (0.78 g, 1.25 mmol) and sodium (2-{2-[3-(2-aminoethylcarbamoyl)phenoxy]-1-azidoethoxy}ethoxy)acetate (445 mg, 1.14 mmol) in anhydrous DMF (7 mL) was added Hunig's base (295 mg, 400 µL, 2.28 mmol) and the reaction mixture was stirred at room temperature for 20 h. The resulting mixture was diluted with ethyl acetate (10 mL) and quenched with 1 M hydrochloric acid (20 mL). The aqueous phase was separated and extracted with ethyl acetate (3×30 mL) and the combined organic phases were washed with water (5×50 mL) and saturated brine (50 mL). The resulting solution was dried (MgSO$_4$) before being concentrated under reduced pressure to give a white foam. This crude material was purified using a Biotage Isolera automated chromatography system under normal phase conditions (silica column, gradient of 0→50% methanol in dichloromethane) with detection at 254 nm to give 2-{2-[1-azido-2-(3-{[2-(3,5-bis{[(S)-1,5-dimethoxy-1,5-dioxopentan-2-yl]carbamoyl}benzamido)ethyl]carbamoyl}phenoxy)ethoxy]ethoxy}acetic acid (Fragment 2) (0.83 g, 83%), as a white solid.

$R_f$ 0.43 (dichloromethane-methanol, 83:17, v/v).

$^1$H NMR (300 MHz, DMSO-d$_6$): δ 9.26 (br s, 1H, NH), 9.17 (d, J=7.3 Hz, 2H, 2×NH), 8.95 (br s, 1H, NH), 8.55 (m, 2H, 2×ArH), 8.47 (m, 1H, ArH), 7.55 (m, 1H, ArH), 7.49 (m, 1H, ArH), 7.37 (t, J=7.9 Hz, 1H, ArH), 7.11 (dd, J=7.9, 1.5 Hz, 1H, ArH), 5.20 (t, J=5.0 Hz, 1H, CH), 4.49 (m, 2H, 2× α-CH), 4.25 (dd, J=10.7, 4.5 Hz, 1H, 0.5×CH$_2$), 4.14 (dd, J=10.7, 5.3 Hz, 1H, 0.5×CH$_2$), 3.89 (m, 2H, CH$_2$), 3.80 (m, 2H, CH$_2$), 3.65 (s, 8H, 2×OCH$_3$+CH$_2$), 3.59 (s, 6H, 2×OCH$_3$), 3.49 (br, 4H, 2×CH$_2$), 2.47 (m, 4H, 2×CH$_2$), 2.07 (m, 4H, 2×CH$_2$).

Pre-Cleavable SCATP

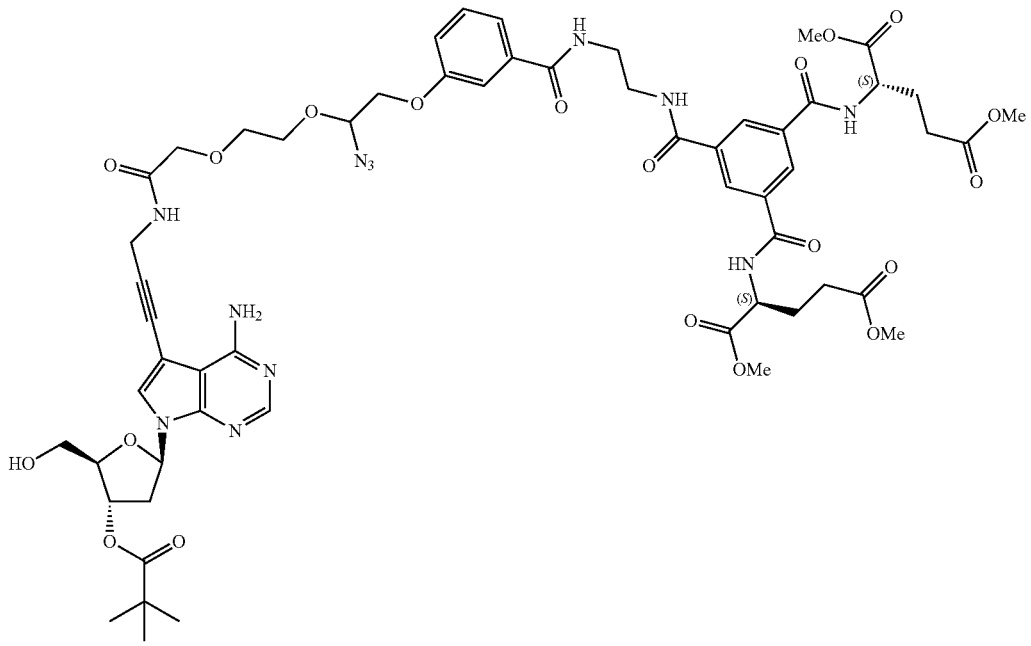

3'-O-Pivaloyl-5-(3-aminopropynyl)-2'-deoxyuridine di-trifluoroacetate (366 mg, 0.60 mmol) was dissolved in anhydrous DMF (12 mL). Hunig's base (295 mg, 390 µL, 2.28 mmol) followed by 2-(2-{1-azido-2-[3-({2-[3,5-bis (methoxycarbonyl)benzamido]ethyl}carbamoyl)phenoxy] ethoxy}ethoxy)acetic acid (399 mg, 0.46 mmol) and HBTU (182 mg, 0.48 mmol) were added. The reaction mixture was stirred at room temperature for 20 h. The resulting mixture was diluted with ethyl acetate (20 mL) and washed with water (20 mL). The aqueous phase was separated and extracted with ethyl acetate (2×20 mL). The combined organic phases were washed with water (5×40 mL) and saturated brine (40 mL), before being dried (MgSO$_4$) and concentrated under reduced pressure to give an orange solid. This solid was purified using a Biotage Isolera automated chromatography system under normal phase conditions (silica column, gradient of 0→30% methanol in ethyl acetate) with detection at 254 nm to afford Pre-Cleavable SCATP (307 mg, 54%), as an off-white solid.

R$_f$ 0.41 (ethyl acetate-methanol, 9:1, v/v).

$^1$H NMR (300 MHz, DMSO-d$_6$): δ 9.10 (d, J=7.3 Hz, 2H, 2×NH), 8.92 (br s, 1H, NH), 8.65 (br s, 1H, NH), 8.48 (s, 2H, 2×ArH), 8.37 (t, J=5.4 Hz, 1H, ArH), 8.10 (s, 1H, ArH), 7.75 (s, 1H, ArH), 7.46 (m, 2H, 2×ArH), 7.36 (t, J=7.8 Hz, 1H, ArH), 7.13 (dd, J=7.7, 2.1 Hz, 1H, ArH), 6.45 (dd, J=9.0, 5.5 Hz, 1H, CH), 5.31 (m, 2H, OH+CH), 5.15 (t, J=4.5 Hz, 1H, CHN$_3$), 4.51 (m, 2H, 2× α-CH), 4.22 (dd, J=10.5, 4.6 Hz, 1H, 0.5×CH$_2$), 4.14 (m, 3H, 0.5×CH$_2$+CH$_2$), 3.97 (m, 5H, CH+2×CH$_2$), 3.86 (m, 2H, CH$_2$), 3.67 (br, 8H, 2×OCH$_3$+CH$_2$), 3.59 (s, 6H, 2×OCH$_3$), 3.46 (br, 4H, 2×NCH$_2$), 2.72 (m, 1H, 0.5×CH$_2$), 2.47 (m, 4H, 2×CH$_2$), 2.35 (m, 1H, 0.5×CH$_2$), 2.07 (m, 4H, 2×CH$_2$), 1.19 (s, 9H, 3×CH$_3$).

Hepta-Triethylammonium Cleavable SCATP

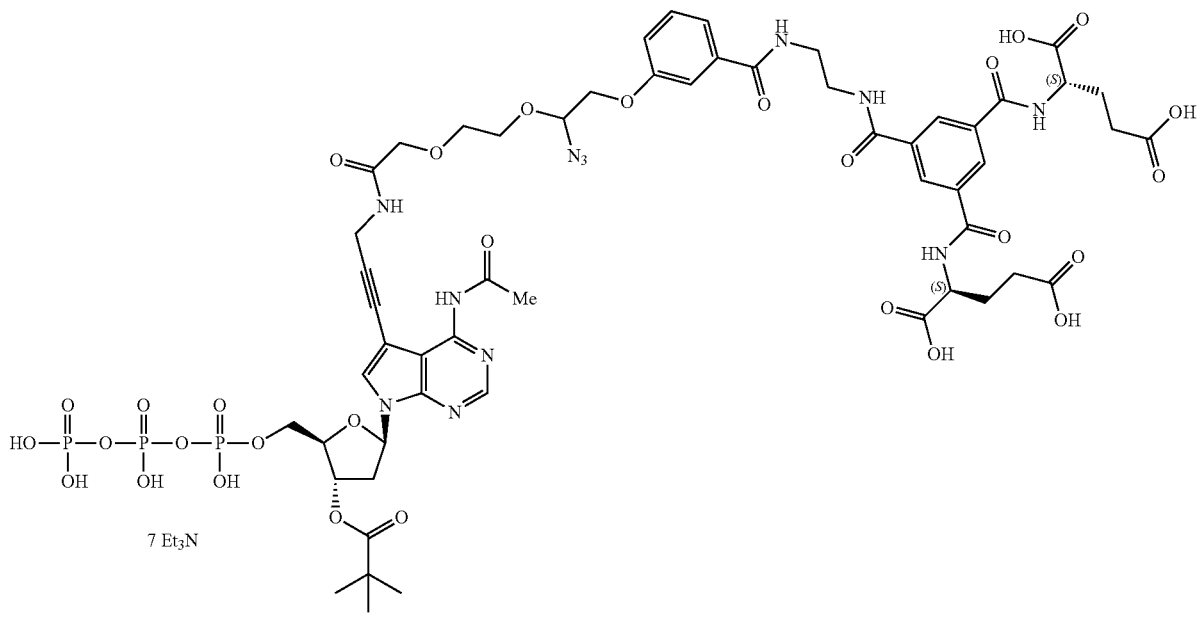

Pre-Cleavable SCATP (300 mg, 0.24 mmol) was dissolved in 1,4-dioxane (0.73 mL) and anhydrous pyridine (245 µL) and the flask was evacuated and purged with a nitrogen atmosphere five times. 1.0 M Salicyl chlorophosphite solution in 1,4-dioxane (270 µL, 0.27 mmol) was added and the reaction mixture was stirred for 10 min. 0.5 M Tributylammonium pyrophosphate solution in anhydrous DMF (0.73 mL, 0.36 mmol) and tributylamine (187 mg, 240 µL, 1.01 mmol) were added and the reaction mixture was stirred for 20 min. 1% Iodine solution in pyridine and water (4.9 mL, 98:2 v/v) were added and the solution was stirred for 15 min before being quenched with 5% aqueous sodium thiosulfate solution (0.60 mL) and concentrated under reduced pressure. The material obtained was purified using a Biotage Isolera automated chromatography system under reversed-phase conditions ($C_{18}$ column, gradient of 0→40% acetonitrile in 0.1 M TEAA at pH 8) with detection at 279 nm to afford, after freeze-drying, impure protected Cleavable SCATP (178 mg, 42%) which was used without further purification.

Protected Cleavable SCATP (175 mg) was dissolved in water (1.23 mL) and the resulting solution was stirred for 15 min before addition of 1 M aqueous sodium hydroxide (1.47 mL). The mixture was stirred at room temperature for 40 min and was diluted with 1 M aqueous triethylammonium bicarbonate (TEAB) solution (pH 8, 3 mL). The resulting solution was lyophilized overnight (250 mg) and the material was dissolved in water (3.6 mL) to give a concentration of 69.4 mg/mL. This solution was purified by semi-preparative HPLC injecting 100 µL portions and collecting the eluent containing the pure substance. The combined fractions were reduced in volume by removing the acetonitrile and most of the water and finally lyophilized to give hepta-triethylammonium Cleavable SCATP (150 mg, 75%), as a white solid.

HPLC Conditions:
Column: Phenomenex Luna C18(2), 15 mm×250 mm
Solvent Gradient: 90% 0.1 M aqueous TEAB (pH 7.0) to 85.5% 0.1 M aqueous TEAB (pH 7.0) over 30 min with the balance being acetonitrile.
Flow Rate: 7.8 mL/min
Temp: 30° C.
Detection: UV at 277 nm
Under these conditions the product had a retention time of ca. 23-30 min.

Example 7

Synthesis of Supercharged GTP (SCGTP)

6-O-Methyl-7-deaza-2'-deoxyguanosine

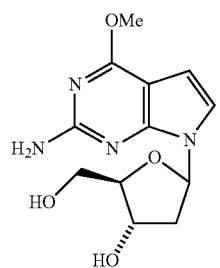 [SMILES: COc1nc(N)nc2c1ccn2C1C[C@H](O)[C@@H](CO)O1]

A fine slurry of powdered potassium hydroxide (1.14 g, 20.4 mmol) and tris-(2-(2-methoxyethoxy)ethyl)amine (TDA-1) (96 mg, 95 µL, 0.30 mmol) was stirred in anhydrous acetonitrile (40 mL) for 15 min at room temperature. 2-Amino-4-chloro-7H-pyrrolo[2,3-d]pyrimidine (1.00 g, 5.93 mmol) was added and the reaction mixture was stirred for 10 min. 3,5-Di-O-(p-tolyl)-2-deoxy-D-ribofuranosyl chloride (2.39 g, 5.99 mmol) was added and the reaction mixture was stirred for 30 min. The resulting mixture was filtered through Celite, the filter cake was washed with acetonitrile (10 mL) and the filtrate concentrated to give a brown solid. This material was purified using a Biotage Isolera automated chromatography system under normal phase conditions (silica column, gradient of 0→11% ethyl acetate in dichloromethane) with detection at 254 nm to give 4-chloro-7-((4S,5R)-4-(p-tolyloxy)-5-((p-tolyloxy)methyl)tetrahydrofuran-2-yl)-7H-pyrrolo[2,3-d]pyrimidin-2-amine (1.98 g, 64%), as an off-white foam.

$R_f$ 0.37 (dichloromethane-ethyl acetate, 96:4, v/v).

To a suspension of 4-chloro-7-((4S,5R)-4-(p-tolyloxy)-5-((p-tolyloxy)methyl)tetrahydrofuran-2-yl)-7H-pyrrolo[2,3-d]pyrimidin-2-amine (1.98 g, 3.80 mmol) in anhydrous methanol (35 mL) was added a 0.5 M sodium methoxide solution in methanol (84 mL, 41.8 mmol) and the mixture was heated at 65° C. for 2 h. The resulting solution was cooled to room temperature and concentrated under reduced pressure to give an off-white solid. This residual material was purified using a Biotage Isolera automated chromatography system under normal phase conditions (silica column, gradient of 0→25% methanol in dichloromethane) with detection at 254 nm to give 6-O-methyl-7-deaza-2'-deoxyguanosine (0.89 g, 84%), as a white foam.

$R_f$ 0.50 (dichloromethane-methanol, 90:10, v/v).

$^1$H NMR (300 MHz, DMSO-$d_6$) δ 7.10 (d, J=3.7 Hz, 1H, CH), 6.40 (m, 1H, CHN), 6.27 (d, J=3.7 Hz, 1H, CH), 6.22 (br s, 2H, NH$_2$), 5.22 (d, J=3.8 Hz, 1H, OH), 4.94 (t, J=5.6 Hz, 1H, OH), 4.28 (m, 1H, CH), 3.91 (s, 3H, CH$_3$), 3.77 (m, 1H, CH), 3.50 (m, 2H, CH$_2$), 2.39 (m, 1H, 0.5×CH$_2$), 2.09 (m, 1H, 0.5×CH$_2$).

6-O-Methyl-2,3',5'-tripivaloyl-7-deaza-2'-deoxyguanosine

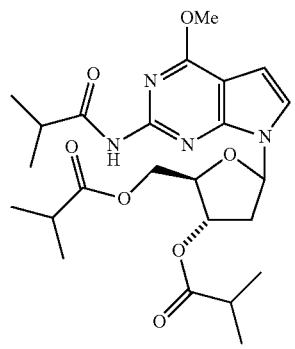 [SMILES: COc1nc(NC(=O)C(C)C)nc2c1ccn2C1C[C@H](OC(=O)C(C)C)[C@@H](COC(=O)C(C)C)O1]

To an ice-cold solution of 6-O-methyl-7-deaza-2'-deoxyguanosine (0.89 g, 3.18 mmol) in anhydrous pyridine (33 mL) was added isobutyryl chloride (3.05 g, 3.00 mL, 28.6 mmol) dropwise and the mixture was stirred for 1 h at this temperature. Methanol (2 mL) was added and the mixture was stirred for 15 min at 0° C. The suspension was concentrated and the residue was partitioned between saturated aqueous sodium bicarbonate solution (50 mL) and ethyl acetate (50 mL). The layers were separated and the aqueous layer was extracted with ethyl acetate (2×50 mL). The combined organic layers were washed with saturated aqueous sodium bicarbonate solution (50 mL), saturated brine (50 mL), dried (MgSO$_4$) and concentrated to give a yellow oil. This crude material was purified using a Biotage Isolera automated chromatography system under normal phase conditions (silica column, gradient of 0→58% ethyl acetate in petrol) with detection at 254 nm to give 6-O-methyl-2,3',5'-tripivaloyl-7-deaza-2'-deoxyguanosine (1.46 g, 94%), as a colorless oil.

$R_f$ 0.47 (petrol-ethyl acetate, 34:66, v/v).

$^1$H NMR (300 MHz, Methanol-$d_4$) δ 7.31 (d, J=3.7 Hz, 1H, CH), 6.68 (dd, J=8.7, 5.8 Hz, 1H, CHN), 6.54 (d, J=3.7 Hz, 1H, CH), 5.43 (m, 1H, CH), 4.38 (m, 2H, CH$_2$), 4.26 (m, 1H, CH), 4.01 (s, 3H, CH$_3$), 2.90 (m, 2H, 2×CH), 2.65 (m, 2H, CH+0.5×CH$_2$), 2.53 (m, 1H, 0.5×CH$_2$), 1.24 (m, 12H, 4×CH$_3$), 1.17 (m, 6H, 2×CH$_3$).

6-O-Methyl-2,3',5'-tripivaloyl-7-deaza-7-iodo-2'-deoxyguanosine

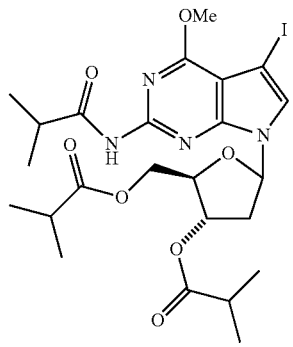 [SMILES: COc1nc(NC(=O)C(C)C)nc2c1c(I)cn2C1C[C@H](OC(=O)C(C)C)[C@@H](COC(=O)C(C)C)O1]

To a solution of 6-O-methyl-2,3',5'-tripivaloyl-7-deaza-2'-deoxyguanosine (1.13 g, 2.31 mmol) in anhydrous DMF (18 mL) was added N-iodosuccinimide (0.55 g, 2.42 mmol) and the mixture was stirred for 3 h at room temperature. The resulting red solution was concentrated to give a residual red oil that was partitioned between diethyl ether (20 mL) and saturated aqueous sodium bicarbonate solution (20 mL). The layers were separated and the aqueous layer was extracted with diethyl ether (2×25 mL). The combined organic layers were washed with water (4×50 mL), saturated brine (50 mL), dried (MgSO$_4$) and concentrated to give a brown solid. This material was purified using a Biotage Isolera automated chromatography system under normal phase conditions (silica column, gradient of 7→49% ethyl acetate in petrol) with detection at 254 nm to give 6-O-methyl-2,3',5'-tripivaloyl-7-deaza-7-iodo-2'-deoxyguanosine (1.08 g, 76%), as an off-white solid.

$R_f$ 0.37 (petrol-ethyl acetate, 72:28, v/v).

$^1$H NMR (300 MHz, Methanol-$d_4$) δ 7.46 (s, 1H, CH), 6.65 (m, 1H, CHN), 5.43 (m, 1H, CH), 4.37 (m, 2H, CH$_2$), 4.26 (m, 1H, CH), 4.11 (s, 3H, CH$_3$), 2.85 (m, 2H, CH+0.5×CH$_2$), 2.62 (m, 3H, 2×CH+0.5×CH$_2$), 1.21 (m, 18H, 6×CH$_3$).

7-Deaza-7-iodo-2'-deoxyguanosine

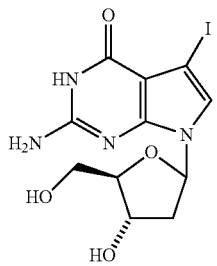 [SMILES: Nc1nc2c(c(I)cn2C2C[C@H](O)[C@@H](CO)O2)c(=O)[nH]1]

A suspension of 6-O-methyl-2,3',5'-tripivaloyl-7-deaza-7-iodo-2'-deoxyguanosine (1.40 g, 2.27 mmol) in 2 M aqueous sodium hydroxide (65 mL) and 1,4-dioxane (9 mL) was heated at 95° C. overnight. The mixture was allowed to cool to room temperature and the 1,4-dioxane was removed under vacuum. The aqueous solution was neutralised with 2 M hydrochloric acid to pH=7 and concentrated to dryness to give a white solid. This residual solid was suspended in water (100 mL), the solid was collected by suction filtration, washed with acetonitrile (20 mL) and dried in vacuo at 40° C. for 2 h to give 7-deaza-7-iodo-2'-deoxyguanosine (0.90 g), as a white solid that was used without further purification.

$^1$H NMR (300 MHz, DMSO-$d_6$) δ 10.52 (s, 1H, NH), 7.12 (s, 1H, CH), 6.35 (br s, 2H, NH$_2$), 6.26 (dd, J=8.5, 5.7 Hz, 1H, CHN), 5.21 (d, J=3.7 Hz, 1H, OH), 4.92 (t, J=5.4 Hz, 1H, OH), 4.27 (m, 1H, CH), 3.75 (m, 1H, CH), 3.49 (m, 2H, CH$_2$), 2.32 (m, 1H, 0.5×CH$_2$), 2.05 (m, 1H, 0.5×CH$_2$).

5'-O-(tert-Butyldimethylsilyl)-7-deaza-7-iodo-2'-deoxyguanosine

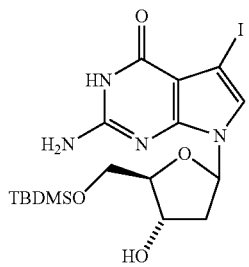 [SMILES: CC(C)(C)[Si](C)(C)OC[C@H]1OC(n2cc(I)c3c(=O)[nH]c(N)nc32)C[C@@H]1O]

To a solution of 7-deaza-7-iodo-2'-deoxyguanosine (0.90 g, 2.29 mmol) in anhydrous DMF (12 mL) was added imidazole (375 mg, 5.51 mmol) followed by tert-butyldimethylsilyl chloride (398 mg, 2.64 mmol) and the mixture was stirred for 20 h at room temperature. The resulting yellow solution was concentrated under reduced pressure to give an orange oil. This crude material was purified using a Biotage Isolera automated chromatography system under normal phase conditions (silica column, gradient of 7→36% methanol in dichloromethane) with detection at 254 nm to give 5'-O-(tert-butyldimethylsilyl)-7-deaza-7-iodo-2'-deoxyguanosine (0.81 g, 70% over two steps), as an off-white solid.

$R_f$ 0.43 (dichloromethane-methanol, 88:12, v/v).

$^1$H NMR (300 MHz, DMSO-$d_6$) δ 10.48 (s, 1H, NH), 7.05 (s, 1H, CH), 6.35 (br s, 2H, NH$_2$), 6.27 (dd, J=8.2, 5.8 Hz, 1H, CHN), 5.25 (d, J=3.7 Hz, 1H, OH), 4.26 (m, 1H, CH), 3.79 (m, 1H, CH), 3.70 (m, 2H, CH$_2$), 2.25 (m, 1H, 0.5×CH$_2$), 2.10 (m, 1H, 0.5×CH$_2$), 0.89 (s, 9H, TBDMS tert-butyl), 0.08 (s, 3H, TBDMS CH$_3$), 0.07 (s, 3H, TBDMS CH$_3$).

3'-O-Pivaloyl-5'-O-(tert-butyldimethylsilyl)-7-deaza-7-iodo-2'-deoxyguanosine

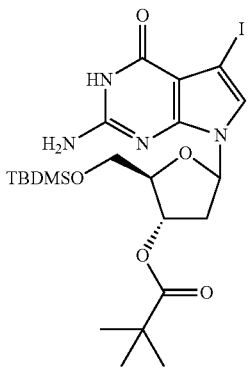 [SMILES: CC(C)(C)C(=O)O[C@H]1CC(n2cc(I)c3c(=O)[nH]c(N)nc32)O[C@@H]1CO[Si](C)(C)C(C)(C)C]

To a solution of 5'-O-(tert-butyldimethylsilyl)-7-deaza-7-iodo-2'-deoxyguanosine (0.80 g, 1.58 mmol) in anhydrous pyridine (20 mL) was added 4-dimethylamino-pyridine (DMAP) (39 mg, 0.32 mmol) followed by trimethylacetic anhydride (442 mg, 481 µL, 2.37 mmol) and the mixture was heated at 85° C. overnight. A further equivalent of trimethylacetic anhydride (295 mg, 321 µL, 1.58 mmol) and dimethylaminopyridine (DMAP) (39 mg, 0.32 mmol) was added and the reaction mixture was heated at 85° C. for 2 days. The resulting solution was cooled to room temperature and concentrated to dryness. The residue was partitioned between ethyl acetate (25 mL) and saturated aqueous sodium bicarbonate solution (25 mL). The layers were separated and the aqueous layer was extracted with ethyl acetate (2×20 mL). The combined organic layers were washed with saturated brine (40 mL), dried (MgSO$_4$) and concentrated to give a brown foam which was purified using a Biotage Isolera automated chromatography system under normal phase conditions (silica column, gradient of 0→100% ethyl acetate in dichloromethane and then 0→50% methanol in ethyl acetate) with detection at 254 nm to give 3'-O-pivaloyl-5'-O-(tert-butyldimethylsilyl)-7-deaza-7-iodo-2'-deoxyguanosine (0.63 g, 68%), as a brown foam.

$R_f$ 0.41 (dichloromethane-ethyl acetate, 40:60, v/v).

$^1$H NMR (300 MHz, DMSO-$d_6$) δ 10.53 (s, 1H, NH), 7.09 (s, 1H, CH), 6.39 (br s, 2H, NH$_2$), 6.26 (dd, J=9.0, 5.7 Hz, 1H, CHN), 5.14 (m, 1H, CH), 3.95 (m, 1H, CH), 3.76 (m, 2H, CH$_2$), 2.5 (obscured m, 1H, 0.5×CH$_2$), 2.29 (m, 1H, 0.5×CH$_2$), 1.17 (s, 9H, tert-butyl), 0.90 (s, 9H, TBDMS tert-butyl), 0.10 (s, 3H, TBDMS CH$_3$), 0.08 (s, 3H, TBDMS CH$_3$).

3'-O-Pivaloyl-7-deaza-7-iodo-2'-deoxyguanosine

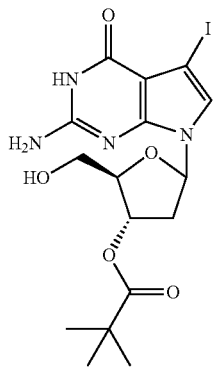 [SMILES: CC(C)(C)C(=O)O[C@H]1CC(n2cc(I)c3c(=O)[nH]c(N)nc32)O[C@@H]1CO]

To an ice-cold solution of 3'-O-pivaloyl-5'-O-(tert-butyldimethylsilyl)-7-deaza-7-iodo-2'-deoxyguanosine (100 mg, 0.17 mmol) in anhydrous THF (3 mL) was added 1 M TBAF in THF (0.25 mL, 0.25 mmol) dropwise and the mixture was stirred at room temperature for 1 h. The resulting solution was diluted with ethyl acetate (10 mL) and the reaction mixture was quenched with water (10 mL). The layers were separated and the aqueous layer was extracted with ethyl acetate (2×10 mL) and chloroform (5 mL). The combined organic were dried (MgSO$_4$) and concentrated to give a yellow solid. This material was purified using a Biotage Isolera automated chromatography system under normal phase conditions (silica column, gradient of 0→80% methanol in ethyl acetate) with detection at 254 nm to give 3'-O-pivaloyl-7-deaza-7-iodo-2'-deoxyguanosine (77 mg, 95%), as a white solid.

$R_f$ 0.60 (ethyl acetate-methanol, 9:1, v/v).
$^1$H NMR (300 MHz, DMSO-d$_6$) δ 10.51 (s, 1H, NH), 7.20 (s, 1H, CH), 6.36 (br s, 2H, NH$_2$), 6.24 (m, 1H, CHN), 5.28 (m, 1H, CH) 5.11 (t, J=5.4 Hz, 1H, OH) 3.95 (m, 1H, CH), 3.76 (m, 2H, CH$_2$), 2.60 (obscured m, 1H, 0.5×CH$_2$), 2.23 (m, 1H, 0.5×CH$_2$), 1.18 (s, 9H, tert-butyl).

3'-O-Pivaloyl-7-deaza-7-(3-Boc-aminoprop-1-yn-1-yl)-2'-deoxyguanosine

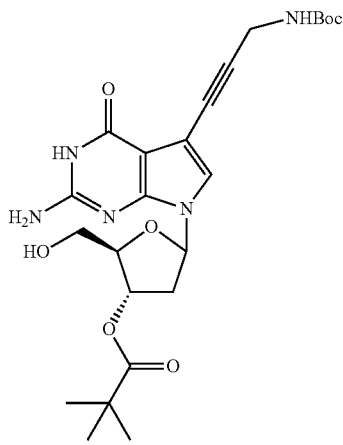 [SMILES: CC(C)(C)OC(=O)NCC#Cc1cn(C2C[C@H](OC(=O)C(C)(C)C)[C@@H](CO)O2)c2nc(N)[nH]c(=O)c12]

A solution of 3'-O-pivaloyl-7-deaza-7-iodo-2'-deoxyguanosine (75 mg, 0.16 mmol), tetrakis(triphenylphosphine)palladium (18 mg, 0.02 mmol) and copper iodide (6 mg, 0.03 mmol) in anhydrous DMF (5 mL) was deoxygenated for 10 min. N-Boc-propargylamine (73 mg, 0.47 mmol) and Hunig's base (41 mg, 55 µL, 0.31 mmol) were added, the solution was deoxygenated for a further 10 min and the reaction mixture was stirred overnight in the dark at room temperature. The resulting mixture was diluted with ethyl acetate (10 mL) and washed with 5% aqueous EDTA solution (10 mL). The layers were separated and the aqueous phase was extracted with ethyl acetate (2×15 mL). The combined organic layers were washed with water (2×15 mL), saturated brine (20 mL), dried (MgSO$_4$) and concentrated to give a brown foam. This material was purified using a Biotage Isolera automated chromatography system under normal phase conditions (silica column, gradient of 5→80% methanol in dichloromethane) with detection at 254 nm to give 3'-O-pivaloyl-7-deaza-7-(3-Boc-aminoprop-1-yn-1-yl)-2'-deoxyguanosine (57 mg, 72%), as an brown solid.

$R_f$ 0.37 (dichloromethane-methanol, 93:7, v/v).
$^1$H NMR (300 MHz, DMSO-d$_6$) δ 10.56 (s, 1H, NH), 7.31 (m, 2H, CH+NH), 6.36 (br s, 2H, NH$_2$), 6.25 (dd, J=9.5, 5.9 Hz, 1H, CHN), 5.25 (m, 1H, CH), 5.13 (t, 1H, J=5.6 Hz, OH), 3.90 (m, 2H, CH$_2$), 3.55 (m, 2H, CH$_2$), 2.5 (obscured m, 1H, 0.5×CH$_2$), 2.25 (m, 1H, 0.5×CH$_2$), 1.39 (s, 9H, Boc tert-butyl), 1.17 (s, 9H, tert-butyl).

3'-O-Pivaloyl-7-deaza-7-(3-aminoprop-1-yn-1-yl)-2'-deoxyguanosine trifluoroacetate

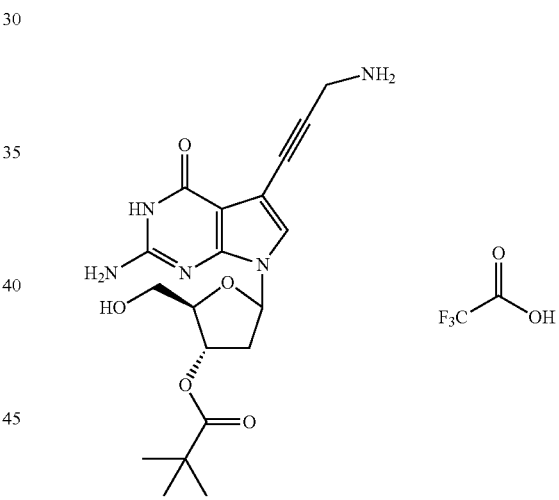

3'-O-Pivaloyl-7-deaza-7-(3-Boc-aminoprop-1-yn-1-yl)-2'-deoxyguanosine (85 mg, 0.17 mmol) was dissolved in anhydrous dichloromethane (1.25 mL) and trifluoroacetic acid (260 µL, 3.38 mmol) was added dropwise. The mixture was stirred for 2 h at room temperature and was concentrated under reduced pressure. The residual trifluoroacetic acid was azeotropically removed with chloroform (2×10 mL) and diethyl ether (2×10 mL). The impure material was purified using a Biotage Isolera automated chromatography system under reversed-phase conditions (C$_{18}$ column, gradient of 0→36% acetonitrile in 0.1% aqueous trifluoroacetic acid) with detection at 254 nm to afford, after freeze-drying, 3'-O-pivaloyl-7-deaza-7-(3-aminoprop-1-yn-1-yl)-2'-deoxyguanosine trifluoroacetate (Fragment 1) (60 mg, 69%), as an off-white solid.

$^1$H NMR (300 MHz, DMSO-d$_6$) δ 10.64 (s, 1H, NH), 8.25 (br s, 3H, NH$_3^+$), 7.39 (s, 1H, CH), 6.43 (br s, 2H, NH$_2$), 6.27 (dd, J=9.1, 5.8 Hz, 1H, CHN), 5.27 (m, 1H, CH), 3.96

(m, 3H, CH+CH$_2$), 3.58 (m, 2H, CH$_2$), 2.62 (m, 1H, 0.5×CH$_2$), 2.25 (m, 1H, 0.5×CH$_2$), 1.18 (s, 9H, tert-butyl).

3-[(1,3)Dioxolan-2-ylmethoxy]benzoic acid ethyl ester

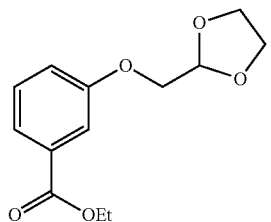 [SMILES: CCOC(=O)c1cccc(OCC2OCCO2)c1]

Ethyl 3-hydroxybenzoate (3.50 g, 21.1 mmol), bromoethyl-1,3-dioxolane (14.1 g, 8.72 mL, 84.3 mmol), potassium carbonate (5.83 g, 42.1 mmol) and sodium iodide (1.26 g, 8.43 mmol) were dissolved in anhydrous DMF (10 mL) and the reaction mixture was stirred at 120° C. for 20 h. The suspension was cooled to room temperature and quenched with water (30 mL). The aqueous phase was extracted with ethyl acetate (3×50 mL). The organic layers were combined, washed with water (5×100 mL) and saturated brine (100 mL), before being dried (MgSO$_4$) and concentrated under reduced pressure to afford an orange oil. This residual material was purified using a Biotage Isolera automated chromatography system under normal phase conditions (silica column, gradient of 0→30% ethyl acetate in petrol) with detection at 254 nm to give 3-[(1,3)dioxolan-2-ylmethoxy]benzoic acid ethyl ester (5.09 g, 96%), as a colorless oil.

R$_f$ 0.40 (petrol-ethyl acetate, 75:25, v/v).

$^1$H NMR (400 MHz, CDCl$_3$): δ 7.66 (dt, J=7.5, 1.1 Hz, 1H, ArH), 7.59 (dd, J=2.6, 1.5 Hz, 1H, ArH), 7.34 (t, J=7.9 Hz, 1H, ArH), 7.14 (ddd, J=8.3, 2.6, 1.0 Hz, 1H, ArH), 5.31 (t, J=4.1 Hz, 1H, CH), 4.36 (q, J=7.2 Hz, 2H, OCH$_2$), 4.02 (m, 6H, OCH$_2$CH$_2$O+ArOCH$_2$), 1.39 (t, J=7.1 Hz, 3H, CH$_3$).

3-[2-Azido-2-(2-hydroxyethoxy)ethoxy]benzoic acid ethyl ester

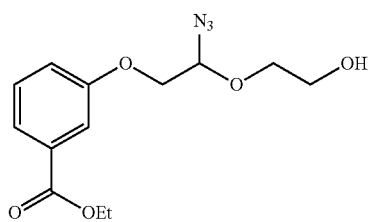

To a mixture of 3-[(1,3)dioxolan-2-ylmethoxy]benzoic acid ethyl ester (5.08 g, 20.1 mmol) and azidotrimethylsilane (2.55 g, 2.94 mL, 22.2 mmol) was added tin(IV) chloride (336 mg, 151 µL, 1.29 mmol). The reaction mixture was stirred at room temperature for 2 h. The resulting mixture was diluted with 2% aqueous methanol (60 mL) and stirred for 30 min before being concentrated under reduced pressure. The residue was azeotropically dried with ethanol (2×30 mL) to afford a colorless oil. This oil was purified using a Biotage Isolera automated chromatography system under normal phase conditions (silica column, gradient of 0→70% ethyl acetate in petrol) with detection at 254 nm to give 3-[2-azido-2-(2-hydroxyethoxy)ethoxy]benzoic acid ethyl ester (3.59 g, 59%), as a colorless oil.

R$_f$ 0.41 (petrol-ethyl acetate, 53:47, v/v).

$^1$H NMR (300 MHz, CDCl$_3$): δ 7.69 (dt, J=7.7, 1.2 Hz, 1H, ArH), 7.59 (dd, J=2.6, 1.5 Hz, 1H, ArH), 7.36 (t, J=8.0 Hz, 1H, ArH), 7.13 (ddd, J=8.3, 2.7, 1.0 Hz, 1H, ArH), 4.89 (t, J=5.1 Hz, 1H, CH), 4.38 (q, J=7.1 Hz, 2H, OCH$_2$), 4.19 (m, 2H, ArOCH$_2$), 4.00 (m, 1H, 0.5×OCH$_2$), 3.80 (m, 3H, 0.5×OCH$_2$+OCH$_2$), 1.40 (t, J=7.1 Hz, 3H, CH$_3$).

3-[2-Azido-2-(2-hydroxyethoxy)ethoxy]benzoic acid

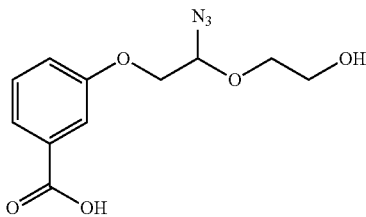 [SMILES: [N-]=[N+]=NC(COc1cccc(C(=O)O)c1)OCCO]

3-[2-Azido-2-(2-hydroxyethoxy)ethoxy]benzoic acid ethyl ester (3.51 g, 11.9 mmol) was dissolved in ethanol (30 mL) and 4 M aqueous sodium hydroxide (30 mL) was added. The mixture was stirred at room temperature for 3.5 h and the volume was then reduced by ¾ under vacuum. The resulting mixture was diluted with water (50 mL) and acidified to pH 1-2 with 2 M hydrochloric acid. This mixture was extracted with dichloromethane (3×100 mL). The combined organic phases were washed with saturated brine (150 mL), dried (MgSO$_4$) and concentrated under reduced pressure to afford 3-[2-azido-2-(2-hydroxyethoxy)ethoxy]benzoic acid (3.39 g, quantitative), as a colorless oil which was used without further purification.

$^1$H NMR (300 MHz, CDCl$_3$): δ 7.76 (dt, J=7.7, 1.2 Hz, 1H, ArH), 7.65 (dd, J=2.4, 1.4 Hz, 1H, ArH), 7.41 (t, J=8.0 Hz, 1H, ArH), 7.19 (ddd, J=8.2, 2.7, 1.0 Hz, 1H, ArH), 4.90 (t, J=5.1 Hz, 1H, CH), 4.21 (m, 2H, ArOCH$_2$), 4.03 (m, 1H, 0.5×OCH$_2$), 3.81 (m, 3H, 0.5×OCH$_2$+OCH$_2$).

3-[2-Azido-2-(2-ethoxycarbonylmethoxyethoxy)ethoxy]benzoic acid

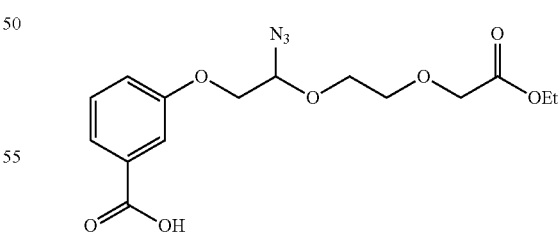

To an ice-cold solution of 3-[2-azido-2-(2-hydroxyethoxy)ethoxy]benzoic acid (1.42 g, 5.31 mmol) in anhydrous THF (18 mL) was added sodium hydride (0.64 g, 15.9 mmol) and the mixture was stirred at 0° C. for 10 min. Ethyl bromoacetate (1.95 g, 1.30 mL, 11.7 mmol) was added and the reaction mixture was allowed to warm up to room temperature over 5 h. The resulting mixture was quenched with ice-water (20 mL) and washed with dichloromethane (2×70 mL). The aqueous layer was acidified to pH 1-2 using 2 M hydrochloric acid and was extracted with dichloromethane (3×70 mL). The combined organic layers were dried (MgSO$_4$) and concentrated under reduced pressure to afford a colorless oil. This material was purified using a Biotage Isolera automated chromatography system under normal phase conditions (silica column, gradient of 0→60% ethyl acetate in dichloromethane) with detection at 254 nm to give 3-[2-azido-2-(2-ethoxycarbonylmethoxyethoxy)ethoxy] benzoic acid (0.62 g, 33%), as a colorless oil.

R$_f$ 0.45 (ethyl acetate-dichloromethane, 4:6 v/v).

$^1$H NMR (300 MHz, CDCl$_3$): δ 7.75 (dt, J=7.7, 1.2 Hz, 1H, ArH), 7.64 (dd, J=2.7, 1.5 Hz, 1H, ArH), 7.40 (t, J=8.0 Hz, 1H, ArH), 7.19 (ddd, J=8.3, 2.7, 1.0 Hz, 1H, ArH), 4.95 (dd, J=5.5, 4.6 Hz, 1H, CH), 4.14 (m, 7H, ArOCH$_2$+0.5× OCH$_2$+OCH$_2$+OCH$_2$C(O)), 3.86 (m, 3H, 0.5×OCH$_2$+ OCH$_2$), 1.28 (t, J=7.2 Hz, 3H, CH$_3$).

N-(2-Aminoethyl)-2,2,2-trifluoroacetamide Trifluoroacetate

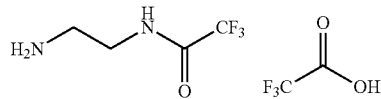 [SMILES: NCCNC(=O)C(F)(F)F ; O=C(O)C(F)(F)F]

To an ice-cold solution of N-Boc-ethylenediamine (2.08 g, 2.05 mL, 13.0 mmol) in anhydrous THF (8 mL) was slowly added ethyl trifluoroacetate (1.85 g, 1.55 mL, 13.0 mmol) and the reaction mixture was stirred at room temperature overnight. The resulting solution was concentrated under reduced pressure to give tert-butyl [2-(2,2,2-trifluoroacetamido)ethyl]carbamate (3.30 g, 99%), as a white solid which was used without further purification.

tert-Butyl [2-(2,2,2-trifluoroacetamido)ethyl]carbamate (1.04 g, 4.06 mmol) was dissolved in trifluoroacetic acid (5 mL) and stirred at room temperature for 30 min. The resulting mixture was concentrated under reduced pressure and the residual trifluoroacetic acid was azeotropically removed with chloroform (3×10 mL). The material obtained was dried in vacuo at 50° C. for 2 h to give N-(2-aminoethyl)-2,2,2-trifluoroacetamide trifluoroacetate (1.07 g, 99%), as a yellow oil which was used without further purification.

$^1$H NMR (300 MHz, DMSO-d$_6$): δ 9.58 (br, 1H, NH), 7.99 (br, 3H, NH$_3^+$), 3.43 (m, 2H, CH$_2$N), 2.97 (m, 2H, CH$_2$N).

[2-(1-Azido-2-{3-[2-(2,2,2-trifluoroacetamido)ethylcarbamoyl]phenoxy}ethoxy)ethoxy]acetic acid ethyl ester

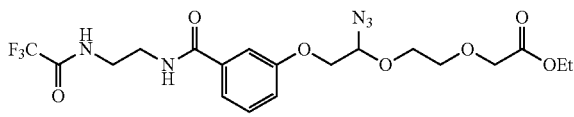 [SMILES: CCOC(=O)COCCOC(COc1cccc(C(=O)NCCNC(=O)C(F)(F)F)c1)N=[N+]=[N-]]

To a solution of N-(2-aminoethyl)-2,2,2-trifluoroacetamide trifluoroacetate (1.31 g, 4.86 mmol) in anhydrous DMF (25 mL) was added Hunig's base (1.57 g, 2.12 mL, 12.1 mmol), 3-[2-azido-2-(2-ethoxycarbonylmethoxyethoxy)ethoxy]benzoic acid (1.43 g, 4.05 mmol) and PyBOP (2.32 g, 4.45 mmol). The reaction mixture was stirred at room temperature for 20 h before being diluted with ethyl acetate (20 mL) and quenched with 1 M hydrochloric acid (40 mL). The aqueous phase was extracted with ethyl acetate (3×50 mL). The combined organic layers were washed with water (5×100 mL), saturated brine (100 mL), dried (MgSO$_4$) and concentrated under reduced pressure to give a yellow oil. This oil was purified using a Biotage Isolera automated chromatography system under normal phase conditions (silica column, gradient of 0→90% ethyl acetate in dichloromethane) with detection at 254 nm to give [2-(1-azido-2-{3-[2-(2,2,2-trifluoroacetamido)ethylcarbamoyl] phenoxy}ethoxy)ethoxy]acetic acid ethyl ester (1.75 g, 88%), as a colorless oil.

R$_f$ 0.48 (dichloromethane-ethyl acetate, 1:1, v/v).

$^1$H NMR (300 MHz, CDCl$_3$): δ 8.01 (br, 1H, NH), 7.39 (m, 3H, 3×ArH), 7.10 (dt, J=5.8, 3.0 Hz, 1H, ArH), 6.97 (br, 1H, NH), 4.93 (t, J=5.1 Hz, 1H, CH), 4.18 (m, 6H, ArOCH$_2$+ OCH$_2$+OCH$_2$C(O)), 4.04 (m, 1H, 0.5×OCH$_2$), 3.87 (m, 1H, 0.5×OCH$_2$), 3.81 (m, 2H, OCH$_2$), 3.69 (m, 2H, CH$_2$N), 3.62 (m, 2H, CH$_2$N), 1.30 (t, J=7.1 Hz, 3H, CH$_3$).

Sodium (2-{2-[3-(2-aminoethylcarbamoyl)phenoxy]-1-azidoethoxy}ethoxy)acetate

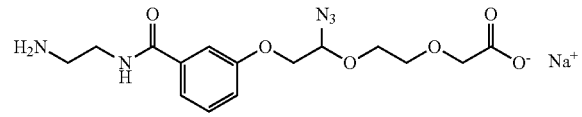 [SMILES: [N-]=[N+]=NC(COc1cccc(C(=O)NCCN)c1)OCCOCC(=O)[O-] ; [Na+]]

[2-(1-Azido-2-{3-[2-(2,2,2-trifluoroacetamido)ethylcarbamoyl]phenoxy}ethoxy)ethoxy]acetic acid ethyl ester (0.90 g, 1.83 mmol) was dissolved in ethanol (7 mL) and 4 M aqueous sodium hydroxide (7 mL) was added. The resulting mixture was stirred at room temperature for 2.5 h before being concentrated under reduced pressure. The material obtained was dissolved in water (55 mL) and washed with dichloromethane (2×48 mL). The aqueous layer was acidified to pH 2 using 1 M hydrochloric acid and washed with dichloromethane (2×50 mL). The organic layer was removed and discarded while the aqueous layer was neutralised to pH 8 using 1 M aqueous sodium hydroxide and evaporated under reduced pressure to give a white solid which was entrained with dichloromethane and methanol (2×95 mL, 1:1, v/v). The solid obtained was removed by suction filtration. The combined filtrates were concentrated under reduced pressure to give a gum. This impure gum was entrained with dichloromethane and methanol (10 mL, 9:1, v/v) and the insoluble white solid obtained was removed by suction filtration. The filtrate was concentrated under reduced pressure to give sodium (2-{2-[3-(2-aminoethylcarbamoyl)phenoxy]-1-azidoethoxy}ethoxy)acetate (0.76 g, quantitative), as a white foam.

$^1$H NMR (300 MHz, D$_2$O): δ 7.31 (m, 3H, 3×ArH), 7.11 (ddd, J=7.8, 2.6, 1.5 Hz, 1H, ArH), 4.99 (t, J=4.5 Hz, 1H, CH), 4.15 (m, 2H, ArOCH$_2$), 3.94 (m, 1H, 0.5×OCH$_2$), 3.79 (m, 3H, 0.5×OCH$_2$+OCH$_2$C(O)), 3.58 (m, 4H, OCH$_2$+ CH$_2$N), 3.10 (t, J=5.8 Hz, 2H, CH$_2$N).

2-(2-{1-Azido-2-[3-({2-[3,5-bis(methoxycarbonyl)
benzamido]ethyl}carbamoyl)phenoxy]
ethoxy}ethoxy)acetic acid (Fragment 2)

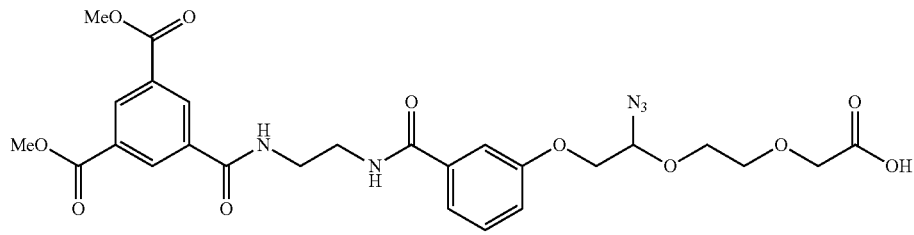 [SMILES: COC(=O)c1cc(C(=O)NCCNC(=O)c2cccc(OCC(N=[N+]=[N-])OCCOCC(=O)O)c2)cc(C(=O)OC)c1]

Trimethyl 1,3,5-benzenetricarboxylate (2.00 g, 7.93 mmol) was suspended in methanol (180 mL) and 1 M aqueous NaOH solution (7.14 mL) was added. The resulting mixture was stirred at room temperature for 18 h. The solution was concentrated under reduced pressure to afford a white solid which was partitioned between dichloromethane (150 mL) and saturated aqueous sodium bicarbonate solution (150 mL). The organic phase was separated and was extracted with saturated aqueous sodium bicarbonate solution (150 mL) before being discarded. The combined aqueous layers were acidified to pH 1-2 using concentrated hydrochloric acid and were extracted with ethyl acetate (2×150 mL). The combined organic layers were dried (MgSO$_4$) and concentrated to give 3,5-bis(methoxycarbonyl)benzoic acid (1.66 g, 88%), as a white solid.

3,5-bis(Methoxycarbonyl)benzoic acid (0.80 g, 3.36 mmol) was dissolved in ethyl acetate (20 mL) and N-hydroxysuccinimide (425 mg, 3.69 mmol) was added followed by N,N'-dicyclohexylcarbodiimide (0.76 g, 3.69 mmol). The resulting mixture was stirred at room temperature for 20 h. The suspension was filtered over Celite and the filtrate was washed with saturated aqueous sodium bicarbonate solution (2×100 mL), water (100 mL) and saturated brine (100 mL). The organic layer was dried (MgSO$_4$) and concentrated under reduced pressure to afford a white glassy solid. This material was purified using a Biotage Isolera automated chromatography system under normal phase conditions (silica column, gradient of 0→100% ethyl acetate in petrol) with detection at 254 nm to give N-hydroxysuccinimido 3,5-bis(methoxycarbonyl)benzoate, (1.06 g, 95%) as a white solid.

$R_f$ 0.44 (petrol-ethyl acetate, 4:6, v/v).

To a solution of N-hydroxysuccinimido 3,5-bis(methoxycarbonyl)benzoate (0.95 g, 2.83 mmol) and sodium (2-{2-[3-(2-aminoethylcarbamoyl)phenoxy]-1-azidoethoxy}ethoxy)acetate (0.92 g, 2.36 mmol) in anhydrous DMF (15 mL) was added Hunig's base (0.61 g, 0.83 mL, 4.72 mmol) and the reaction mixture was stirred at room temperature overnight. The resulting mixture was diluted with ethyl acetate (20 mL) and quenched with 1 M hydrochloric acid (20 mL). The aqueous phase was separated and was extracted with ethyl acetate (3×30 mL) and the combined organic phases were washed with water (5×50 mL) and saturated brine (50 mL). The resulting solution was dried (MgSO$_4$) before being concentrated under reduced pressure to give a white glassy solid. This material was purified using a Biotage Isolera automated chromatography system under normal phase conditions (silica column, gradient of 0→50% methanol in dichloromethane) with detection at 254 nm to give 2-(2-{1-azido-2-[3-({2-[3,5-bis(methoxycarbonyl)benzamido]ethyl}carbamoyl)phenoxy]ethoxy}ethoxy)acetic acid (Fragment 2) (0.92 g, 66%), as a white glassy solid.

$R_f$ 0.37 (dichloromethane-methanol, 83:17, v/v).

$^1$H NMR (300 MHz, d$_6$-DMSO) δ 9.42 (br s, 1H, NH), 8.99 (br s, 1H, NH), 8.66 (d, J=1.5 Hz, 2H, 2×ArH), 8.53 (t, J=1.5 Hz, 1H, ArH), 7.50 (m, 1H, ArH), 7.43 (d, J=7.7 Hz, 1H, ArH), 7.33 (t, J=7.9 Hz, 1H, ArH), 7.07 (dd, J=8.0, 2.4 Hz, 1H, ArH), 5.21 (t, J=5.0 Hz, 1H, CH), 4.24 (dd, J=10.6, 4.4 Hz, 1H, 0.5×ArOCH$_2$), 4.07 (dd, J=10.6, 5.9 Hz, 1H, 0.5×ArOCH$_2$), 3.88 (m, 8H, OCH$_2$+2×OCH$_3$), 3.84 (m, 1H, 0.5×OCH$_2$), 3.77 (m, 1H, 0.5×OCH$_2$), 3.62 (m, 2H, OCH$_2$C(O)), 3.40 (m, 4H, 2×CH$_2$N).

Pre-Cleavable SCGTP

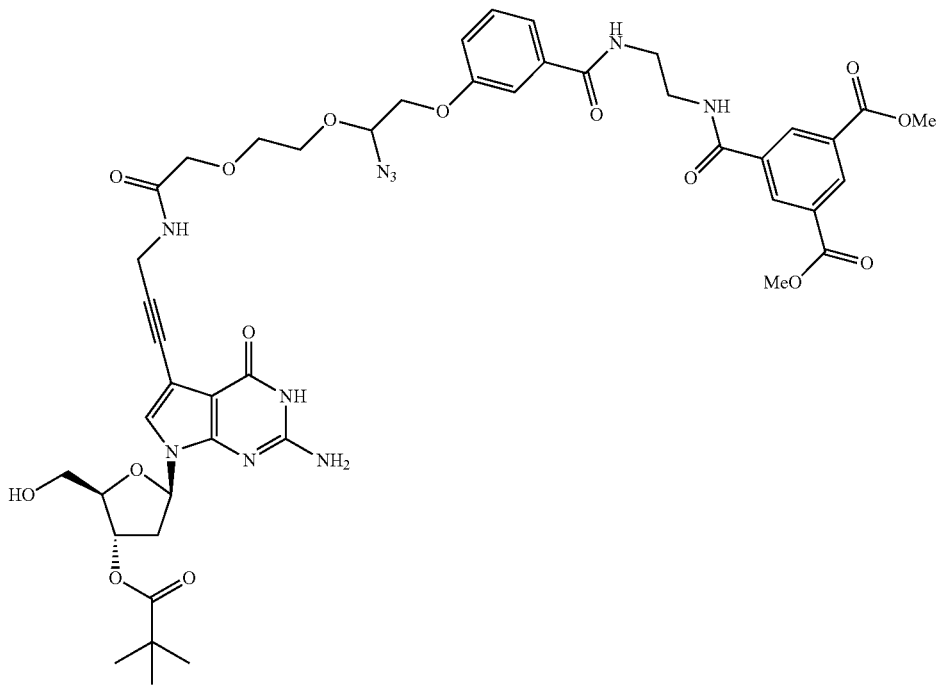 [SMILES: COC(=O)c1cc(C(=O)NCCNC(=O)c2cccc(OCC(N=[N+]=[N-])OCCOCC(=O)NCC#Cc3cn([C@H]4C[C@H](OC(=O)C(C)(C)C)[C@@H](CO)O4)c4nc(N)[nH]c(=O)c34)c2)cc(C(=O)OC)c1]

3'-O-Pivaloyl-7-deaza-7-(3-aminoprop-1-yn-1-yl)-2'-deoxyguanosine trifluoroacetate (152 mg, 0.29 mmol) was dissolved in anhydrous DMF (4 mL). Hunig's base (138 mg, 186 µL, 1.07 mmol) followed by 2-(2-{1-azido-2-[3-({2-[3, 5-bis(methoxycarbonyl)benzamido]ethyl}carbamoyl)phenoxy]ethoxy}ethoxy)acetic acid (157 mg, 0.27 mmol) and HBTU (107 mg, 0.28 mmol) were added. The reaction mixture was stirred at room temperature overnight. The resulting mixture was diluted with ethyl acetate (10 mL) and washed with 1 M hydrochloric acid (10 mL). The aqueous phase was separated and extracted with ethyl acetate (2×10 mL). The combined organic phases were washed with water (4×20 mL), saturated aqueous sodium bicarbonate solution (20 mL), saturated brine (20 mL), dried (MgSO$_4$) and concentrated under reduced pressure to give an orange solid. This crude solid was purified using a Biotage Isolera automated chromatography system under normal phase conditions (silica column, gradient of 4→26% methanol in dichloromethane) with detection at 254 nm to give Pre-Cleavable SCGTP (197 mg, 73%), as an orange solid.

R$_f$ 0.46 (dichloromethane-methanol, 92:8, v/v).

$^1$H NMR (300 MHz, DMSO-d$_6$): δ 10.54 (br, 1H, NH), 9.08 (br, 1H, NH), 8.68 (d, J=1.6 Hz, 2H, 2×ArH), 8.63 (br t, 1H, NH), 8.58 (t, J=1.6 Hz, 1H, ArH), 8.22 (t, J=5.7 Hz, 1H, NH), 7.46 (m, 2H, 2×ArH), 7.37 (t, J=7.8 Hz, 1H, ArH), 7.30 (s, 1H, deoxyguanosine CH), 7.13 (m, 1H, ArH), 6.35 (br s, 2H, deoxyguanosine NH$_2$), 6.24 (dd, J=9.2, 5.6 Hz, 1H, CHN), 5.25 (m, 1H, OH), 5.14 (m, 2H, CHOPiv+CHN$_3$), 4.23 (dd, J=10.4, 4.5 Hz, 1H, 0.5×ArOCH$_2$), 4.13 (m, 3H, 0.5×ArOCH$_2$+0.5×OCH$_2$+CH), 3.88 (m, 11H, CH$_2$N+1.5×OCH$_2$+2×OCH$_3$), 3.68 (m, 2H, deoxyguanosine CH$_2$), 3.55 (m, 2H, OCH$_2$C(O)), 3.46 (m, 4H, 2×CH$_2$N), 2.59 (m, 1H, deoxyguanosine 0.5×CH$_2$), 2.25 (m, 1H, deoxyguanosine 0.5×CH$_2$), 1.17 (s, 9H, 3×CH$_3$).

Penta-Triethylammonium Cleavable SCGTP

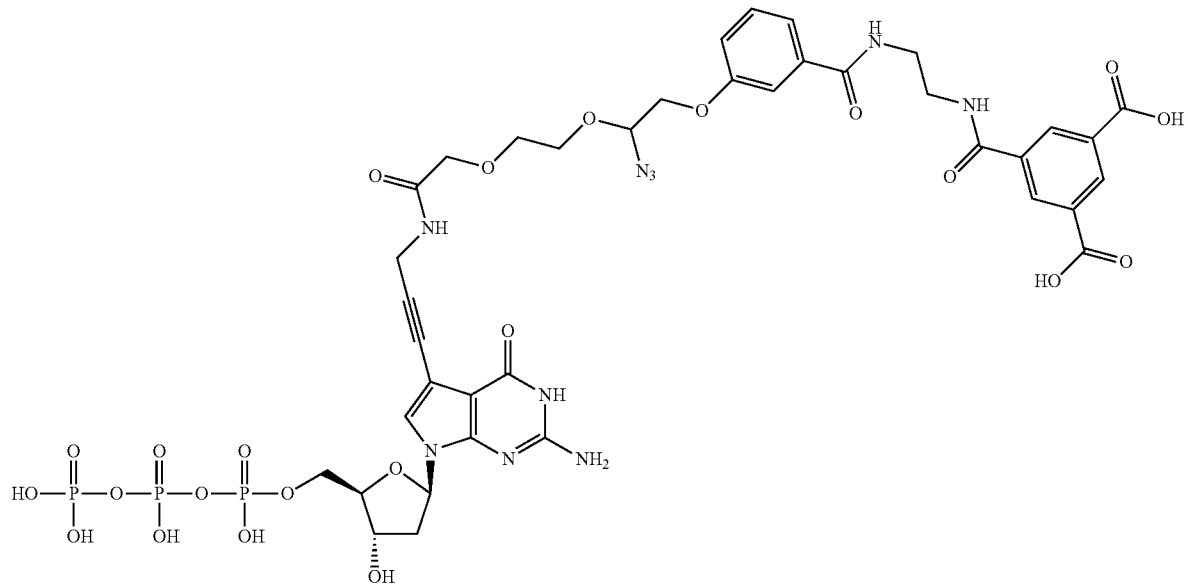 [SMILES: [N-]=[N+]=NC(COc1cccc(C(=O)NCCNC(=O)c2cc(C(=O)O)cc(C(=O)O)c2)c1)OCCOCC(=O)NCC#Cc1cn([C@H]2C[C@H](O)[C@@H](COP(=O)(O)OP(=O)(O)OP(=O)(O)O)O2)c2nc(N)[nH]c(=O)c12]

Pre-Cleavable SCGTP (185 mg, 0.19 mmol) was dissolved in 1,4-dioxane (0.57 mL) and anhydrous pyridine (191 μL) and the flask was evacuated and purged with a nitrogen atmosphere three times. 1.0 M Salicyl chlorophosphite solution in 1,4-dioxane (210 μL, 0.21 mmol) was added and the reaction mixture was stirred for 10 min. 0.5 M Tributylammonium pyrophosphate solution in anhydrous DMF (0.57 ml, 0.29 mmol) and tributylamine (148 mg, 190 μL, 0.80 mmol) were simultaneously added and the reaction mixture was stirred for 15 min. 1% Iodine solution in pyridine and water (3.8 mL, 92:8 v/v) was added and the solution was stirred for 15 min before being quenched with 5% aqueous sodium thiosulfate solution (100 μL) and the mixture was concentrated under reduced pressure. The residual material obtained was purified using a Biotage Isolera automated chromatography system under reversed-phase conditions ($C_{18}$ column, gradient of 0→40% acetonitrile in 0.1 M TEAA at pH 8) with detection at 272 nm to afford, after freeze-drying, impure protected Cleavable SCGTP (166 mg, 58%) which was used without further purification.

To a solution of protected Cleavable SCGTP (166 mg) in water (1.20 mL) was added 1 M aqueous sodium hydroxide (1.18 mL, 1.18 mmol) and the mixture was stirred at room temperature for 40 min. Further 1 M aqueous sodium hydroxide (0.60 mL, 0.60 mmol) was added and the mixture was stirred at for 1 h 40 min. 1 M Aqueous sodium hydroxide (0.20 mL, 0.20 mmol) was added, the mixture was stirred for 30 min and the solution was diluted with 1 M aqueous triethylammonium bicarbonate (TEAB) solution (pH 8, 5 mL). The resulting solution was lyophilized overnight (220 mg) and the material was dissolved in 1 M aqueous triethylammonium bicarbonate (TEAB) (2.0 mL) to give a concentration of 110 mg/mL. This solution was purified by semi-preparative HPLC injecting 80 μL portions and collecting the eluent containing the pure substance. The combined fractions were reduced in volume by removing the acetonitrile and most of the water and finally lyophilized to give penta-triethylammonium Cleavable SCGTP (97 mg, 58%), as a white solid.

HPLC Conditions:
Column: Phenomenex Luna C18(2), 15 mm×250 mm
Solvent Gradient: 90% 0.1 M aqueous TEAB (pH 7.0) to 85.6% 0.1 M aqueous TEAB (pH 7.0) over 22 min with the balance being acetonitrile.
Flow Rate: 7.8 mL/min
Temp: 30° C.
Detection: UV at 290 nm
Under these conditions the product had a retention time of ca. 18-19.5 min.

Example 8

Synthesis of Photocleavable Linkers

Synthesis of a 3-(hydroxymethyl)naphthalen-2-ol derivative (3-(Allyloxy)naphthalen-2-yl)methyl (2,5-dioxopyrrolidin-1-yl)carbonate

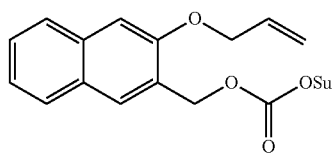

To a stirred suspension of methyl 3-hydroxy-2-naphthoate (498 mg, 2.47 mmol) and potassium carbonate (683 mg, 4.94 mmol) in acetone (8.2 mL) in a vial was added allyl bromide (419 mg, 321 μL, 3.71 mmol). The vial was sealed and heated at 80° C. for 3.5 h. After cooling to room temperature, allyl bromide (419 mg, 321 μL, 3.71 mmol) and potassium iodide (616 mg, 3.71 mmol) were added. The vial was sealed and heated at 80° C. for a further 72 h. After cooling to room temperature, the reaction mixture was concentrated under reduced pressure and the residue dissolved in ethyl acetate (10 mL), washed with water (2×10 mL), 3 M sodium hydroxide (10 mL), saturated brine (10 mL), dried (MgSO$_4$) and concentrated to give methyl 3-(allyloxy)-2-naphthoate (615 mg, 98%), as a yellow oil that was used without further purification.

A stirred solution of methyl 3-(allyloxy)-2-naphthoate (300 mg, 1.24 mmol) in anhydrous THF (6.2 mL) was cooled in an ice-bath under nitrogen and a solution of 1.0 M DIBAL in hexane (2.73 mL, 2.73 mmol) was added dropwise. Stirring was continued overnight during which time the reaction mixture was allowed to warm to room temperature. The resulting mixture was cooled to 0° C., quenched with saturated aqueous sodium bicarbonate solution (5 mL) and diluted with ethyl acetate (10 mL) and water (20 mL). The layers were separated and the aqueous layer was extracted with ethyl acetate (2×10 mL). The combined organic layers were washed with water (2×30 mL), saturated brine (10 mL), dried (MgSO$_4$) and concentrated to give a yellow oil. This crude material was purified using a Biotage Isolera automated chromatography system under normal phase conditions (silica column, gradient of 5→40% petrol in ethyl acetate) with detection at 254 nm to afford (3-(allyloxy)naphthalen-2-yl)methanol (220 mg, 83%), as a yellow oil.

R$_f$=0.20 (ethyl acetate-petrol, 1:4 v/v)

To a stirred solution of (3-(allyloxy)naphthalen-2-yl) methanol (215 mg, 1.00 mmol) in anhydrous acetonitrile (5 mL) under nitrogen was added N,N'-disuccinimidyl carbonate (335 mg, 1.31 mmol) and pyridine (103 mg, 106 μL, 1.31 mmol) and stirring was continued at room temperature overnight. The mixture was evaporated to dryness and the residue dissolved in dichloromethane (20 mL), and washed with saturated aqueous sodium bicarbonate solution (3×20 mL), water (20 mL), saturated brine (20 mL), dried (MgSO$_4$) and concentrated to give (3-(allyloxy)naphthalen-2-yl)methyl (2,5-dioxopyrrolidin-1-yl)carbonate (263 mg, 74%), as a white solid that was used without further purification.

(3-Hydroxynaphthalen-2-yl)methyl (2-(benzyloxy)-1-methoxyethyl)carbamate

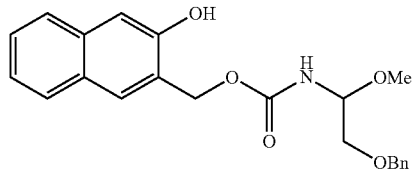 [SMILES: COC(COCc1ccccc1)NC(=O)OCc1cc2ccccc2cc1O]

A solution of triethylamine (111 mg, 153 μL, 1.10 mmol) in dioxane (1 mL) was added to a slurry of H-Ser(OBn)-OH (143 mg, 0.73 mmol) in water (2 mL). Once a clear solution was obtained, a solution of (3-(allyloxy)naphthalen-2-yl) methyl (2,5-dioxopyrrolidin-1-yl)carbonate (260 mg, 0.73 mmol) in anhydrous dioxane (2 mL) was added and stirring was continued at room temperature overnight. The solution was poured into water (6 mL), acidified to ~pH 3.0 with 2.0 M aqueous sodium bisulfate and extracted with ethyl acetate (3×30 mL). The combined organic layers were washed with water (3×30 mL), saturated brine (30 mL), dried (MgSO$_4$) and concentrated to give N-(((3-(allyloxy)naphthalen-2-yl) methoxy)carbonyl)-O-benzylserine (290 mg, 91%), as a colorless oil that was used without further purification.

A stirred solution of lead(IV) acetate (357 mg, 0.80 mmol) in anhydrous DMF (0.75 mL) was cooled in an ice-bath under nitrogen and a solution of N-(((3-(allyloxy) naphthalen-2-yl)methoxy)carbonyl)-O-benzylserine (290 mg, 0.67 mmol) in anhydrous DMF (0.75 mL) was added dropwise. Stirring was continued for 30 min at this temperature and for a further 4 h during which time the reaction mixture was allowed to warm to room temperature. Ethyl acetate (10 mL) was added and the mixture was quenched with saturated sodium bicarbonate solution (10 mL). The layers were separated and the aqueous layer was extracted with ethyl acetate (3×10 mL). The combined organic layers were washed with saturated aqueous sodium bicarbonate solution (10 mL), saturated brine (10 mL), dried (MgSO$_4$) and concentrated to afford 1-((((3-(allyloxy)naphthalen-2-yl)methoxy)carbonyl)amino)-2-(benzyloxy)ethyl acetate (326 mg), as a yellow oil.

1-((((3-(Allyloxy)naphthalen-2-yl)methoxy)carbonyl) amino)-2-(benzyloxy)ethyl acetate (324 mg) was dissolved in anhydrous methanol (3.5 mL). The solution was heated under microwave irradiation at 100° C. for 30 min before being concentrated under reduced pressure. Residual acetic acid was removed azeotropically with methanol (3×3 mL) to afford (3-(allyloxy)naphthalen-2-yl)methyl (2-(benzyloxy)-1-methoxyethyl)carbamate (276 mg, 98% over 2 steps), as a yellow/orange oil that was used without further purification.

To a stirred solution of (3-(allyloxy)naphthalen-2-yl) methyl (2-(benzyloxy)-1-methoxyethyl)carbamate (127 mg, 0.30 mmol) and 5,5-dimethyl-1,3-cyclohexanedione (127 mg, 0.90 mmol) in anhydrous DMF (5 mL) under nitrogen was added Pd(PPh$_3$)$_4$ (104 mg, 0.09 mmol) and stirring was continued at room temperature overnight. The mixture was evaporated to dryness and the residue taken up in water (10 mL) and extracted with ethyl acetate (5×10 mL). The combined organic layers were washed with water (4×10 mL), saturated brine (10 mL), dried (MgSO$_4$) and concentrated to give a dark orange sticky solid. This crude material was initially purified using a Biotage Isolera automated chromatography system under normal phase conditions (silica column, gradient of 0.5→4% methanol in dichloromethane) with detection at 254 nm to afford impure (3-hydroxynaphthalen-2-yl)methyl (2-(benzyloxy)-1-methoxyethyl)carbamate. Further purification using a Biotage Isolera automated chromatography system under normal phase conditions (silica column, gradient of 0→1% methanol in diethyl ether) with detection at 254 nm gave (3-hydroxynaphthalen-2-yl)methyl (2-(benzyloxy)-1-methoxyethyl)carbamate (105 mg, 92%) as a pale brown semi-solid.

R$_f$=0.80 (methanol-diethyl ether, 0.5:95.5 v/v)

Synthesis of a 2-hydroxymethyl-p-hydroquinone derivative 2,5-Dimethoxybenzyl (2,5-dioxopyrrolidin-1-yl)carbonate

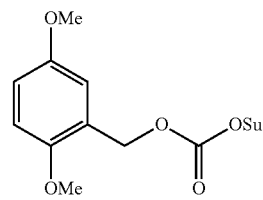

To 2,5-dimethoxybenzyl alcohol (0.67 g, 3.98 mmol) in anhydrous acetonitrile (20 mL) was added N,N'-disuccinimidyl carbonate (1.33 g, 5.18 mmol) followed by pyridine (409 mg, 419 µL, 5.18 mmol) and the mixture was stirred overnight at room temperature. The mixture was concentrated, reconstituted with dichloromethane (60 mL) and was washed with saturated aqueous sodium bicarbonate (3×60 mL), water (60 mL), saturated brine (60 mL), dried (MgSO$_4$) and concentrated. The material was dried azeotropically with acetonitrile (3×20 mL) and diethyl ether (20 mL) to give 2,5-dimethoxybenzyl (2,5-dioxopyrrolidin-1-yl)carbonate (1.15 g, 93%), as a white solid.

Towards (3,6-Dioxocyclohexa-1,4-dien-1-yl)methyl (2-(benzyloxy)-1-methoxyethyl)carbamate

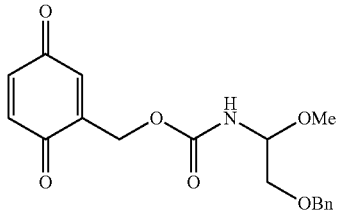 [SMILES: COC(COCc1ccccc1)NC(=O)OCC1=CC(=O)C=CC1=O]

To O-benzylserine (0.73 g, 3.22 mmol) in water (10 mL) was added triethylamine (0.56 g, 0.78 mL, 5.58 mmol) in dioxane (10 mL) followed by 2,5-dimethoxybenzyl (2,5-dioxopyrrolidin-1-yl)carbonate (1.15 g, 3.22 mmol) and the mixture was stirred overnight at room temperature. The resulting mixture was diluted with water (30 mL) and was extracted with ethyl acetate (3×50 mL). The combined organic layers were washed with water (3×50 mL), saturated brine (50 mL), dried (MgSO$_4$) and concentrated to give O-benzyl-N-(((2,5-dimethoxybenzyl)oxy)carbonyl)serine (1.37 g, 95%), as a white solid.

To lead (IV) tetraacetate (1.84 g, 4.16 mmol) in anhydrous DMF (4 mL) at −10° C. was added dropwise O-benzyl-N-(((2,5-dimethoxybenzyl)oxy)carbonyl)serine (1.35 g, 3.47 mmol) in anhydrous DMF (4 mL). The mixture was stirred at this temperature for 30 min followed by room temperature overnight. The resulting mixture was diluted with ethyl acetate (60 mL) and washed with saturated aqueous sodium bicarbonate (60 mL). The aqueous layer was extracted with ethyl acetate (30 mL) and the combined organic extracts were washed with saturated aqueous sodium bicarbonate (2×30 mL), saturated brine (30 mL), dried (MgSO$_4$) and concentrated to afford 2-(benzyloxy)-1-((((2,5-dimethoxybenzyl)oxy)carbonyl)amino)ethyl acetate (1.38 g, 99%), as a yellow oil.

2-(Benzyloxy)-1-((((2,5-dimethoxybenzyl)oxy)carbonyl)amino)ethyl acetate (0.95 g, 2.35 mmol) in methanol (10 mL) was heated in a microwave reactor at 100° C. for 30 min. The resulting solution was concentrated and dried azeotropically with methanol (3×10 mL) to give 2,5-dimethoxybenzyl (2-(benzyloxy)-1-methoxyethyl)carbamate (0.84 g, 95%), as an orange oil.

Synthesis of a 2-Hydroxymethylanthraquinone Carbonate Derivative (9,10-Dioxo-9,10-dihydroanthracen-2-yl)methyl (2,5-dioxopyrrolidin-1-yl)carbonate

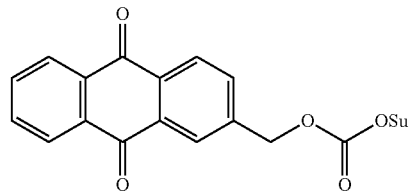

To a slurry of sodium acetate (1.50 g, 18.3 mmol) in glacial acetic acid (10 mL) and acetic anhydride (5 mL) was added 2-bromomethyl-9,10-anthraquinone (0.50 g, 1.66 mmol) and the reaction mixture was heated at reflux overnight under nitrogen. After cooling to room temperature, the solvent was evaporated and the residue was slurried in water (10 mL) and collected by suction filtration using a Buchner funnel. This material was washed with water (2×10 mL) and dried in vacuo at room temperature overnight to afford 2-methylacetate-9,10-anthraquinone (464 mg, quantitative), as a pale yellow solid.

A solution of sodium hydroxide (82 mg, 2.05 mmol) in water (2.3 mL) was added to a suspension of 2-methylacetate-9,10-anthraquinone (459 mg, 1.64 mmol) and the mixture was heated at reflux for 4 h. After cooling to room temperature, the reaction mixture was diluted with water (18 mL) and the resulting solid collected by suction filtration. This material was washed with water (2×6 mL) and dried in vacuo at 40° C. overnight to afford 2-hydroxymethyl-9,10-anthraquinone (361 mg, 92%), as a pale yellow solid.

To a stirred solution of 2-hydroxymethyl-9,10-anthraquinone (358 mg, 1.50 mmol) in anhydrous acetonitrile (7.5 mL) under nitrogen was added N,N'-disuccinimidyl carbonate (500 mg, 1.95 mmol) and pyridine (154 mg, 158 µL, 1.95 mmol) and stirring was continued at room temperature overnight. The resulting mixture was evaporated to dryness and the residue dissolved in dichloromethane (30 mL). The solution was washed with saturated aqueous sodium bicarbonate solution (30 mL), the layers were then separated and the aqueous layer was extracted with chloroform (4×30 mL). The combined organics were washed with saturated aqueous sodium bicarbonate solution (3×30 mL), water (30 mL), saturated brine (30 mL), dried (MgSO$_4$) and concentrated to afford (9,10-dioxo-9,10-dihydroanthracen-2-yl)methyl (2,5-dioxopyrrolidin-1-yl)carbonate (263 mg), as a pale yellow solid that was used without further purification.

Further material was obtained by diluting the aqueous layer with ethyl acetate (50 mL) and then collecting the resulting solid by suction filtration. This was dried in vacuo at room temperature for 72 h to afford (9,10-dioxo-9,10-dihydroanthracen-2-yl)methyl (2,5-dioxopyrrolidin-1-yl)carbonate (321 mg), as a pale yellow solid that was used without further purification.

(9,10-Dioxo-9,10-dihydroanthracen-2-yl)methyl (2-(benzyloxy)-1-methoxyethyl)carbamate

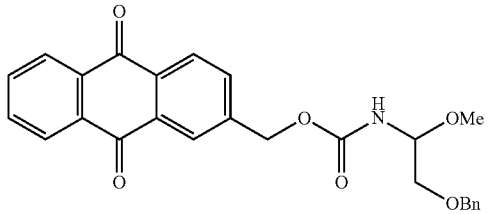 [SMILES: COC(COCc1ccccc1)NC(=O)OCc1ccc2c(c1)C(=O)c1ccccc1C2=O]

A solution of triethylamine (126 mg, 174 µL, 1.25 mmol) in dioxane (3.4 mL) was added to a slurry of H-Ser(OBn)-OH (162 mg, 0.83 mmol) in water (2.25 mL). Once a clear solution was obtained, (9,10-dioxo-9,10-dihydroanthracen-2-yl)methyl (2,5-dioxopyrrolidin-1-yl)carbonate (315 mg, 0.83 mmol) was added and stirring was continued at room temperature overnight. The solution was poured into water (6 mL), acidified to ~pH 3.0 with 2.0 M aqueous sodium bisulfate and extracted with ethyl acetate (3×30 mL). The combined organic layers were washed with water (3×30 mL), saturated brine (30 mL), dried (MgSO$_4$) and concentrated to afford O-benzyl-N-(((9,10-dioxo-9,10-dihydroanthracen-2-yl)methoxy)carbonyl)serine (236 mg, 62%), as a pale yellow solid.

A stirred solution of lead(IV) acetate (266 mg, 0.60 mmol) in anhydrous DMF (0.55 mL) was cooled in an ice-bath under nitrogen and a solution of O-benzyl-N-(((9,10-dioxo-9,10-dihydroanthracen-2-yl)methoxy)carbonyl)serine (230 mg, 0.50 mmol) in anhydrous DMF (0.55 mL) was added dropwise. Stirring was continued for 30 min at this temperature followed by a further 3 h during which time the reaction mixture was allowed to warm to room temperature. Ethyl acetate (10 mL) was added and the mixture was quenched with saturated aqueous sodium bicarbonate solution (10 mL). The layers were separated and the aqueous layer was extracted with ethyl acetate (3×10 mL). The combined organic layers were washed with saturated aqueous sodium bicarbonate solution (10 mL), saturated brine (10 mL), dried (MgSO$_4$) and concentrated to give 2-(benzyloxy)-1-((((9,10-dioxo-9,10-dihydroanthracen-2-yl)methoxy)carbonyl)amino)ethyl acetate (270 mg), as a yellow oil.

2-(Benzyloxy)-1-((((9,10-dioxo-9,10-dihydroanthracen-2-yl)methoxy)carbonyl)amino)ethyl acetate (270 mg) was dissolved in anhydrous methanol (2 mL) and anhydrous 1,2-dimethoxyethane (1.2 mL). The solution was heated under microwave irradiation at 100° C. for 30 min before being concentrated under reduced pressure. Residual acetic acid was removed azeotropically with methanol (3×3 mL) to afford (9,10-dioxo-9,10-dihydroanthracen-2-yl)methyl (2-(benzyloxy)-1-methoxyethyl)carbamate (201 mg, 90% over 2 steps), as a pale yellow solid.

Synthesis of a 2-Hydroxy-Substituted Linker Derivative 1-((4-(tert-Butyl)phenoxy)carbonyl)-3-methyl-1H-imidazol-3-ium tetrafluoroboroate

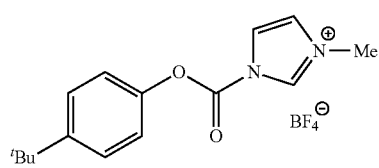

To 4-tert-butylphenol (500 mg, 3.33 mmol) in anhydrous dichloromethane (10 mL) was added carbonyl diimidazole (567 mg, 3.50 mmol) and the mixture was stirred overnight at room temperature. The impure material was dry-loaded onto silica and was purified using a Biotage Isolera automated chromatography system under normal phase conditions (silica column, gradient of 7→77% ethyl acetate in petrol) with detection at 254 nm to give 4-(tert-butyl)phenyl 1H-imidazole-1-carboxylate (461 mg, 57%), as a white solid.

R$_f$=0.45 (ethyl acetate-petrol, 3:7 v/v)

4-(tert-Butyl)phenyl 1H-imidazole-1-carboxylate (50 mg, 0.21 mmol) and trimethyloxonium tetrafluoroborate (31 mg, 0.21 mmol) were stirred in anhydrous dichloromethane (1 mL) overnight at room temperature. The mixture was concentrated to give 1-((4-(tert-butyl)phenoxy)carbonyl)-3-methyl-1H-imidazol-3-ium tetrafluoroboroate (55 mg), which was used without purification.

5-(2-(((4-(tert-Butyl)phenoxy)carbonyl)oxy)acetyl)-2-hydroxybenzoic acid

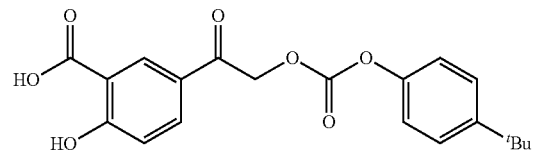 [SMILES: CC(C)(C)c1ccc(OC(=O)OCC(=O)c2ccc(O)c(C(=O)O)c2)cc1]

Benzyl bromide (2.49 g, 1.65 mL, 6.94 mmol) was added dropwise to a solution of 5-acetyl-2-hydroxybenzoic acid (1.00 g, 5.56 mmol) and potassium carbonate (1.98 g, 6.94 g) in anhydrous DMF (15 mL) and the mixture was stirred for 16 h at 120° C. The mixture was allowed to cool to room temperature and was diluted with water (15 mL) and extracted with ethyl acetate (4×15 mL). The combined organic layers were washed with water (5×15 mL), saturated brine (15 mL), dried (MgSO$_4$) and concentrated. The impure residue was purified using a Biotage Isolera automated chromatography system under normal phase conditions (silica column, gradient of 5→100% ethyl acetate in petrol) with detection at 254 nm to give benzyl 5-acetyl-2-(benzyloxy)benzoate (1.86 g, 93%), as an off-white solid.

R$_f$=0.45 (ethyl acetate-petrol, 1:4 v/v)

Phenyltrimethylammonium tribromide (PTT) (1.56 g, 4.16 mmol) was added portionwise to benzyl 5-acetyl-2-(benzyloxy)benzoate (1.50 g, 4.16 mmol) in anhydrous THF (15 mL) and the mixture was stirred for 20 min. Ice-cold water (90 mL) was added and crystallisation was induced by storing at 4° C. The crystals were collected by suction filtration using a Buchner funnel and were washed with diethyl ether (20 mL) to give benzyl 2-(benzyloxy)-5-(2-bromoacetyl)benzoate (1.51 g, 83%), as an off-white crystalline solid after drying in vacuo for 1 h at 40° C.

To a suspension of benzyl 2-(benzyloxy)-5-(2-bromoacetyl)benzoate (1.51 g, 3.44 mmol) in ethanol (4 mL) was added sodium acetate (310 mg, 3.78 mmol) in water (2 mL), and acetic acid (200 µL) and the mixture was stirred for 3 h at 80° C. The resulting mixture was allowed to cool to room temperature and crystallisation was induced by storing at 4° C. The crystals were collected by suction filtration using a Buchner funnel and were washed sequentially with ice-cold water (10 mL) and ice-cold diethyl ether (10 mL) to afford 5-(2-acetoxyacetyl)-2-(benzyloxy)benzoate (707 mg, 49%), as a white crystalline solid after drying in vacuo for 1 h at 40° C.

To benzyl 5-(2-acetoxyacetyl)-2-(benzyloxy)benzoate (300 mg, 0.72 mmol) in methanol (3 mL) was added 2 M hydrochloric acid (1.8 mL) and the solution was stirred at 70° C. for 1 h. The resulting mixture was allowed to cool to room temperature and was diluted with water (20 mL) and extracted into ethyl acetate (20 mL). The organic layer was dried (MgSO$_4$) and concentrated. The impure material was purified using a Biotage Isolera automated chromatography system under normal phase conditions (silica column, gradient of 12→85% ethyl acetate in petrol) with detection at 254 nm to give benzyl 2-(benzyloxy)-5-(2-hydroxyacetyl) benzoate (225 mg, 83%), as a white solid.

R$_f$=0.42 (ethyl acetate-petrol, 1:1 v/v)

To benzyl 2-(benzyloxy)-5-(2-hydroxyacetyl)benzoate (80 mg, 0.21 mmol) in anhydrous THF (2 mL) was added 1-((4-(tert-butyl)phenoxy)carbonyl)-3-methyl-1H-imidazol-3-ium tetrafluoroboroate (55 mg, 0.21 mmol) and the mixture was stirred at room temperature overnight. TLC showed that the reaction was incomplete and the mixture was heated at reflux for 5 h. The impure material was dry-loaded onto silica and was purified using a Biotage Isolera automated chromatography system under normal phase conditions (silica column, gradient of 10→100% ethyl acetate in petrol) with detection at 254 nm to give benzyl 2-(benzyloxy)-5-(2-(((4-(tert-butyl)phenoxy)carbonyl)oxy)acetyl)benzoate (88 mg, 80%), as a colorless oil.

R$_f$=0.45 (ethyl acetate-petrol, 1:1 v/v)

10% Palladium on carbon (8.5 mg) was cautiously wetted with ethyl acetate (2 mL), under nitrogen, and benzyl 2-(benzyloxy)-5-(2-(((4-(tert-butyl)phenoxy)carbonyl)oxy) acetyl)benzoate (85 mg, 0.16 mmol) was added. An atmosphere of hydrogen was introduced via a balloon and the mixture was stirred for 2 h at room temperature. The catalyst was removed by filtration of the suspension through a thin layer of Celite and the filtrate was concentrated to give 5-(2-(((4-(tert-butyl)phenoxy)carbonyl)oxy)acetyl)-2-hydroxybenzoic acid (60 mg, 100%), as a white solid.

Example 9

Synthesis of Chemically Cleavable Linkers

Methyl 2-(azidomethyl)benzoate

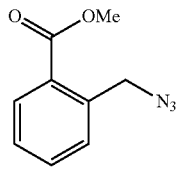 [SMILES: COC(=O)c1ccccc1CN=[N+]=[N-]]

To methyl 2-(bromomethyl)benzoate (250 mg, 1.09 mmol) in anhydrous DMF (4 mL) was added sodium azide (565 mg, 8.70 mmol) and the solution was stirred at room temperature overnight. The resulting solution was diluted with water (40 mL) and extracted into ethyl acetate (3×50 mL). The combined organic layers were washed with water (5×40 mL), saturated brine (40 mL), dried (MgSO$_4$) and concentrated to give methyl 2-(azidomethyl)benzoate (203 mg, 97%), as a pale yellow solid.

2-(Azidomethyl)benzoic acid

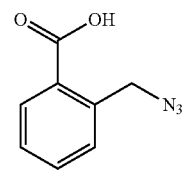 [SMILES: [N-]=[N+]=NCc1ccccc1C(=O)O]

To methyl 2-(azidomethyl)benzoate (200 mg, 1.04 mmol) in THF (1 mL) was added 3 M sodium hydroxide (1.5 mL) and the solution was stirred at room temperature overnight. The resulting solution was diluted with water (10 mL) and washed with diethyl ether (3×10 mL). The aqueous layer was adjusted to pH 2 with 2 M hydrochloric acid and subsequently extracted with ethyl acetate (3×20 mL). The combined organic layers were washed with saturated brine (10 mL), dried (MgSO$_4$) and concentrated to give 2-(azidomethyl)benzoic acid (174 mg, 95%), as a white solid.

2-(Azidomethyl)benzoyl chloride

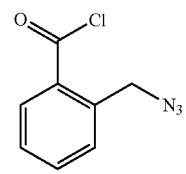 [SMILES: [N-]=[N+]=NCc1ccccc1C(=O)Cl]

To 2-(azidomethyl)benzoic acid (170 mg, 0.96 mmol) and anhydrous DMF (3.5 mg, 4 µL, 0.05 mmol) in anhydrous THF (3 mL) was added thionyl chloride (342 mg, 210 µL, 2.88 mmol) and the mixture was stirred at 60° C. for 2 h. The reaction mixture was allowed to cool to room temperature and was concentrated to give 2-(azidomethyl)benzoyl chloride (181 mg, quantitative), as a yellow solid that was used immediately without purification.

4-Nitrophenyl 2-(azidomethyl)benzoate

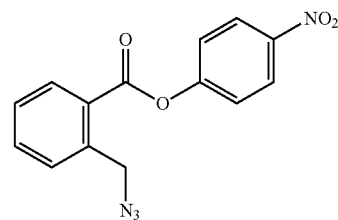 [SMILES: [N-]=[N+]=NCc1ccccc1C(=O)Oc1ccc([N+](=O)[O-])cc1]

To 2-(azidomethyl)benzoyl chloride (90 mg, 0.48 mmol) and DMAP (117 mg, 0.96 mmol) in anhydrous dichloromethane (1 mL) was added dropwise 4-nitrophenol (74 mg, 0.53 mmol) in anhydrous dichloromethane (1 mL) and the reaction mixture was stirred at room temperature overnight. The resulting impure material was dry-loaded onto silica and was purified using a Biotage Isolera automated chromatography system under normal phase conditions (silica column, gradient of 12→100% ethyl acetate in petrol) with detection at 254 nm to give 4-nitrophenyl 2-(azidomethyl)benzoate (89 mg, 55%), as a white solid.

$R_f$=0.54 (ethyl acetate-petrol, 1:1 v/v)

7-Hydroxy-4-methylcoumarinyl 2-(azidomethyl)benzoate

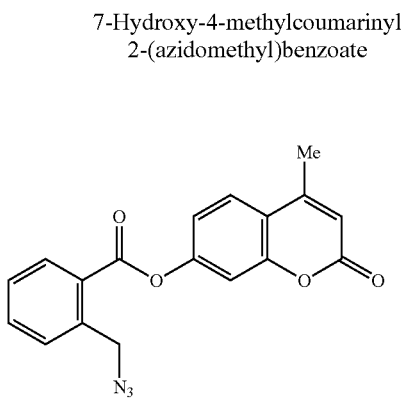

To 2-(azidomethyl)benzoyl chloride (90 mg, 0.48 mmol) and DMAP (117 mg, 0.96 mmol) in anhydrous dichloromethane (1 mL) was added dropwise 4-methylumbelliferone (93 mg, 0.53 mmol) in anhydrous dichloromethane (1 mL) and the reaction mixture was stirred at room temperature overnight. The resulting impure material was dry-loaded onto silica and was purified using a Biotage Isolera automated chromatography system under normal phase conditions (silica column, gradient of 12→75% ethyl acetate in petrol) with detection at 254 nm to give 7-hydroxy-4-methylcoumarinyl 2-(azidomethyl)benzoate (80 mg, 56%), as a white solid.

$R_f$=0.57 (ethyl acetate-petrol, 1:1 v/v)

What is claimed is:

1. A reporter composition, comprising:
   a nucleotide or its derivative;
   a high charge mass moiety comprising an aromatic or aliphatic skeleton, comprising one or more charged groups selected from the group consisting of a tertiary amino group, a carboxyl group, a hydroxyl group, a phosphate group, a phenolic hydroxy group, and any combinations thereof, wherein the one or more charged groups comprise a charge mass that is sufficient to generate a detectable change in a property of a sensitive detection nanostructure or nano-/micro-sensor operably coupled to the reporter composition; and
   a linker molecule attached to the nucleotide or its derivative and the high charge mass moiety, wherein the linker molecule comprises a linear or branched chain comprising one or more selected from the group consisting of an alkyl group, an oxy alkyl group, an alcohol group, a carboxyl group, an amine group, an amide group, an aromatic group, and a naphthalene group, and any combinations thereof,
   wherein the linker is configured such that the linker and the high charge moiety to which the linker is attached extend out from a DNA polymerase complex such that the linker and the high charge moiety do not interfere with polymerization and/or hydrogen bonding between the bases of nucleotides, and wherein the high charge mass moiety is configured to be cleaved after detection,
   wherein the high charge mass moiety comprises one or more selected from the group consisting of the following compounds 1-5, and any combinations thereof:

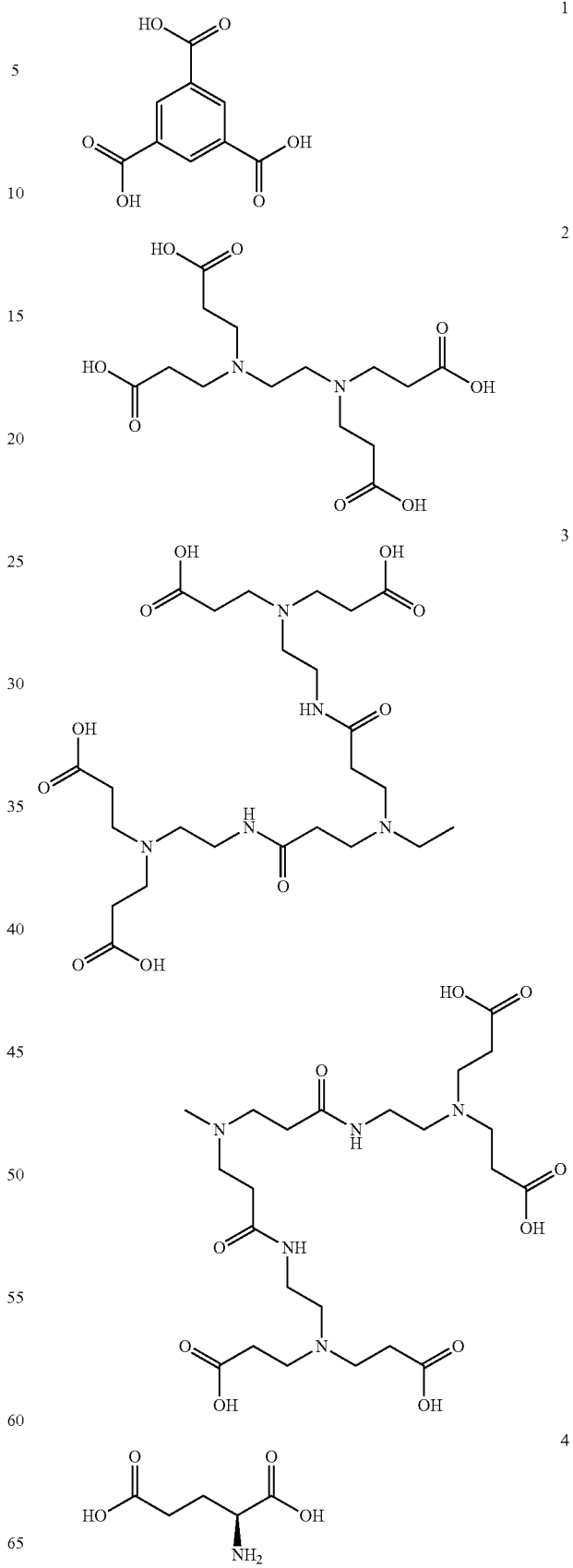

5

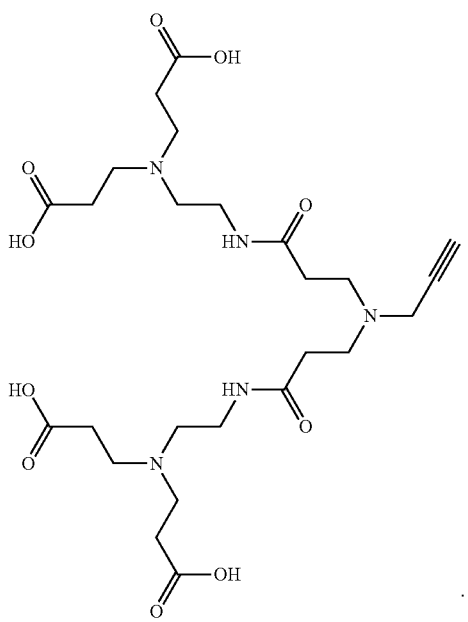

2. The reporter composition of claim 1, wherein the linker molecule is photocleavable.

3. The reporter composition of claim 1, wherein the nucleotide is selected from the group consisting of a deoxyribonucleotide, a ribonucleotide, a peptide nucleotide, a morpholino, a locked nucleotide, a glycol nucleotide, a threose nucleotide, and a synthetic nucleotide, and any isoforms thereof.

4. The reporter composition of claim 1, wherein the linker molecule is chemically cleavable.

5. The reporter composition of claim 4, wherein the chemically cleavable linker molecule comprises one or more selected from the group consisting of: 4-Nitrophenyl 2-(azidomethyl)benzoate, 7-Hydroxy-4-methylcoumarinyl 2-(azidomethyl)benzoate, and any combinations thereof.

6. The reporter composition of claim 2, wherein the photocleavable cleavable linker molecule comprises one or more selected from the group consisting of the following compounds 6-10, and any combinations thereof:

6

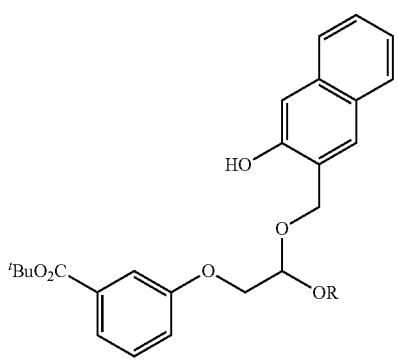

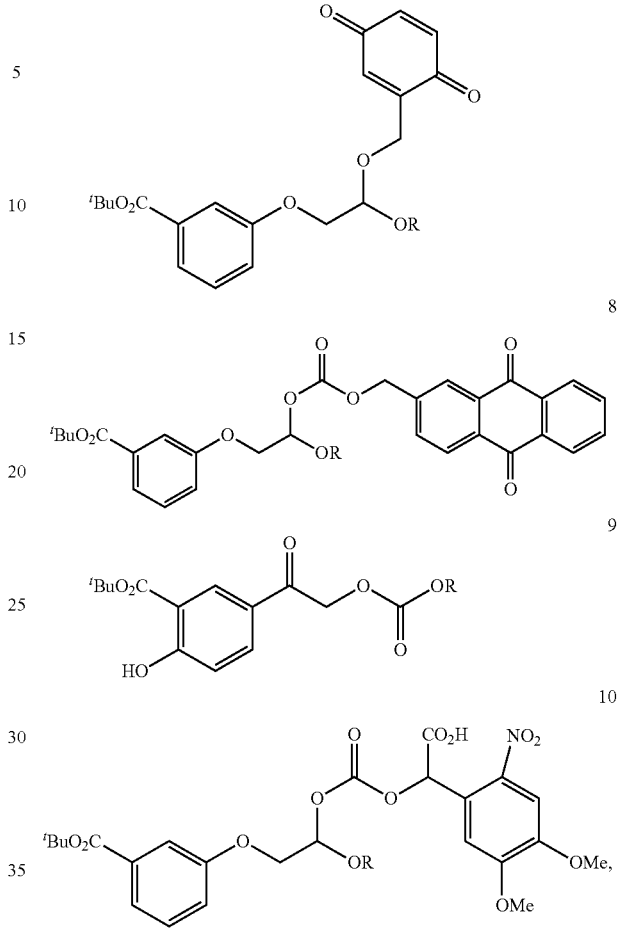

wherein R is any nucleotide or a derivative thereof.

7. The reporter composition of claim 1, wherein a number of an alkyl group, an oxy alkyl group, an alcohol group, a carboxyl group, an amine group, am amide group, an aromatic group, and a naphthalene group, and any combinations thereof in the linear or branched chain is 1 to 1000.

8. The reporter composition of claim 1, wherein the linker molecule or the high charge mass moiety is configured not to affect nucleotide polymerization by a polymerase.

9. The reporter composition of claim 1, wherein the high charge mass moiety is configured to extend out from a nucleotide polymerase complex.

10. The reporter composition of claim 1, wherein the linker molecule or the high charge mass moiety is configured to protrude out from a nascent chain so as to reach-down toward the sensitive detection nanostructure or sensor.

11. The reporter composition of claim 1, wherein a net charge mass of the high charge mass moiety is positive or negative, or is variable depending on pH.

12. The reporter composition of claim 1, wherein a net charge mass of the high charge mass moiety is positive in turn in an acidic pH.

13. The reporter composition of claim 1, wherein a net charge mass of the high charge mass moiety is negative in turn in an alkaline pH.

14. A reporter composition comprising one or more selected from the group consisting of the following compounds, and any combinations thereof:

117
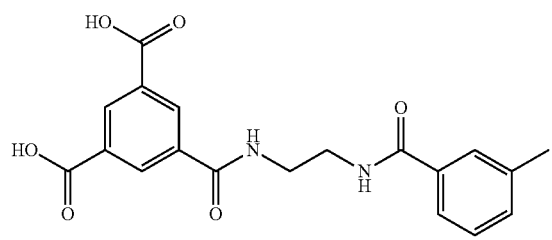
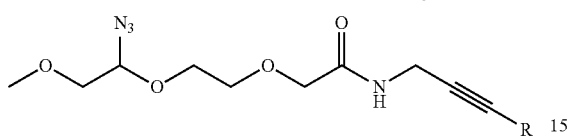
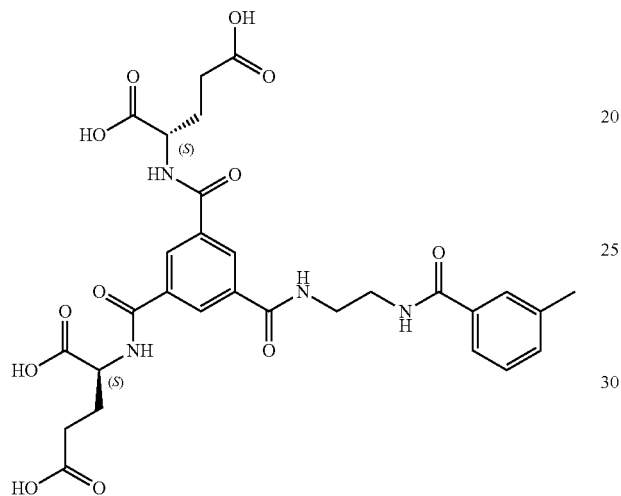
118
-continued
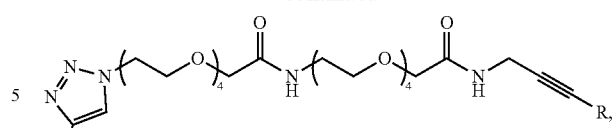
wherein R is any nucleotide or a derivative thereof.
15. The reporter composition of claim 14, wherein the reporter composition comprises one or more selected from the group consisting of the following compounds, and any combinations thereof:
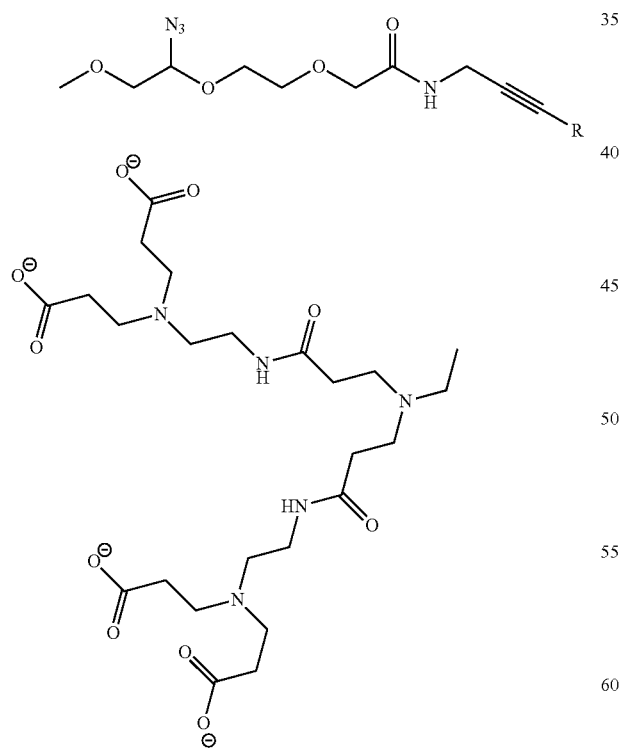

119       120
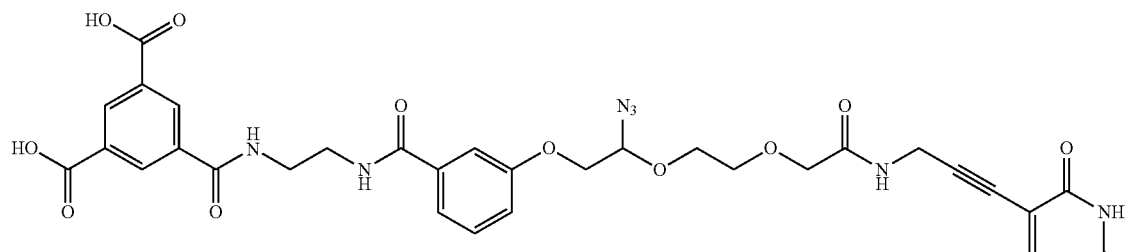
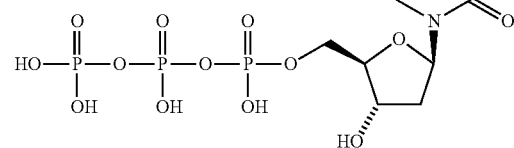
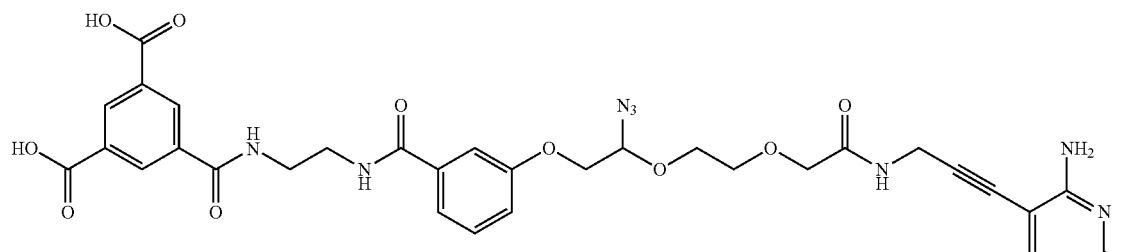
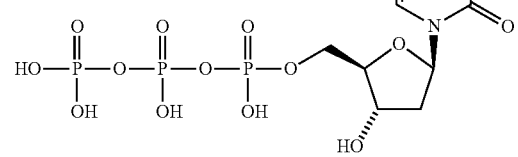
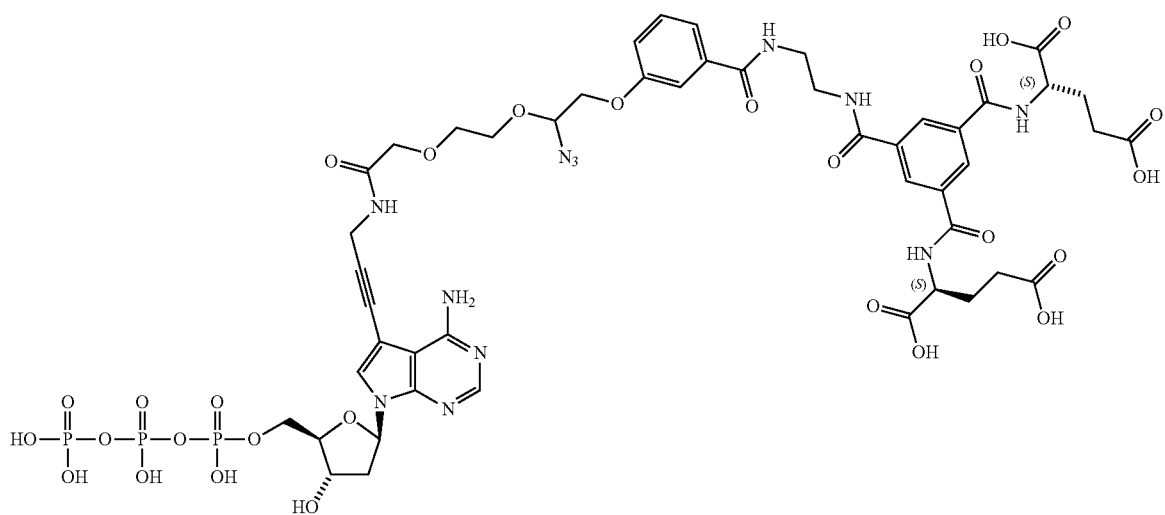

-continued

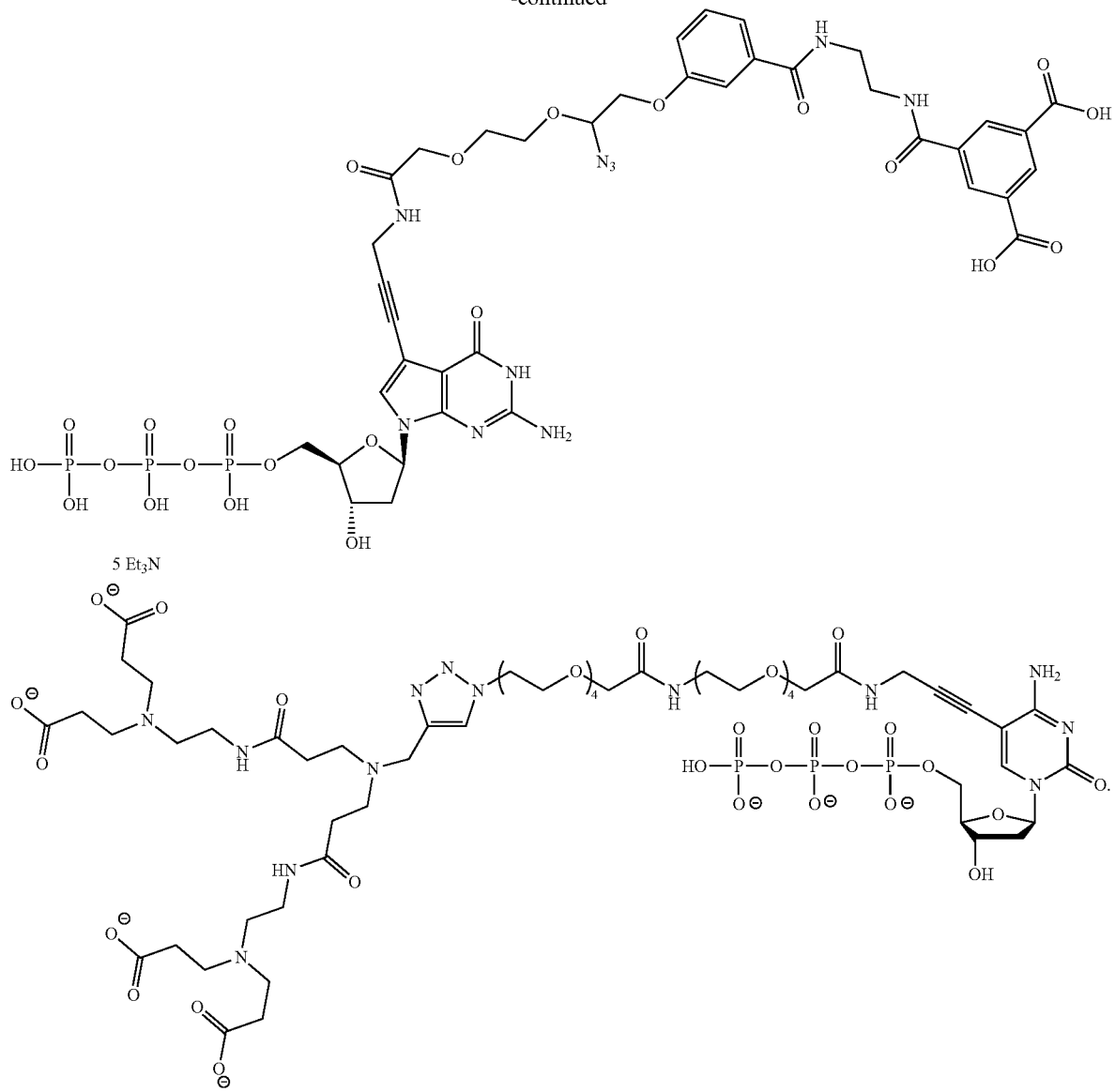

16. A kit for determining a nucleotide sequence, comprising the reporter composition of claim 1.

17. A method of synthesizing the reporter composition of claim 1, comprising:
    generating a first covalent linkage between the nucleotide and a first functional group of the linker, wherein a phosphate group, a sugar or a base of the nucleotide is linked to the first functional group of the linker; and
    generating a second covalent linkage between a second functional group of the linker and any functional group present in the high charge mass moiety.

18. The method of claim 17, wherein the nucleotide comprises a triphosphate group, selected from the group consisting of adenosine triphosphate (ATP), guanosine triphosphate (GTP), cytidine triphosphate (CTP), thymidine triphosphate (TTP), and uridine triphosphate (UTP).

19. The method of claim 17, wherein the phosphate group of the nucleotide comprises thiophosphate or phosphoramidate.

20. The reporter composition of claim 1, wherein the linker molecule and/or the high charge mass moiety is configured to be removable.

* * * * *